United States Patent
Kosaka et al.

(10) Patent No.: US 10,886,025 B2
(45) Date of Patent: Jan. 5, 2021

(54) DRUG ADVERSE EVENT EXTRACTION METHOD AND APPARATUS

(71) Applicant: NEC CORPORATION, Tokyo (JP)

(72) Inventors: Yuki Kosaka, Tokyo (JP); Kazuyo Narita, Tokyo (JP); Satoshi Morinaga, Tokyo (JP); Ayumi Endo, Tokyo (JP); Kaori Yamada, Tokyo (JP); Aiko Kumano, Tokyo (JP); Maki Komamine, Tokyo (JP)

(73) Assignee: NEC CORPORATION, Tokyo (JP)

( * ) Notice: Subject to any disclaimer, the term of this patent is extended or adjusted under 35 U.S.C. 154(b) by 1048 days.

(21) Appl. No.: 15/126,413

(22) PCT Filed: Mar. 18, 2015

(86) PCT No.: PCT/JP2015/058052
§ 371 (c)(1),
(2) Date: Sep. 15, 2016

(87) PCT Pub. No.: WO2015/141724
PCT Pub. Date: Sep. 24, 2015

(65) Prior Publication Data
US 2017/0083670 A1    Mar. 23, 2017

(30) Foreign Application Priority Data
Mar. 20, 2014 (JP) .................. 2014-057635

(51) Int. Cl.
*G16H 50/20* (2018.01)
*G16H 70/40* (2018.01)

(52) U.S. Cl.
CPC ............. *G16H 50/20* (2018.01); *G16H 70/40* (2018.01)

(58) Field of Classification Search
CPC ........ G16H 50/30; G16H 10/60; G16H 50/70; G16H 50/20; G16H 70/40
See application file for complete search history.

(56) References Cited

U.S. PATENT DOCUMENTS 8,543,422 B2    9/2013  Maman
8,676,599 B2    3/2014  Brandt
(Continued)

FOREIGN PATENT DOCUMENTS

JP    2002-342336    11/2002
TW    201232464 A    8/2012
(Continued)

OTHER PUBLICATIONS

Page, David, "Identifying Adverse Drug Events by Relational Learning," Proc Conf AAAI Artif INtell. Jul. 2012; 2012; 790-793 (Year: 2012).*
Search Report from Taiwanese Appln. No. 104108866; date of completion Jun. 1, 2017.
International Search Report, PCT/JP2015/058052, dated Jun. 2, 2015.
(Continued)

*Primary Examiner* — John P Go
(74) *Attorney, Agent, or Firm* — Sughrue Mion, PLLC

(57) ABSTRACT

A method of extracting a combination of a drug and an adverse event related to the drug includes: for each of positive example combinations, negative example combinations and combinations that are neither positive examples nor negative examples, which are combinations of drug and disease, extracting medical events from medical information data about a patient and generating attribute data based on time-series information about the medical events; and learning a discriminant model based on attribute data of the positive and negative examples; and inputting attribute data corresponding to the combinations that are neither positive examples nor negative examples to the discriminant model to determine scores.

20 Claims, 23 Drawing Sheets

(56) References Cited

U.S. PATENT DOCUMENTS

| | | | |
|---|---|---|---|
| 9,454,566 B2 | 9/2016 | Chen | |
| 2002/0010595 A1* | 1/2002 | Kapp | G06Q 50/22 |
| | | | 705/2 |
| 2003/0046110 A1* | 3/2003 | Gogolak | G06F 19/326 |
| | | | 705/2 |
| 2010/0241453 A1* | 9/2010 | Malec | G06F 19/3456 |
| | | | 705/3 |
| 2012/0203566 A1* | 8/2012 | Kidd | G06Q 50/22 |
| | | | 705/2 |
| 2012/0215561 A1 | 8/2012 | Chen | |
| 2013/0085773 A1* | 4/2013 | Yao | G06Q 10/04 |
| | | | 705/2 |
| 2013/0197942 A1* | 8/2013 | Chiu | G06Q 50/22 |
| | | | 705/3 |
| 2013/0226616 A1* | 8/2013 | Nigam | G06Q 10/00 |
| | | | 705/3 |
| 2014/0052464 A1* | 2/2014 | Ray | G06F 19/3418 |
| | | | 705/2 |
| 2014/0095201 A1* | 4/2014 | Farooq | G16H 50/30 |
| | | | 705/3 |
| 2014/0257853 A1 | 9/2014 | Huang | |
| 2015/0025912 A1 | 1/2015 | Kutty | |

FOREIGN PATENT DOCUMENTS

| | | | | |
|---|---|---|---|---|
| TW | 201329902 A | | 7/2013 | |
| TW | 201333740 A | | 8/2013 | |
| TW | 201403532 A | | 1/2014 | |
| TW | 201411546 A | | 3/2014 | |
| WO | WO-2010124137 A1 * | 10/2010 | | G16H 10/60 |

OTHER PUBLICATIONS

Satoshi Morinaga, "Big Data ni Sonaeru",Information Processing Society of Japan Journal of Digital Practices, Jan. 15, 2013 (Jan. 15, 2013), vol. 4, No. 1, pp. 29 to 37.

Tomoko Okuma, "Iyakuhin no Fukusayo Chosa Mokuteki to shita Togoteki Gengo Shori System", Proceedings of the 17th Annual Meeting of the Association for Natural Language Processing Tutorial Honkaigi Workshop [CD-ROM], Mar. 31, 2011 (Mar. 31, 2011), pp. 85 to 88.

Yasuhide Miura, "Denshi Karute kara no Fukusayo Kankei no Jido Chushutsu", Proceedings of the 16th Annual Meeting of the Association for Natural Language Processing, Mar. 8, 2010 (Mar. 8, 2010), pp. 78 to 81.

"2009 OMOP Cup Grand Prize 'Best Submission' Report", David Vogel, Foundation for the National Institute of Health.

Fan et al., "LIBLINEAR: A Library for Large Linear Classification,", Journal of Machine Learning Research, 9 (2008), 1871-1874.

J. Zhou et al., MALSAR: Multi-tAsk Learning via StructurAl Regularization, Arizona State University, 2012.

Chawla et al., "SMOTE: Synthetic Minority Over-sampling Technique," Journal of Artificial Intelligence Research, 16: 321-357 (2002).

Xu-Ying Liu et al., Exploratory Undersampling for Class-Imbalance Learning. Data Mining, 2006. ICDM '06. Sixth International Conference, IEEE Transactions on Systems, Man and Cybernetics—Part B: Cybernetics. vol. 39, No. 2, Apr. 2009.

Sugiyama et al., "Direct Importance Estimation for Covariate Shift Adaption," Annals of the Institute of Statistical Mathematics, vol. 60, No. 4, pp. 699-746, 2008.

* cited by examiner

DRUG ADVERSE EVENT EXTRACTION METHOD AND APPARATUS

TECHNICAL FIELD

The present invention relates to a method and apparatus for extracting adverse events caused by medical drugs by information processing, and in particular to a drug adverse event extraction method and apparatus capable of widely extracting unknown adverse events caused by drugs.

BACKGROUND ART

Though drugs appear on the market after being approved by the government, there may be a case where, when a drug appears on the market and is prescribed to many patients, an unexpected drug adverse event occurs and brings about serious health damage. This is because, since clinical trials performed to gain approval by the government are performed for a limited number of patients in a short period in order to verify the effectiveness of a drug, it is difficult to detect all drug adverse events of the drug by the clinical trials. Therefore, it is an important role of a drug regulatory authority to conduct post-marketing surveillance of drugs on the market to detect drug adverse events that have not been found yet early and carry out safety measures to prevent occurrence of the drug adverse events.

In recent post-marketing surveillance, detection of drug adverse events is performed mainly by analyzing spontaneous reports. Spontaneous reports are reports about events suspected to be drug adverse events that are spontaneously provided by doctors, patients and pharmaceutical companies. However, since all drug adverse events that have actually occurred at clinical sites are not necessarily reported in spontaneous reports, there is a disadvantage that, even if a drug adverse event is detected from spontaneous reports, it is difficult to detect all drug adverse events that have not been found yet.

In order to make up for this disadvantage, attempts to analyze medical information data, which is information about medical services patients have received, to extract information about unknown drug adverse events have been considered recently. In the medical information data, histories of medical examinations for a huge number of patients that have actually occurred at clinical sites for a long period is described in detail unlike spontaneous reports. Therefore, it is expected that drug adverse events that have not been reported by spontaneous reports can be detected by analyzing the medical information data. The medical information data is data obtained from itemized statements of medical fee and itemized statements of dispensing fee, data obtained from medical examination records and the like. The itemized statements of medical fee and itemized statements of dispensing fee are also referred to as health insurance claims, and the medical examination records are also referred to as patients' charts or medical records.

Especially, when a patient receives a medical examination at a medical institution using a medical insurance system or a health insurance system by the government or a private enterprise, the itemized statement of medical fee and the itemized statement of dispensing fee are collected to operators of the medical insurance and the health insurance. Therefore, it is expected that, by analyzing a huge number of itemized statements of medical fee and itemized statements of examination fee collected to the medical and health insurance operators and those entrusted with the insurances, unknown drug adverse events can be detected.

As related art of the present invention, [NPL1] discloses a method of acquiring time-series data showing, for each patient, which drug was prescribed for the patient, and when and which disease occurred in the patient, and extracting drug adverse events by machine learning based on the acquired time-series data. In the method of [NPL1], a combination of "drug and disease" which is already known as a combination indicating a drug adverse event is regarded as a positive example, and a combination of "drug and disease" which is already known as a combination not indicating a drug adverse event is regarded as a negative example. For example, if a certain drug is an antipyretic, and it is known that eruption occurs as an adverse event when the antipyretic is taken, then, the combination of "the drug and eruption" is a positive example. If the antipyretic is prescribed because fever is observed in the patient, the combination of "the antipyretic and fever" is classified as a negative example because the antipyretic itself is a drug for coping with and lowering the fever.

In the method of [NPL1], with positive examples, negative examples, combinations of "drug and disease" which are neither positive examples nor negative examples, and the time-series data of prescription of drugs and occurrence of diseases used as input, attribute data showing when and how many times a disease occurred during a drug prescription period is created for each combination of "drug and disease", and a model for calculating a score indicating the degree of suspicion that a combination of "drug and disease" is an adverse event from the attribute data based on attribute data corresponding to the positive examples and attribute data corresponding to the negative examples. Hereinafter, this model will be called "a discriminant model". Attribute data corresponding to the combinations of "drug and disease" which are neither positive examples nor negative examples is inputted to the learned discriminant model to calculate the above score for each of the combinations of "drug and disease". Since this score indicates the degree of possibility of the inputted combination of "drug and disease" which is neither a positive example nor a negative example being a drug adverse event, combinations of "drug and disease" suspected to be drug adverse events are extracted based on calculated scores.

The technique described in [NPL1] is basically a technique in which, on inputted time-series data of drugs and diseases, attention is paid only to occurrence of the diseases during prescription periods of the drugs, and combinations of "drug and disease" indicating adverse events are extracted from time-series information about prescription of the drugs and time-series information about the observed diseases.

CITATION LIST

Non Patent Literature(s)

[NPL1] "OMOP Cup Grand Prize 'Best Submission' Report", Foundation for the National Institute of Health, [retrieved on Jan. 18, 2014], the Internet <URL: http://omop.fnih.org/sites/default/files/Vogel_Progress_prize_methods_GP_0.pdf>

[NPL2] R.-E. Fan, K.-W. Chang, C.-J. Hsieh, X.-R. Wang, and C.-J. Lin, "LIBLINEAR: A library for large linear classification," Journal of Machine Learning Research, 9(2008), 1871-1874.

[NPL3] J. Zhou, J. Chen and J. Ye, "MALSAR: Multi-tAsk Learning via Structural Regularization," Arizona State University, 2012, [retrieved on Feb. 26, 2014], the Internet <URL: http://www.public.asu.edu/~jye02/Software/MALSAR>

[NPL4] Chawla, N. V., Bowyer, K. W., Hall, L. O., and Kegelmeyer, W. P., "Smote: Synthetic minority over-sampling technique," Journal of Artificial Intelligence Research, 16:321-357 (2002).

[NPL5] Xu-Ying Liu and Jianxin Wu and Zhi-Hua Zhou, "Exploratory Under-Sampling for Class-Imbalance Learning," Data Mining, 2006. ICDM '06. Sixth International Conference on.

[NPL6] Sugiyama, M., Suzuki, T., Nakajima, S., Kashima, H., von Buenau, P., and Kawanabe, M, "Direct importance estimation for covariate shift adaptation," Annals of the Institute of Statistical Mathematics, vol. 60, no. 4, pp. 699-746, 2008.

SUMMARY OF INVENTION

Technical Problem

On the practical use for drug safety measures, it is required to extract drug adverse events from medical information data with a high accuracy. Here, the high accuracy refers to extraction of broad kinds of adverse events with few mistakes. This is because it is important to grasp broad kinds of adverse events accurately in order to prevent health damage due to adverse events.

In order to derive a rule for discriminating between a positive example and a negative example as in the technique described in [NPL1], it is necessary that there is some difference in attribute data used for learning a discriminant model between positive examples and negative examples. If the difference does not exist, it is not possible to, when attempting to perform classification into positive examples and negative examples by allocating a high score to the positive examples and a low score to negative examples, calculate such scores that distinguish between the positive examples and the negative examples.

In the technique described in [NPL1], attribute data showing the occurrence time and occurrence frequency of a disease during a prescription period of a drug is created for each of positive examples and negative examples, and the attribute data is inputted. In the attribute data used in the [NPL1], however, a difference between the content of attribute data of a combination indicating an adverse event (a positive example combination) and the content of attribute data of a combination which is not an adverse event (a negative example combination) may be small In such a case, it is difficult to discriminate between a combination indicating an adverse event and a combination which is not an adverse event only from the attribute data created from the time-series information about drugs and diseases. Therefore, the technique described in [NPL1] has a problem that it is not possible to broadly extract only combinations indicating adverse events with few mistakes.

Hereinafter, description will be made on an example in which the difference in attribute data is small between a combination indicating an adverse event and a combination which is not an adverse event.

The combination which is not an adverse event shows a disease which is hardly thought to be caused by prescription of a drug. As an example thereof, a combination of "drug and disease", which are a certain disease and a drug prescribed for the purpose of treatment of the disease, is given. As for this combination, since the drug is prescribed for the purpose of treatment of the disease when the disease occurs, the number of times that prescription of the drug and occurrence of the disease occur on the same day is large on time-series information about drugs and diseases. On the other hand, among adverse events, there is such an adverse event that a symptom appears immediately after a drug is prescribed, such as an allergic reaction. As for a disease indicating such an adverse event also, the number of times that the disease occurs on the same day when a drug is prescribed is large on the time-series information about drugs and diseases. Therefore, there may be a case where the difference in the content of the attribute data showing when and how many times disease occurred after prescription of a drug is small between a combination indicating an adverse event and a combination which is not an adverse event. In this case, it is not possible to distinguish between the combination indicating an adverse event and the combination which is not an adverse event even if a discriminant model is used.

Thus, an object of the present invention is to solve the problem of the related art and provide a drug adverse event extraction method and apparatus capable of accurately extracting a combination of a drug and an adverse event related to the drug.

Solution to Problem

A drug adverse event extraction method of the present invention is a drug adverse event extraction method of extracting a combination of a drug and a disease corresponding to a drug adverse event, the method comprising, on the assumption that combinations already known as combinations indicating drug adverse events are regarded as positive example combinations, combinations already known as combinations not being drug adverse events are regarded as negative example combinations, and given combinations being neither positive example combinations nor negative example combinations are regarded as combinations other than positive and negative examples:

generating, using medical information data that includes time-series information about medical events for each patient, attribute data for each of the positive example combinations, for each of the negative example combinations and for each of the combinations other than positive and negative examples, based on the time-series information about the medical events;

learning a discriminant model by the attribute data corresponding to the positive example combinations and the attribute data corresponding to the negative example combinations;

inputting the attribute data corresponding to the combinations other than positive and negative examples to the discriminant model to calculate scores; and applying an extraction condition to the score calculated for each of the combinations other than positive and negative examples to extract combinations other than positive and negative examples being suspected to be drug adverse events, wherein the medical events for each patient include prescription of a drug for the patient and a disease observed in the patient, and wherein the medical events for each patient further include at least one of a medical act performed for the patient and an event showing that the medical act has been performed accompanying the medical act performed for the patient.

A drug adverse event extraction apparatus of the present invention is a drug adverse event extraction apparatus for extracting a combination of a drug and a disease corresponding to a drug adverse event, the apparatus comprising, on the assumption that combinations already known as combinations indicating drug adverse events are regarded as positive example combinations, combinations already known as combinations not being drug adverse events are regarded as negative example combinations, and given combinations being neither positive example combinations nor negative example combinations are regarded as combinations other than positive and negative examples:

attribute creation means that generates, using medical information data that includes time-series information about medical events for each patient stored in a storage device, attribute data for each of the positive example combinations stored in the storage device, for each of the negative example combinations stored in the storage device and for each of the combinations other than positive and negative examples stored in the storage device, based on the time-series information about the medical events, and stores the attribute data into the storage device;

learning means that learns a discriminant model by the attribute data corresponding to the positive example combinations and the attribute data corresponding to the negative example combinations;

calculation means that inputs the attribute data corresponding to the combinations other than positive and negative examples stored in the storage device to the discriminant model to calculate scores; and extraction means that applies an extraction condition to the score calculated for each of the combinations other than positive and negative examples to extract combinations other than positive and negative examples being suspected to be drug adverse events, wherein the medical events for each patient include prescription of a drug for the patient and a disease observed in the patient, and wherein the medical events for each patient further include at least one of a medical act performed for the patient and an event showing that the medical act has been performed accompanying the medical act performed for the patient.

According to the present invention, it becomes possible to accurately extract a combination of a drug and an adverse event related to the drug.

DESCRIPTION OF EMBODIMENTS

Figure 1:
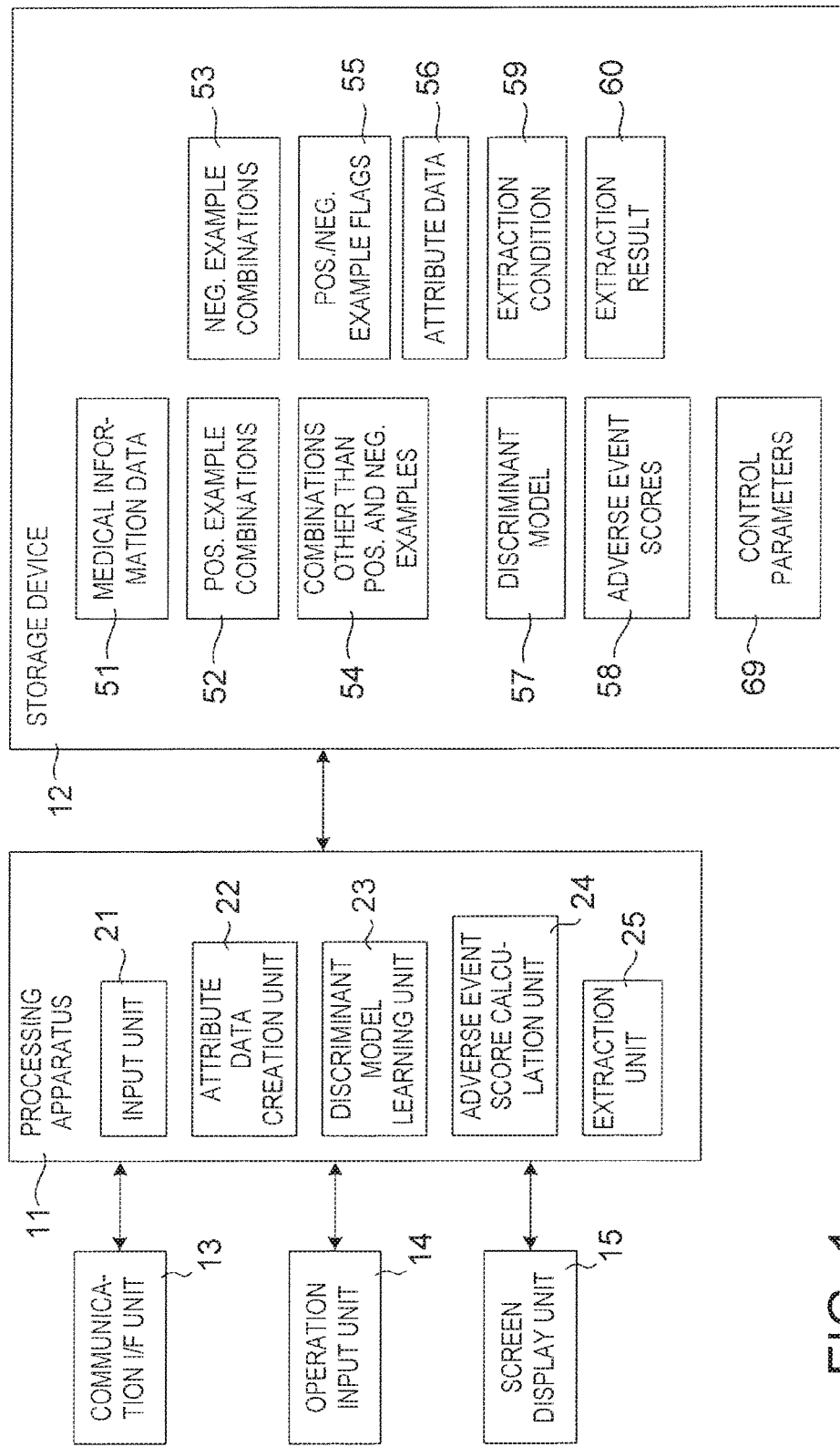
FIG. 1 is a block diagram showing a configuration of a drug adverse event extraction apparatus of an exemplary embodiment.

Next, exemplary embodiments will be described with reference to drawings.

First, time-series information about medical events will be described.

Medical information data such as an itemized statement of medical fee, an itemized statement of dispensing fee and medical examination record information can be regarded as time-series information about medical events for each patient because the medical information data includes record about medical treatment for each day for the patient. Here, a medical event refers to a medical-related event which occurs on a particular patient at a particular time point, such as a certain patient having a disease observed, having a particular drug prescribed, receiving a particular medical act or receiving a diagnosis of a particular disease at a certain time point. Here, more generally, information related to medical services in a broad sense, such as written matters about a particular item at a particular time point for a particular patient, medical expenses, a hospital department and hospitalization, which is included in the medical information data is also referred to as a medical event. Therefore, in the present specification, a medical event is defined as such that includes not only a disease which occurs in a patient but also a medical act performed for the patient and an event showing that the medical act was performed accompanying the medical act performed for the patient. It goes without saying that the medical event "hospitalization" indicates that a particular patient was hospitalized at a particular time point; the medical event "medical expenses" indicates that a particular amount of medical expenses at a particular time point for a particular patient is charged; and the medical event "hospital department" indicates a hospital department at which a particular patient had a medical examination at a particular time point. For example, measures such as a treatment act at a particular hospital department, prescription of a drug and hospitalization are included in medical acts, and request for medical expenses is given as an event showing that a medical act was performed accompanying the medical act.

Further, the time-series information about medical events is assumed to be such that whether particular drug A was prescribed for certain patient X is expressed in appropriately separated time units (for example, units of one month), for example, as shown below.

Patient X; Drug A: 0, 0, 0, 1, 1, 0, 0

Here, occurrence of the event is indicated by "1", and non-occurrence is indicated by "0". In this example, it is shown that prescription of drug A for patient X is not performed for the first three months (that is, the first to third months), performed for the following two months (the fourth and fifth months), and not performed for the further following two months (the sixth and seventh months).

Though whether prescription of a drug occurs or not is expressed by binary data of "0" and "1" in the above example, the expression is not limited to binary data. It is also possible to express the amount of prescription in an appropriate unit to express information in detail as shown below:

Patient X; Drug A: 0, 0, 0, 2.3, 6.18, 0, 0

Further, though a medical event indicating prescription of a drug is shown in the above example, it is also possible to give information about a hospital department at which each medical drug was prescribed to express the medical event in detail as shown below:

Patient X; Drug A; Internal medicine department: 0, 0, 0, 1, 1, 0, 0

Patient X; Drug A; Surgery department: 0, 0, 0, 1, 0, 0, 0

Further, one of the kinds of medical events included in the medical information data is medical expenses. This event indicates that a particular amount of medical expenses at a particular time point for a particular patient is charged. As an example of time-series information about the medical event of medical expenses, how much is charged for medical expenses for certain patient X is expressed by a billing amount in an appropriate unit (for example, medical fee point) as shown below.

Patient X; Medical expenses: 300, 550, 90, 140, 2500, 600, 0

Medical information data includes time-series information about a plurality of kinds of medical events for an enormous number of patients. For example, the following example shows time-series information about a plurality of kinds of medical events for two patients.

Patient X; Drug A: 0, 0, 0, 1, 1, 0, 0
Patient X; Drug B: 0, 0, 0, 0, 0, 1, 0
Patient X; Medical act C: 0, 0, 1, 1, 1, 0, 0
Patient X; Diagnosed disease name D: 0, 0, 0, 0, 1, 1, 0
Patient X; Hospitalization: 0, 0, 0, 0, 1, 0, 0
Patient X; Internal medicine department (hospital department): 0, 0, 1, 1, 1, 1, 0
Patient Y; Drug A: 0, 0, 1, 1, 1, 1, 1
Patient Y; Drug C: 0, 0, 0, 1, 1, 1, 0

The above example shows, for drugs A and B having been prescribed for patient X, medical act C having been performed for patient X, disease name D having been diagnosed for patient X, patient X having been hospitalized, and patient X having had a medical examination at an internal medicine department, when each occurred. It is also shown when prescription of drugs A and C occurred for patient Y.

Hereinafter, for simplification, the medical event "diagnosed disease name" is referred to as "disease". When "diagnosed disease name" is replaced with "disease" in the above example, the following result is obtained.

Patient X; Drug A: 0, 0, 0, 1, 1, 0, 0
Patient X; Drug B: 0, 0, 0, 0, 0, 1, 0
Patient X; Medical act C: 0, 0, 1, 1, 1, 0, 0
Patient X; Disease D: 0, 0, 0, 0, 1, 1, 0
Patient X; Hospitalization: 0, 0, 0, 0, 1, 0, 0
Patient X; Internal medicine department (hospital department): 0, 0, 1, 1, 1, 1, 0
Patient Y; Drug A: 0, 0, 1, 1, 1, 1, 1
Patient Y; Drug C: 0, 0, 0, 1, 1, 1, 0

FIG. 1 shows a configuration of a drug adverse event extraction apparatus of an exemplary embodiment. This drug adverse event extraction apparatus has a function of extracting a combination indicating an adverse event from among combinations of "drug and disease" based on time-series information about medical events for a large number of patients included in medical information data. Especially, this apparatus extracts a combination indicating an adverse event based on a score calculated for each combination, that is, a numerical value indicating suspicion as an adverse event. In the description below, the combination of "drug and disease" will be referred to simply as a "combination" as far as it is apparent from the context.

As shown in FIG. 1, the drug adverse event extraction apparatus is provided with processing apparatus 11 that executes data processing; storage device 12 that is connected to processing apparatus 11 and that is for storing medical information data to be a target of extraction of drug adverse events, and for storing data required for data processing at processing apparatus 11 and generated as a result of data processing, such as a discriminant model, scores and an extraction result; communication interface (I/F unit) 13; operation input unit 14; and screen display unit 15. All of communication interface unit 13, operation input unit 14 and screen display unit 15 are connected to processing apparatus 11.

Communication interface unit 13 is configured with a dedicated data communication circuit and has a function of performing data communication between various kinds of apparatuses not shown and processing apparatus 11 that are connected via a communication circuit. Operation input unit 14 is configured with operation input devices such as a keyboard and a mouse and has a function of detecting an operator's operation and performing output to processing apparatus 11. Screen display unit 15 is configured with a screen display apparatus such as an LCD (liquid crystal display) and a PDP (plasma display panel) and has a function of screen-displaying various kinds of information, such as an operation menu and a selection result, in response to an instruction from processing apparatus 11.

Storage device 12 is configured with a hard disk, a semiconductor memory device or the like. In the drug adverse event extraction apparatus shown in FIG. 1, main information stored in storage device 12 are: medical information data 51, positive example combinations 52, negative example combinations 53, combinations other than positive and negative examples 54, positive/negative example flags 55, attribute data 56, discriminant model 57, adverse event scores 58, extraction condition 59, extraction result 60 and control parameters 69. In addition to these, information used for the operation of the drug adverse event extraction apparatus may be stored in storage device 12. The above information will be described below.

Medical information data 51 is information obtained from itemized statements of medical fee, itemized statements of dispensing fee, medical record and the like as described above, and this is expressed as time-series information about medical events for each patient. In the present exemplary embodiment, medical information data 51 is configured with medical events that occurred at particular time points for particular patients, including a certain patient (a) having a particular drug prescribed, (b) having a particular disease observed, (c) receiving a particular medical act, (d) being charged for a particular amount of medical expenses, (e) having a medication examination at a particular hospital department and (f) being hospitalized, at certain points of time. Though the details of the medical events will be described later, items other than those given here can be used as medical events in the present invention if the items are related to medical services in a broad sense. Further, in the present invention, it is also possible not to use a part of the medical events (c) to (f) described here depending on how the combination of "drugs and disease" to be a drug adverse events is found out. As described in relation to [NPL1], it is not possible to accurately extract a drug adverse event from time-series data of prescription of drugs and occurrence of diseases. Therefore, in the present exemplary embodiment, attention is paid not only to a disease but also to medical events other than occurrence of the disease during a prescription period of a drug. In the present exemplary embodiment, it is preferable that the medical information data is information obtained from either itemized statements of medical fee or itemized statements of dispensing fee.

The present invention is for making it possible to discriminate whether a result of an adverse event was caused by prescription of a drug. Therefore, examples of combining an event to be a cause (a preceding event, that is, prescription of a drug) and an event possibly to be a result (a succeeding event, that is, an observed disease) are considered, and, for each combination, whether the event is an adverse event related to the drug is considered. Thus, in the present exemplary embodiment, positive example combinations 52, negative example combinations 53 and combinations other than positive and negative examples 54, all of which are combinations of "drug and disease" are assumed. Positive example combinations 52 are combinations of "drug and disease" which are already known as combinations indicating drug adverse events. Negative example combinations 53 are combinations of "drug and disease" which are already known as combinations that are not drug adverse events. In comparison, combinations other than positive and negative examples 54 means such that are combinations of "drug and disease" but are neither positive example combinations nor negative example combinations. Therefore, combinations other than positive and negative examples 54 are combinations that are known neither as combinations indicating drug adverse events nor as combinations that are not drug adverse events.

Positive/negative example flags 55 are flag values according to combinations, which indicate whether a positive/negative example combination is a positive example combination or a negative example combination. As the flag values, for example, a value indicating a positive example is set for a positive example combination, and a value indicating a negative example is set for a negative example combination.

Attribute data 56 is data showing, for each of the positive examples, the negative examples and the combinations other than positive and negative examples, characteristics on the medical information data. The details of the attribute data in the present exemplary embodiment will be described later.

Discriminant model 57 is a model that shows a relationship between attribute data corresponding to a combination and whether the combination corresponds to an adverse event or not. As a form of discriminant model 57, for example, a logistic regression model, a linear support vector machine (SVM) model and the like are conceivable.

Adverse event score 58 is a value indicating suspicion as an adverse event that is calculated for each of combinations other than positive and negative examples 54 by discriminant model 57. The larger the value is, the stronger the suspicion as an adverse event is.

Extraction condition 59 shows a condition to be satisfied at the time of extracting a combination indicating an adverse event from among combinations other than positive and negative examples 54. Examples of the extraction condition include a threshold for adverse event scores of combinations to be extracted, the maximum number of combinations to be extracted, and the like.

Extraction result 60 is a list of combinations extracted from among combinations other than positive and negative examples 54, as combinations indicating adverse events.

Control parameters 69 are various kinds of parameters specifying an execution condition for a drug adverse event extraction process and the like in processing apparatus 11.

Next, processing apparatus 11 will be described.

The drug adverse event extraction apparatus of the present exemplary embodiment learns discriminant model 57 by positive example combinations 52 and negative example combinations 53 and, after that, applies combinations other than positive and negative examples 54 to discriminant model 57 to obtain adverse event scores 58 for combinations other than positive and negative examples 54. In order to execute such a process, processing apparatus 11 is provided with input unit 21, attribute data creation unit 22, discriminant model learning unit 23, adverse event score calculation unit 24 and extraction unit 25. Attribute data creation unit 22 corresponds to attribute creating means; discriminant model learning unit 23 corresponds to learning means; adverse event score calculation unit 24 corresponds to calculation means; and extraction unit 25 corresponds to extraction means.

Input unit 21 inputs information required for the process in the drug adverse event extraction apparatus, such as medical information data, positive example combinations, negative example combinations, combinations other than positive and negative examples and an extraction condition, from communication interface unit 13 or operation input unit 14 and stores the information into storage device 12. Here, the medical information data given to input unit 12 is assumed to be time-series information about medical events for each patient extracted from itemized statements of medical fee, itemized statements of dispensing fee and the like. Recently, itemized statements of medical fee and itemized statements of dispensing fee are created as electronic data in a pre-defined data format, and the data format itself shows time-series information about medical events. Therefore, it is extremely easy to extract the time-series information about medical events for each patient from itemized statements of medical fee and itemized statements of dispensing fee.

Attribute data creation unit 22 reads positive example combinations 52, negative example combinations 53, combinations other than positive and negative examples 54 and medical information data 51 from storage device 12 and performs preprocessing for medical information data 51 which has been read. After that, attribute data creation unit 22 creates attribute data using the read information and stores the attribute data into storage device 12. The preprocessing is not necessarily to be performed, depending on the data format of the medical information data and the like.

Discriminant model learning unit 23 has a function of: reading positive example combinations 52 and negative example combinations 53, the attribute data corresponding to the positive examples and the negative examples among attribute data 56 and positive/negative example flags 55 from storage device 12; learning discriminant model 57; and storing learned discriminant model 57 into storage device 12.

Adverse event score calculation unit 24 has a function of: reading combinations other than positive and negative examples 54 and the attribute data corresponding to the combinations other than positive and negative examples from storage device 12; inputting the read attribute data to the discriminant model to calculate an adverse event score for each of the combinations other than positive and negative examples; and storing the calculated adverse event score into storage device 12.

Extraction unit 25 has a function of: reading adverse event scores 58 and extraction condition 59 from storage device 12; extracting a combination suspected to be an adverse event, from among the combinations other than positive and negative examples in a manner that the extraction condition is satisfied; and storing a result of the extraction into storage unit 12. Further, extraction unit 25 also has a function of outputting the extraction result to screen display unit 15 or to the outside via communication interface unit 13.

Next, the operation of the drug adverse event extraction apparatus shown in FIG. 1 will be described with reference to FIG. 2. The operation of the drug adverse event extraction apparatus is roughly divided in four phases of attribute data creation phase S1, learning phase S2, adverse event score calculation phase S3 and extraction phase S4, and the phases are executed in that order.

At attribute data creation phase S1, input unit 21 receives medical information data, each combination of positive examples, negative examples, combinations other than positive and negative examples from communication interface unit 13 or operation input unit 14 and stores them into storage device 12 at step S11. Next, at step S12, attribute data creation unit 22 reads out medical information data 51, positive example combination 42, negative example combinations 53 and combinations other than positive and negative examples 54 from storage device 12, performs preprocessing for medical information data 51. After that, at step S13, attribute data creation unit 22 creates attribute data corresponding to each of the read-out combinations and stores the created attribute data into device apparatus 12.

The attribute data is data showing, for a combination, characteristics of occurrence and non-occurrence of other medical events at a time close to a time point when the drug and the disease of the combination co-occur on the same patient, on inputted time-series information about medical events.

At learning phase S2, discriminant model learning unit 23 calls positive example combinations 52, negative example combinations 53, attribute data 56 corresponding to the positive and negative examples, positive/negative example flags 55 and discriminant model 57 from storage device 12 at step S21, and learns the discriminant model using these at step S22. The learned discriminant model is returned to storage device 12.

At adverse event score calculation phase S3, adverse event score calculation unit 24 reads out discriminant model 57, combinations other than positive and negative examples 54 and the attribute data corresponding to the combinations from storage device 12 at step S31, and applies the read-out attribute data to the discriminant model to calculate adverse event scores at step S32. The calculated adverse event scores are stored into storage device 12.

At extraction phase S4, input unit 21 receives an extraction condition from communication interface unit 13 or operation input unit 14 and stores the extraction condition into storage device 12 at step S41 first. Next, at step S42, extraction unit 25 reads out adverse event scores 58 and extraction condition 59 from storage device 12, extracts combinations indicating adverse events from among the combinations other than positive and negative examples in a manner that the extraction condition is satisfied, and stores a result of the extraction into storage device 12. After that, at step S43, extraction unit 25 outputs the extraction result to screen display unit 15 or to the outside via communication interface unit 13. At this time, it is preferable to preferentially extract a combination with a high adverse event score, which is strongly discriminated as an adverse event, and prevent a combination with a low adverse event score from being preferentially extracted. That is, it is preferable to sort and output the combinations other than positive and negative examples in descending order of the level of being suspected to be an adverse event. Further, it is possible to input a lot of combinations of "drug and disease" for various drugs in the present exemplary embodiment, and, in this case, it is preferable to furthermore output a result of sorting in order of adverse event scores for each kind of drug because it is convenient to know combinations suspected to be adverse events for each drug.

Next, operations of attribute data creation phase S1, learning phase S2, adverse event score calculation phase S3 and extraction phase S4 will be described in more detail.

(1) Details of attribute data creation phase S1

(1-1) Step S11

At step S11, medical information data 51, combinations of positive examples and negative examples, and combinations other than positive and negative examples (that is, positive example combinations 52, negative example combinations 53 and combinations other than positive and negative examples 54) and a period length condition are read out from storage device 12. Examples of the positive examples, the negative examples, and the combinations other than positive and negative examples will be shown below. At attribute data creation phase S1, all combinations are treated equally without being conscious of whether each combination is a positive example, a negative example or a combination other than positive and negative examples. The period length condition is stored in storage device 12 in advance as one of control parameters 69.

Examples of combinations read out from storage device 12 are shown below.

(Drug A; Disease C), (Drug B; Disease B), (Drug C; Disease A), . . . .

Further, an example of inputted medical information data 51 is shown below. It is assumed that inputted medical information data is the data shown below. Though the time unit is a month in the example, the time unit may be a day, a week or a year. Hereinafter, for simplification, description will be made on the case where the time unit is a month.

Patient X, Drug A; Internal medicine department: 0, 0, 1, 0, 0, 0, 0
Patient X, Drug B; Internal medicine department: 1, 0, 1, 0, 0, 0, 0
Patient X; Disease A: 0, 0, 0, 0, 1, 0, 0
Patient X; Medical act C: 1, 0, 1, 1, 1, 0, 0
Patient X; Medical act D: 0, 0, 1, 1, 1, 0, 0
Patient X; Hospitalization: 0, 1, 0, 1, 1, 0, 0
Patient X; Internal medicine department (hospital department): 0, 0, 1, 1, 1, 0, 0
Patient X, Medical expenses: 300, 550, 90, 140, 2500, 600, 0
Patient Y, Drug A; Internal medicine department: 0, 0, 0, 0, 1, 0, 0
Patient Y, Drug C; Dermatology department: 0, 0, 1, 0, 1, 0, 0
Patient Y; Disease A: 0, 0, 1, 0, 1, 0, 0
Patient X; Disease D: 0, 0, 0, 0, 1, 1, 0
Patient Y; Hospitalization: 0, 0, 0, 0, 1, 0, 0
Patient Y; Internal medicine department (hospital department): 0, 0, 1, 0, 1, 1, 0
Patient Y; Dermatology department (hospital department): 0, 0, 0, 0, 1, 0, 0
Patient Y; Medical expenses: 0, 0, 190, 0, 1650, 400, 0
Patient Z, Drug B; Internal medicine department: 0, 1, 1, 1, 0, 0, 0
Patient Z; Disease A: 0, 1, 1, 0, 0, 0, 0
Patient Z; Disease D: 0, 0, 0, 1, 0, 0, 1
Patient Z; Medical act C: 0, 1, 1, 1, 0, 0, 1
Patient Z; Hospitalization: 0, 1, 0, 1, 0, 0, 0
Patient Z; Internal medicine department (hospital department): 0, 0, 1, 1, 0, 0, 0
Patient Z; Surgery department (hospital department): 0, 0, 1, 1, 0, 0, 1
Patient Z; Medical expenses: 0, 390, 550, 1000, 0, 0, 300

(1-2) Step S12

At step S12, time-series information about new medical events required for creation of attribute data performed at the next step is created by performing preprocessing described below for medical information data 51 read out from storage device 12 at step S11. Furthermore, as for the time-series information about each medical event included in medical information data 51 read out from storage device 12, since it is not necessary to treat the time-series information about the medical event in certain predetermined units, the unit of the medical event is converted to a different unit, and time-series information about the medical event in the converted unit is newly created. Furthermore, if time-series information other than binary data, such as real numbers, is included in medical information data 51, the time-series information is converted to binary data in order to make it easy to create attribute data.

As the time-series information about new medical events required for creation of attribute data, there are three kinds of pieces of time-series information about "simultaneous medical acts", "combined drugs" and "hospital department change". These new medical events represent the following meanings, respectively.

The "simultaneous medical acts" is a medical event indicating that a larger number of kinds of medical acts than a predetermined threshold were simultaneously performed for a particular patient at a particular time point. Further, the "combined drugs" is a medical event indicating that a larger number of kinds of drugs than a predetermined threshold were simultaneously prescribed for a particular patient at a particular time point. The "hospital department change" is a medical event indicating that, from a hospital department different from a hospital department from which a particular drug was prescribed, another drug was prescribed for a particular patient at a particular time point.

As for the time-series information about the medical events of "simultaneous medical acts", "combined drugs" and "hospital department change", it is not necessary to newly create the time-series information if the time-series information is directly included in inputted medical information data such as itemized statements of medical fee and medical examination record information. If the time-series information is not included in the medical information data, however, it is necessary to perform preprocessing for the medical information data and newly create those medical events. A method for creating the time-series information about the three medical events of "simultaneous medical acts", "combined drugs" and "hospital department change" from the medical information data will be described below.

An example of creating time-series information about the medical event of "simultaneous medical acts" as preprocessing will be shown. It is assumed that a plurality of pieces of time-series information exists for the same patient for each classification of medical act as shown under (Before conversion). By counting how many medical acts the patient received each month, time-series information about the medical event of "simultaneous medical acts" can be created as shown under (After conversion). In the example below, description will be made on a case where the threshold is set to 20, 10, 7 and 5. The threshold is one of control parameters 69.

(Before Conversion)
Patient X; Medical act A: 0, 0, 1, 0, 0, 1, 0
Patient X; Medical act B: 0, 0, 1, 0, 0, 1, 0
Patient X; Medical act C: 0, 0, 1, 0, 0, 1, 0
Patient X; Medical act D: 0, 0, 1, 0, 1, 0, 0
Patient X; Medical act E: 0, 0, 1, 0, 0, 0, 0
Patient X; Medical act F: 0, 0, 1, 0, 0, 1, 0
Patient X; Medical act G: 0, 0, 1, 0, 0, 1, 0
(After Conversion)
Patient X; Simultaneous medical acts (20 kinds or more): 0, 0, 0, 0, 0, 0, 0
Patient X; Simultaneous medical acts (10 kinds or more): 0, 0, 0, 0, 0, 0, 0
Patient X; Simultaneous medical acts (7 kinds or more): 0, 0, 1, 0, 0, 0, 0
Patient X; Simultaneous medical acts (5 kinds or more): 0, 0, 1, 0, 0, 1, 0

Next, an example of creating time-series information about the medical event of "combined drugs" as preprocessing will be shown. It is assumed that a plurality of pieces of time-series information exists for the same patient for each classification of drug as shown under (Before conversion). By counting how many drugs were prescribed for the patient each month, time-series information about the medical event of "combined drugs" can be created as shown under (After conversion). In the example below, description will be made on a case where the threshold is set to 20, 10, 7 and 5.
(Before Conversion)

Patient X, Drug A; Internal medicine department: 0, 0, 1, 0, 0, 1, 0
Patient X, Drug B; Surgery department: 0, 0, 1, 0, 0, 1, 0
Patient X, Drug C; Internal medicine department: 0, 0, 1, 0, 0, 1, 0
Patient X, Drug D; Internal medicine department: 0, 0, 1, 0, 1, 0, 0
Patient X, Drug E; Internal medicine department: 0, 0, 1, 0, 0, 0, 0
Patient X, Drug F; Internal medicine department: 0, 0, 1, 0, 0, 1, 0
Patient X, Drug G; Internal medicine department: 0, 0, 1, 0, 0, 1, 0
(After Conversion)
Patient X; Combined drugs (20 kinds or more): 0, 0, 0, 0, 0, 0, 0
Patient X; Combined drugs (10 kinds or more): 0, 0, 0, 0, 0, 0, 0
Patient X; Combined drugs (7 kinds or more): 0, 0, 1, 0, 0, 0, 0
Patient X; Combined drugs (5 kinds or more): 0, 0, 1, 0, 0, 1, 0

Next, an example of creating time-series information about the medical event of "hospital department change" as preprocessing will be shown. It is assumed that a plurality of pieces of time-series information exists for the same patient for each classification of combination of a drug and a hospital department at which the drug was prescribed, as shown under (Before conversion). By checking, for each combination of a drug and a hospital department at which the drug was prescribed, whether some drug was prescribed during the same month from a hospital department different from the hospital department at which the drug was prescribed, time-series information about the medical event of "hospital department change" can be created as shown under (After conversion). An example of creation of the time-series information about the medical event of "hospital department change" will be shown below.
(Before Conversion)
Patient X, Drug A; Internal medicine department: 0, 0, 1, 0, 0, 1, 0
Patient X, Drug B; Surgery department: 0, 1, 0, 0, 0, 1, 0
Patient X, Drug C; Dermatology department: 0, 0, 0, 1, 1, 1, 0
(After Conversion)
Patient X, Hospital department change (Drug A): 0, 1, 0, 1, 1, 0, 0
Patient X, Hospital department change (Drug B): 0, 0, 1, 1, 1, 0, 0
Patient X, Hospital department change (Drug C): 0, 1, 1, 0, 0, 0, 0

As for the time-series information about each medical event included in medical information data 51 read out from storage device 12, since it is not necessary to treat the time-series information about the medical event in certain predetermined units, the unit of the medical event is converted to a different unit, and time-series information about the medical event in the converted unit is newly created.

For example, as for time-series information about a disease, time-series information about new medical events indicating history of the disease which uses ICD10 codes (codes of ICD (International Statistical Classification of Diseases and Related Health Problems), 10th Edition) is created with the use of a table of conversion to ICD10 codes. Furthermore, as for time-series information about a drug, time-series information about a new medical event indicating history of prescription of the drug which uses ATC (Anatomical Therapeutic Chemical Classification System) codes is created with the use of a table of conversion to the ATC codes. Hereinafter, an example of converting time-series information about medical events of "disease" to time-series information using ICD10 codes as preprocessing will be shown as an example. It is assumed that "cardiomyopathy" or "secondary cardiomyopathy" was diagnosed for patient X on a particular month as shown under (Before conversion). In this case, since "cardiomyopathy" and "secondary cardiomyopathy" correspond to the same ICD10 code I429, time-series information about a disease called I429 can be created as shown under (After conversion).
(Before Conversion)
Patient X; Cardiomyopathy: 0, 0, 1, 0, 0, 0, 0
Patient X; Secondary cardiomyopathy: 0, 0, 0, 0, 0, 1, 0
(After Conversion)
Patient X; Cardiomyopathy: 0, 0, 1, 0, 0, 0, 0
Patient X; Secondary cardiomyopathy: 0, 0, 0, 0, 0, 1, 0
Patient X; I429: 0, 0, 1, 0, 0, 1, 0

If time-series information other than binary data, such as real numbers, is included in medical information data, the time-series information is converted to binary data in order to make it easy to create attribute data. For example, there may be a case where time-series information about the medical event of "medical expenses" is written in medical information data as real number time-series information. Therefore, description will be made on the time-series information about the medical event of "medical expenses" below as an example of a conversion target.

In order to detect a drug adverse event, it is more appropriate to convert the time-series information to information with rougher granularity, such as information about whether high medical expenses or low medical expenses, than to handle detailed information such as the amount of "medical expenses". Further, by converting the time-series information to the 0/1 binary data format like the other medical events included in medical information data, time-series information included in the medical information data can be uniformed in the same format, and therefore, a merit that it becomes easy to handle the medical information data is obtained.

Therefore, by setting a predetermined threshold (for example, 1000) and indicating whether or not the threshold is reached or exceeded by "0" and "1", data is converted so that the medical event of "medical expenses" expressed by whether or not the threshold is reached or exceeded. This threshold is also one of control parameters 69.

An example of the medical event of "medical expenses" before and after conversion is shown below. In the example below, description will be made on a case where the threshold is set to 1000 (four digits) and 100 (three digits).
(Before Conversion)
Patient X, Medical Expenses: 300, 550, 90, 140, 2500, 600, 0
(After Conversion)
Patient X; Medical expenses (1000 or more): 0, 0, 0, 0, 1, 0, 0
Patient X; Medical expenses (100 or more): 1, 1, 0, 1, 1, 1, 0

(1-2) Step S13

At step S13, attribute data is created. In the present exemplary embodiment, attribute data $X_n$ is generally represented by a vector constituted by a plurality of elements. When it is assumed that, for each combination of "drug and disease", a number identifying the combination is given, and it is assumed that the number of elements of the first combination (that is, n=1) is 7, $X_1=(0,0,3,2,1,0,0)$ is given. This shows that, for the combination of n=1, the value of attribute item 1 is 0, the value of attribute item 2 is 0, the value of attribute item 3 is 3, the value of attribute item 4 is 2, the value of attribute item 5 is 1, the value of attribute item 6 is 0, and the value of attribute item 7 is 0. The created attribute data is stored into storage device 12.

The attribute data is data showing, for each combination, characteristics of occurrence and non-occurrence of medical events included in the medical information data at a time close to a time point when the drug and the disease of the combination co-occur on the same patient on medical information data. This is created based on the knowledge that, at a timing when an adverse event occurs, it will happen to the patient that higher expenses than before occur for the patient, that hospitalization occurs, that a drug which has been prescribed is stopped, that some drug or medical act for treating the adverse event is newly added, that the patient sees a doctor at a hospital department different from the hospital department where the drug has been prescribed, or the like.

In order to detect a drug adverse event from medical information data with high accuracy, it is necessary that some difference exists in attribute data between a case where an adverse event has occurred and a case where an adverse event has not occurred. Therefore, it can be thought that, by expressing the characteristics of occurrence and non-occurrence of a particular medical event at timing when an adverse event occurs, as attribute data, some difference occurs in the attribute data between the case where an adverse event has occurred and the case where an adverse event has not occurred.

Next, the details of a method for creating the attribute data will be described. The attribute data are roughly classified in the following six kinds.

(Pattern Attribute Data)

Figure 3:
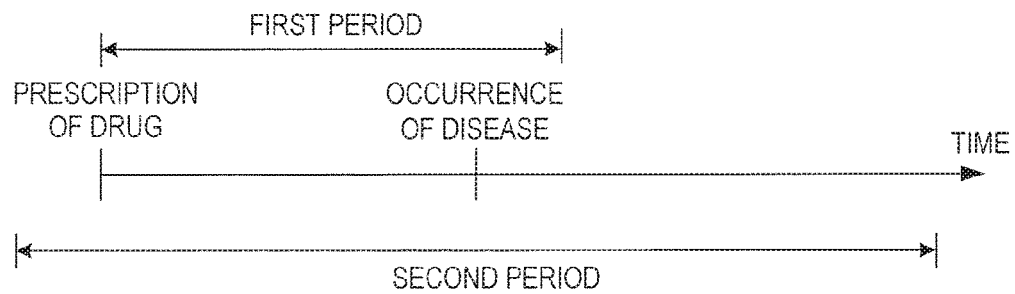
FIG. 3 is a diagram showing a relationship between a first period and a second period.

The first is pattern attribute data. This attribute data is attribute data indicating the rate of occurrence of each of patterns in the whole medical information data. The patterns are obtained as follows. For a combination of a drug and a disease, if the disease occurs on the same patient within a first period with a predetermined length after the drug is prescribed, patterns indicating order of occurrence and non-occurrence of predetermined kinds of medical events are extracted within a second period before and after the time point of occurrence of the disease as a reference, as shown in FIG. 3. The lengths of the first and second periods are determined by a period length condition which is one of control parameters 69.

This attribute is created based on the idea that some difference will appear in order of occurrence and non-occurrence of medical events, such as high medical expenses and hospitalization, during a period before and after occurrence of a disease included in a combination, between a case where an adverse event occurs and a case where an adverse event does not occur.

It can be thought that such a difference occurs, for example, as in the case where high medical expenses do not occur during a period before a disease included in a combination indicating an adverse event occurs, while the rate of occurrence of such a pattern that high medical expenses occur at every time point in succession is high during a period after occurrence of the disease, and, on the other hand, the rate of occurrence of the pattern that high medical expenses occur at every time point in succession is low during a period after occurrence of the disease included in the combination which is not an adverse event.

A specific example of pattern attribute data will be described. A period of a total of seven months with a reference time as the center is assumed for a certain patient, and whether hospitalization occurs or not is indicated by "0" (non-occurrence of hospitalization) and "1" (occurrence of hospitalization) for each month of the period. Then, if the patient is hospitalized at least once during the seven months, there are 127 ($=2^7-1$) patterns that are represented by a combination of "0" and "1" in total. Therefore, each of the 127 patterns is regarded as an attribute item, and the rate of occurrence of each pattern can be a value of the attribute item.

(Rate of Occurrence)

The second kind of attribute data is occurrence rate attribute data. As shown in FIG. 3, this attribute data is attribute data indicating, for a combination of a drug and a disease, the rate of occurrence of predetermined kinds of medical event during a period until occurrence of the disease after prescription of the drug in the case where the disease occurs within a first period with a predetermined length after the drug is prescribed for the same patient.

This attribute data is created based on the idea that some difference will appear in the rate of occurrence of medical events such as high medical expenses and hospitalization during a period until a disease occurs after a drug included in a combination is prescribed, between the case where an adverse event occurs and the case where an adverse event does not occur.

For example, during a period from a time point when a drug included in a combination indicating an adverse event is prescribed until a time point when a disease occurs, such a case is conceivable that the patient complains about bad condition of his or her body because of prescription of the drug, and various medical acts are performed at the same time to examine the body condition of the patient when he receives a medical examination by a doctor, so that an event of the number of simultaneous medical acts (10 or more) occurs. Therefore, it can be thought that the rate of occurrence of the medical event of the number of simultaneous medical acts (10 or more) is high. On the other hand, during a period from a time point when a drug included in a combination which is not an adverse event is prescribed until a time point when a disease occurs, it does not happen that the patient complains about bad condition of his or her body because of prescription of the drug and receives a medical examination by a doctor. Therefore, it can be thought that the rate of occurrence of the medical event of the number of simultaneous medical acts (10 or more) is low.

(Transition Probability)

Figure 4:
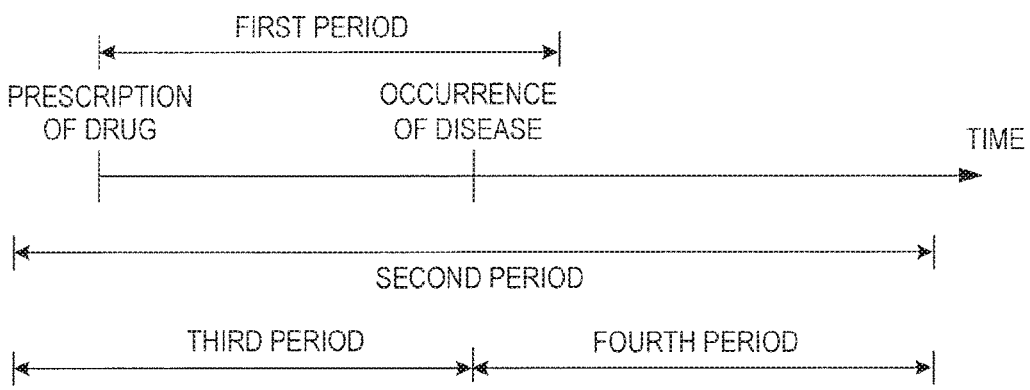
FIG. 4 is a diagram showing relationships among first to fourth periods.

The third kind of attribute data is transition probability attribute data. As shown in FIG. 4, this attribute data is attribute data indicating, for a combination of a drug and a disease, transition probability of occurrence or non-occurrence of predetermined kinds of medical events during a predetermined third period before occurrence of the disease and a predetermined fourth period after the occurrence, with the time point of the occurrence as a reference, in the case where the disease occurs within a first period with a predetermined length after the drug is prescribed for the same patient.

This attribute data is created based on the idea that some difference will appear in order of occurrence and non-occurrence of medical events such as high medical expenses and hospitalization during periods before and after occurrence of a disease included in a combination, between the case where an adverse event occurs and the case where an adverse event does not occur.

For example, it can be thought that the probability of transition of the medical event of high medical expenses from non-occurrence to occurrence becomes high, as in the case where high medical expenses do not occur during a period before occurrence of a disease included in a combination indicating an adverse event, while high medical expenses occur after occurrence of the disease because of treatment of the adverse event. On the other hand, it can be thought that, during periods before and after occurrence of a disease included in a combination which is not an adverse event, high medical expenses occur during neither of periods, and therefore, that the probability of the medical event of high medical expenses transitioning from non-occurrence to non-occurrence becomes high.

(Difference Between Event Occurrence Rates)

The fourth kind of attribute data is event occurrence rate difference attribute data. This attribute data is such attribute data as described below. For a combination of a drug and a disease, with the use of a first occurrence rate of predetermined kinds of medical events within a predetermined third period before a time point of occurrence of the disease as a reference in the case where the disease occurs during a first period with a predetermined length after the drug is prescribed for the same patient, and a second occurrence rate of predetermined kinds of medical events during a predetermined fourth period after that, a null hypothesis that there is not a difference between the first occurrence rate and the second occurrence rate and an alternative hypothesis that there is a difference are made, and difference between the rates of the two groups is examined. The fourth kind of attribute data is attribute data indicating a p value indicating the probability of the null hypothesis being rejected when the null hypothesis is correct.

This attribute is created based on the idea that some difference appears in the rate of occurrence of medical events such as high medical expenses and hospitalization during periods before and after occurrence of a disease included in a combination, between the case where an adverse event occurs and the case where an adverse event does not occur.

For example, since it can be thought that, though the probability of occurrence of high medical expenses is low during a period before occurrence of a disease included in a combination indicating an adverse event, the probability of occurrence of high medical expenses is high during a period after occurrence of the disease because of treatment of the adverse event, it can be thought that there is a difference in the rate of occurrence before and after occurrence of the disease, and the p value becomes small. On the other hand, since it can be thought that, during periods before and after occurrence of a disease included in a combination which is not an adverse event, the probability of occurrence of high medical expenses is low in both of the periods, it can be thought that there is not a difference in the rate of occurrence before and after occurrence of the disease, and the p value becomes large.

(Abnormal Value)

The fifth kind of attribute data is abnormal value attribute data. This attribute data is such attribute data as described below. For the drug and disease of each inputted combination, with the use of a first medical event pattern set obtained by collecting results of extracting patterns indicating order of occurrence and non-occurrence of predetermined kinds of medical events within a predetermined second period before and after a time point when the drug is prescribed for the same patient as a reference point, and a second medical event pattern set obtained by, in the case where the disease occurs within a first period with a predetermined length after the drug is prescribed for the same patient, collecting results of extracting patterns indicating order of occurrence and non-occurrence of predetermined kinds of medical events within a predetermined second period before and after the time point when the disease occurs as a reference, a pattern of medical events is learned with a probability model using the first medical event pattern set. A numerical value indicating how abnormal each pattern included in the second medical event pattern set is as a pattern generated from the learned probability model is caused to be the attribute data.

As for this attribute, it can be thought that some difference will appear in order of occurrence and non-occurrence of medical events, such as high medical expenses and hospitalization, during periods before and after occurrence of a disease included in a combination, between the case where an adverse event occurs and the case where an adverse event does not occur.

Furthermore, it is originally rare that an adverse event occurs because of prescription of a drug. It can be thought that, in most cases, an adverse event does not occur even if a drug is prescribed. Therefore, it can be thought that, if the medical event occurrence pattern at the timing of a drug being prescribed for a patient is learned by a probability model irrespective of whether an adverse event occurs or not, a medical event occurrence pattern at a timing when an adverse event occurs after the drug is prescribed for the patient shows an occurrence pattern which extremely rarely occurs.

Therefore, it can be thought that, by learning the medical event occurrence pattern at the timing of a drug being prescribed for a patient by a probability model and causing a numerical value indicating a degree of abnormality as a pattern generated from the learned probability model to be attribute data, difference will appear in the attribute data between the case where an adverse event occurs and the case where an adverse event does not occur.

For example, it can be thought that, when a drug is prescribed and an adverse event occurs, a pattern that high medical expenses occur at every time point in succession accompanying treatment of the adverse event. On the other hand, it can be thought that such a pattern that high medical expenses occur at every time point in succession does not easily occur in time-series information about the medical event at the timing of a drug being prescribed for a patient.

As the probability model, for example, a Markov probability model can be used. In this case, by treating a medical event occurrence pattern as a Markov process and inputting the Markov process into a learned Markov probability model, attribute data is calculated. Otherwise, a naive Bayesian model can be used as the probability model.

(Outlier)

The sixth kind of attribute data is outlier attribute data. This attribute data is attribute data indicating, when the above-described pattern attribute data about the drug and disease of each inputted combination is used to compare the pattern attribute data of each combination with pattern attribute data of other inputted combinations, a deviation degree of magnitude tendency of the value of each attribute item of the pattern attribute data of each combination.

This attribute is created based on the idea that, because an adverse event is an event that occurs rarely and many of combinations are combinations that do not indicate adverse events, and because, in the magnitude tendency of the value of each attribute item of pattern attribute data, combinations not indicating adverse events resemble one another but do not resemble combinations indicating adverse events, the magnitude tendency of the value of each attribute item of attribute data of a combination indicating an adverse event, among all the combinations, significantly deviates in comparison with many other combinations.

For example, as for a combination indicating an adverse event, it can be thought that, if the drug is prescribed and the disease occurs, the rate of occurrence of the pattern that high medical expenses occur at every time point in succession is high. As for many other combinations not indicating adverse events, however, the rate of occurrence of the pattern that high medical expenses occur at every time point in succession is low. Therefore, from the viewpoint of the rate of occurrence of the pattern that high medical expenses occur at every time point in succession, it can be thought that a combination indicating an adverse event deviates in comparison with the other combinations.

A technique of calculating a degree of deviation from others is used to create the attribute data. Techniques related thereto are known as outlier detection techniques. It is a 1-class support vector machine (one-class SVM) that is known as one of general techniques among the techniques. The 1-class support vector machine is a technique in which a discriminant model is learned so that data distributed at a high density among inputted data is discriminated as a positive example, and a positive value is outputted while data other than the data is discriminated as a negative example, and a negative value is outputted; and, when data distributed at a low density (that is, data deviating from the other inputted data) is inputted with the use of the learned discriminant model, a negative value is outputted.

As attribute data other than the six kinds described above, attribute data of various modifications exist. The attribute data of the modifications will be described below.

(Indicator Function)

The attribute data of the modifications include, for example, indicator function attribute data. This attribute data is attribute data indicating, for the drug and disease of each inputted combination, which ICD10 code the disease belongs to.

This attribute is created base on the idea that a disease belonging to the same ICD10 code as a disease included in a combination indicating an adverse event is similarly an adverse event. Since ICD10 codes are codes for classifying diseases, it can be thought that, if diseases have the same ICD10 codes, the types of the diseases resemble each other. Therefore, it can be thought that, if a certain disease is an adverse event of a drug, other diseases having the same ICD10 code indicate adverse events of the same drug.

A specific method for creating the indicator function attribute data will be described. From all kinds of drugs and disease names included in positive examples, negative examples and combinations which are neither positive examples nor negative examples read from storage device 12, a list of kinds of unique drugs and a list of kinds of unique disease names are created.

Further, each of the disease names included in the list of kinds of unique disease names is converted to the ICD10 unit with the use of the table of conversion to ICD10. Furthermore, a list showing the kinds of unique ICD10 among them is created. Then, a list showing all combinations of drug and ICD10 is newly created with the use of the list of kinds of unique drugs and the list of kinds of unique ICD10. For example, if the number of kinds of drugs is 10, and the number of kinds of ICD10 is 100, then the list shows 1000 combinations of drug and ICD10.

Then, for each of combinations of "drug and disease" which are positive examples, negative examples or those that are neither positive nor negative examples, the disease included in the combination is converted to the ICD10 unit with the use of the table of conversion to ICD10 codes first, with each of the combinations written in the list as an attribute item. If the combination of the drug and ICD10 included in the combination corresponds to a combination of drug and ICD10 shown by an attribute item, the value of "1" is set as the value of the attribute item. Otherwise, the value of "0" is set as the value of the attribute item.

The various attribute data which can be used in the present exemplary embodiment has been described above. However, as the attribute data, those other than the attribute data given here can be also used. Further, in the present exemplary embodiment, it is recommended to change the kinds of predetermined medical events and similarly create the above-described attribute data. As the kinds of medical events, for example, hospitalization, medical expenses (four or more digits), medical expenses (three or more digits), simultaneous medical acts (20 or more kinds), simultaneous medical acts (10 or more kinds), simultaneous medical acts (7 or more kinds), simultaneous medical acts (5 or more kinds), the number of combined drugs (20 or more kinds), the number of combined drugs (10 or more kinds), the number of combined drugs (7 or more kinds), the number of combined drugs (5 or more kinds), disease-related medical events after conversion to the ICD10 unit, disease-related medical events after conversion to the ATC unit, and the like.

Further, the above-described attribute data may be similarly created according to gender or age of a patient. For example, the rate of occurrence of a hospitalization event of a male patient in his twenties can be attribute data. This corresponds to determining attribute data indicating the rate of occurrence of a predetermined kind of medical event during a period until a disease occurs after prescription of a drug in the case where the disease occurs within a first period with a predetermined length after the drug is prescribed for the same male patient in his twenties.

Further, at the time of determining attribute data about a combination of "drug and disease", the attribute data may be created in consideration of only the first prescription, with regard to prescription of the drug. Further, there may be a case where diseases occur at a plurality of points of time during a first period after prescription of the drug. In this case, such a limitation may be applied that the attribute data is created with only the first disease as a reference. Otherwise, attribute data may be created, with each of the second and succeeding diseases as a reference point, without limiting the reference point only to the first prescription. Otherwise, a condition limiting prescription of the drug and a condition limiting a disease to be a reference point may be combined.

(2) Details of Learning Phase S2

(2-1) Step S21

At step S21, positive example combinations 52, negative example combinations 53, positive/negative example flags 55 and attribute data 56 corresponding to the positive and negative examples are read out from storage device 12. It is assumed that N positive and negative example combinations are read out, and each combination is referred to as a combination number n (n=1, . . . , N). Further, an adverse event flag is indicated by $Y_n$ (n=1, . . . , N). That is, $Y_n$ is a flag indicating whether combination n is a positive example combination ($Y_n$=1) or a negative example combination ($Y_n=-1$). Further, the read-out attribute data is indicated by $X_n$ (n=1, 2, ..., N). As described above, $X_n$ is attribute data corresponding to combination n.

(2-2) Step S22

In the present exemplary embodiment, a value to be determined by inputting data to a discriminant model is adverse event score $S(X_n)$. At step S22, the discriminant model for calculating the value is specified, and parameters thereof are learned. Adverse event score $S(X_n)$ indicates strength of suspicion of an adverse event against combination n. Hereinafter, the operation of learning the discriminant model for calculating adverse event score $S(X_n)$ will be described.

As the discriminant model, it is recommended to use, for example, a linear support vector machine (hereinafter referred to as a linear SVM) capable of, when attribute data $X_n$ corresponding to a positive example combination with the positive/negative example flag $Y_n=1$ is given, outputting a score indicating strength of possibility of $Y_n=1$ for certain X. The linear SVM is a model which is often applied to a binary discrimination problem for discriminating whether $Y_n=1$ or $Y_n=-1$ from X. Further, other discriminant models such as a logistic regression model may be used.

The operation of learning the discriminant model will be described with the linear SVM as an example.

In the linear SVM, the following linear discriminant function is used, which discriminates between a positive example and a negative example by outputting a positive value to attribute data of a positive example combination and outputting a negative value to attribute data of a negative example combination when a weight vector W is an M-dimensional weight vector.

$$f(X_n, W) = W^T X_n \quad (1)$$

wherein the superscript "T" indicates transposition of the vector.

When ($X_n$, $Y_n$), (n=1, ..., N) related to positive and negative example combinations are given as learning data for the discriminant model, the value of weight vector W is calculated by minimizing the following objective function in the linear SVM.

$$L(W) = C \sum_{n=1}^{N} \left( (\max(0, 1 - Y_n W^T X_n))^2 \right) + |W| \quad (2)$$

The first term on the right side indicates the sum of discrimination errors. When the signs of $Y_n$ and $W^T X_n$ correspond to each other, the error is zero. When the signs do not correspond to each other, however, the first term on the right side increases by an amount corresponding to the error. The second term on the right side indicates a penalty term, and |W| indicates the norm of W. In general, norm 2 or norm 1 is used. Parameter C is a parameter which adjusts balance between the first term (by reducing error of discrimination between a positive example and a negative example) and the second term (a penalty term). Parameter C may be given in advance as one of control parameters 69. Otherwise, a plurality of candidates for parameter C may be given so that an optimum C may be automatically selected with the use of a cross-validation method.

The value of a parameter which minimizes L(W) is indicated by W*, and parameters of the discriminant model are assumed to be W*. As a method for determining W which minimizes L(W), various optimization techniques are proposed. For example, a method described in [NPL2] and the like exist.

The discriminant model, which is a processing result of learning phase S2, is expressed (defined) by the above learned model parameters W*.

(3) Details of Adverse Event Score Calculation Phase S3

(3-1) Step S31

At step S31, learned discriminant model 57, combinations other than positive and negative examples 54 and attribute data corresponding to the combinations are read out from storage device 12. It is assumed that K combinations other than positive and negative examples and K pieces of attribute data corresponding to the combinations are read out. Here, the read-out attribute data is indicated by $X_k$ (k=1, 2, ..., N).

(3-2) Step S32

At step S32, adverse event score $S(X_k)$ of $X_k$ is calculated by called discriminant model W*. Specifically, adverse event score $S(X_k)$ is calculated as follows:

$$S(X_k) = W^{*T} X_k \quad (3)$$

Calculated adverse event score $S(X_k)$ is stored into storage device 12.

(4) Details of Extraction Phase S4

(4-1) Step S41

At step S41, the K combinations other than positive and negative examples, adverse event score $S(X_k)$ (k=1, K) corresponding to the combinations and an extraction condition are read out from storage device 12. Here, for example, the maximum number of combinations to be extracted or a threshold for the adverse event score is used as the extraction condition.

(4-2) Step S42

If the maximum number H of combinations to be extracted is used as the extraction condition, the combinations are sorted according to the adverse event score, and H combinations are extracted in descending order of adverse event scores. Further, if a threshold T for the adverse event score is used as the condition, the combinations are sorted by the adverse event score, and combinations having an adverse event score with a value equal to or larger than T are extracted in descending order.

(4-3) Step S43

At step S43, a list of combinations strongly suspected to be adverse events, which is an extraction result of extraction at step S42, is stored into storage device 12. Otherwise, the extraction result is outputted to screen display unit 15 or to the outside via communication interface unit 13.

Thus, according to the present exemplary embodiment, it is possible to, on the basis of medical information data, extract a combination of an adverse event from among combinations other than positive and negative examples based on adverse event scores indicating suspicion as an adverse event so that an extraction condition is satisfied.

In the present exemplary embodiment, at the time of determining attribute data from time-series information about medical events within a predetermined period, targeting combinations of "drug and disease", those include a drug having been prescribed for a patient and a disease having been observed in the patient as well as at least one of a medical act performed for the patient and an event showing that the medical act has been performed, accompanying the medical act, are used as the medical events. If an adverse event occurs on the patient, the patient sees a doctor at any hospital department to treat it, a medical act is performed to examine/treat it, and the patient is charged for medical expenses for the medical act. Therefore, some difference appears in time-series information about the medical events of medical act, hospitalization, medical expenses and hospital department between the case where an adverse event has occurred and the case where an adverse event has not occurred.

Therefore, even if, for a combination which is an adverse event and a combination which is not an adverse event, attribute data about the number of times that a disease occurs during a drug prescription period have the same content, it becomes possible to prevent attribute data about the combination which is an adverse event and the combination which is not an adverse event from having the same content by creating various kinds of attribute data about occurrence of the medical events of medical act, hospital department, medical expenses and hospitalization/non-hospitalization. As will be apparent from the present exemplary embodiment, according to the present invention, by creating attribute data using at least one more kind of medical information in addition to time-series information about a drug and occurrence of a disease, it becomes possible to widely extract adverse events with fewer mistakes in comparison with the case of creating attribute data using only a drug and occurrence of a disease.

In the drug adverse event extraction apparatus of the present exemplary embodiment described above, each of input unit 21, attribute data creation unit 22, discriminant model learning unit 23, adverse event score calculation unit 24 and extraction unit 25 provided in processing apparatus 11 can be configured as dedicated hardware. Otherwise, the whole processing apparatus 11 can be configured with a computer provided with a microprocessor such as a CPU (central processing unit) and its peripheral circuits. If processing apparatus 11 is realized by the computer, the computer can be caused to read and execute a program for executing the functions of input unit 21, attribute data creation unit 22, discriminant model learning unit 23, adverse event score calculation unit 24 and extraction unit 25 described above. The program is read from an external apparatus via communication interface unit 13 and the like or read from a computer-readable storage medium and stored into storage device 12 or a memory for the program provided separately from storage device 12 in advance. Furthermore, all or a part of creation of attribute data, learning of a discriminant model, calculation of adverse event scores and extraction of combinations corresponding to or indicating adverse events may be distributed to and executed by a plurality of processors.

An exemplary embodiment has been described above. The present invention, however, is not limited to the above exemplary embodiment, and various kinds of additions and changes are possible. Various modifications of the exemplary embodiment described above will be described below. In a drug adverse event extraction apparatus according to each modification also, processing apparatus 11 can be realized by causing a computer to read and execute a corresponding program.

[Modification 1]

Figure 5:
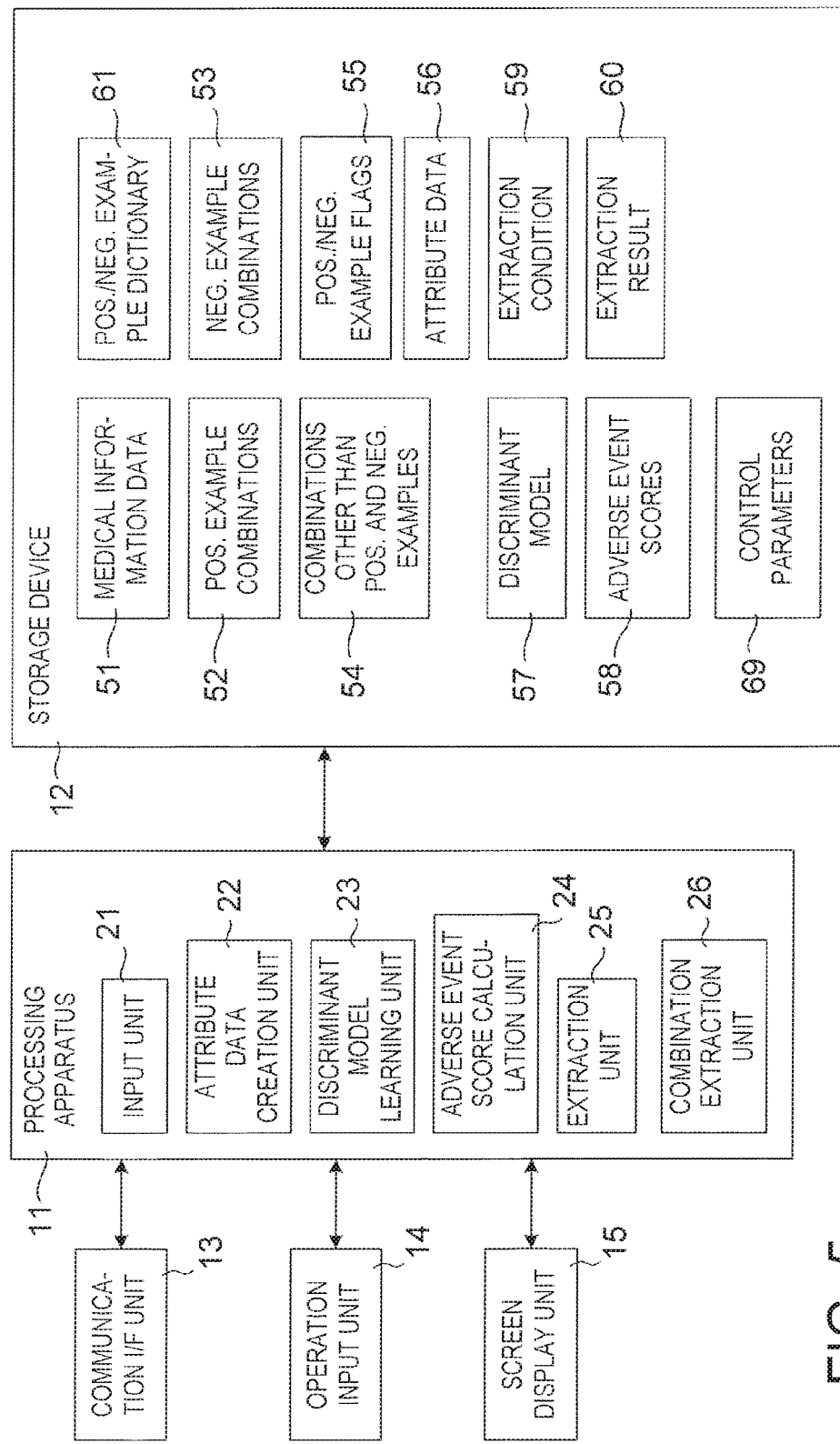
FIG. 5 is a block diagram showing a configuration of a drug adverse event extraction apparatus according to Modification 1.

FIG. 5 shows a configuration of a drug adverse event extraction apparatus according to Modification 1. In the drug adverse event extraction apparatus shown in FIG. 1, it is necessary to input three kinds of positive example combinations, negative example combinations and combinations other than positive and negative examples in advance. By the way, time-series information about medical events for each patient included in medical information data 51 also includes time-series information about drug prescription and time-series information about which disease occurred when. Therefore, if there is some mechanism for classifying the positive examples, the negative examples and the combinations other than positive and negative examples, extraction of drug adverse information events must be performed without inputting the three kinds of the positive example combinations, negative example combinations and the combinations other than positive and negative examples in advance. Therefore, what is shown in FIG. 4 is such that, in the apparatus shown in FIG. 1, positive/negative example dictionary 61 in which, for each combination of "drug and disease", whether the combination is to be classified as a positive example or a negative example is written is arranged in storage device 12, and combination extraction unit 26 that extracts a combination of "drug and disease" from time-series information about medical events for each patient included in medical information data 51 and automatically performs classification about whether the extracted combination is a positive example, a negative example or a combination other than positive and negative examples based on positive/negative example dictionary 61 is provided in processing apparatus 11. Combination extraction unit 26 corresponds to combination extracting means.

Figure 6:
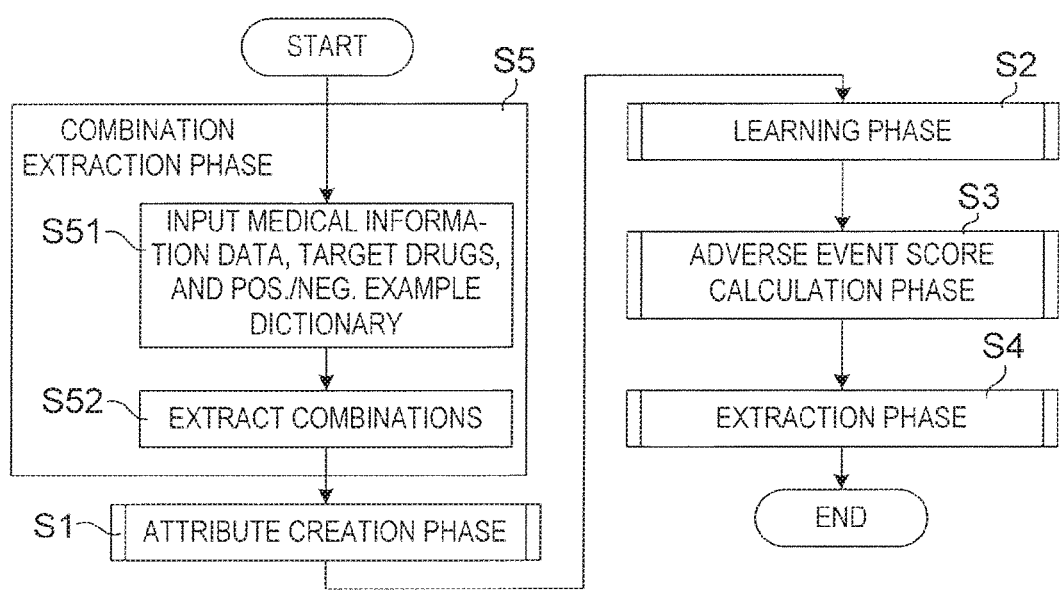
FIG. 6 is a flowchart showing the operation of the drug adverse event extraction apparatus shown in FIG. 5.

FIG. 6 shows the operation of the drug adverse event extraction apparatus of Modification 1 shown in FIG. 6. In this apparatus, before attribute data creation phase S1 in the operation shown in FIG. 2, combination extraction phase S5 is provided at which combinations of "drug and disease" are extracted from medical information data, and the extracted combinations are classified into positive example combinations, negative example combinations and combinations other than positive and negative examples with reference to positive/negative example dictionary 61.

At combination extraction phase S5, input unit 21 first receives medical information data, target drugs and the positive/negative example dictionary and stores them into storage device 12 at step S51. Next, at step S52, combination extraction unit 26 extracts a combination from medical information data 51. At that time, combination extraction unit 26 refers to the period length condition included in control parameters 69, and, if, for example, a certain patient has a disease which occurred during the first period (see FIG. 3) after prescription of a certain drug, extracts the combination of the drug and the disease as a target. Then, combination extraction unit 26 judges whether the extracted combination is a positive example or a negative example with reference to positive/negative example dictionary 61, stores the combination into storage device 12 as a positive example combination if the combination is a positive example, stores the combination into storage device 12 as a negative example combination if the combination is a negative example, and, in other cases, stores the combination into storage device 12 as a combination other than positive and negative examples.

Figure 2:
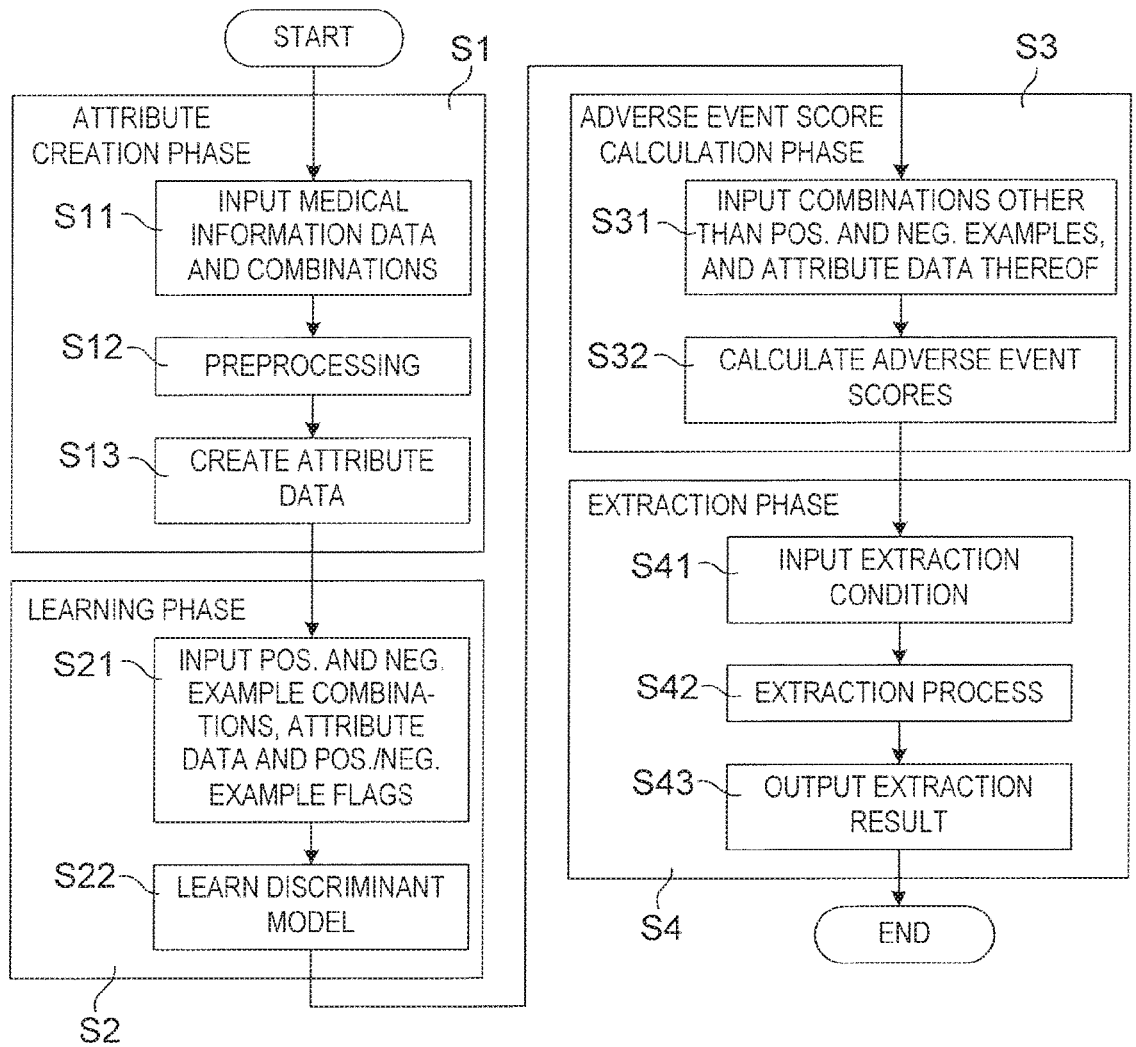
FIG. 2 is a flowchart showing the operation of the drug adverse event extraction apparatus shown in FIG. 1.

After step S52 ends, attribute data creation phase S1, learning phase S2, adverse event score calculation phase S3 and extraction phase S4 are sequentially executed similarly to the case shown in FIG. 2.

[Modification 2]

Figure 7:
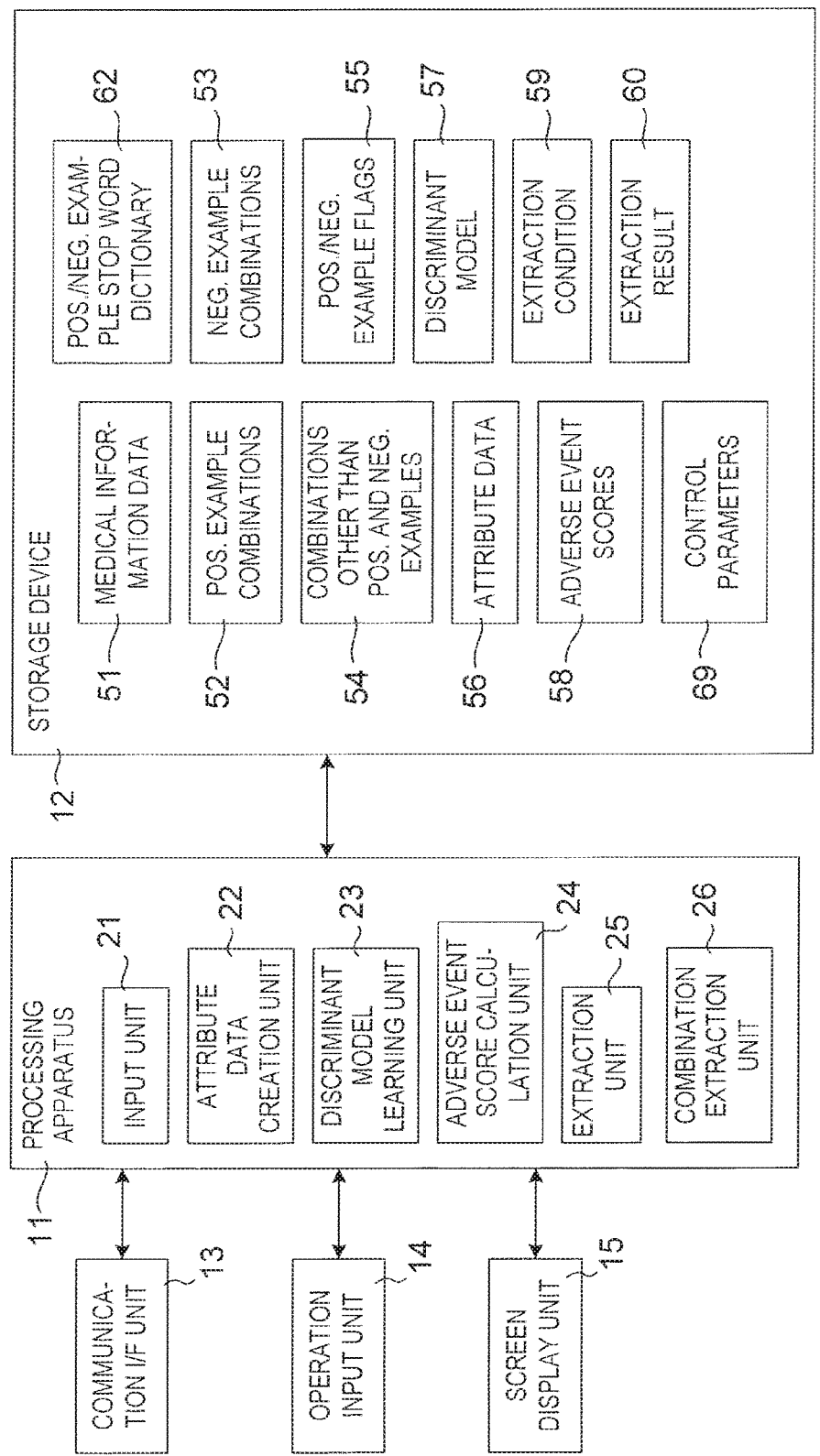
FIG. 7 is a block diagram showing a configuration of a drug adverse event extraction apparatus according to Modification 2.

FIG. 7 shows a configuration of a drug adverse event extraction apparatus according to Modification 2. In extraction of drug adverse events, there may be a disease which is thought not to be related to a certain drug at all. When attempting to extract adverse events, targeting combinations of "drug and disease" including such a disease, there is a possibility that operation time is increased or accuracy degradation is caused. Therefore, the drug adverse event extraction apparatus shown in FIG. 7 is such that positive/negative example stop word dictionary 62 is stored in storage device 12 instead of the positive/negative example dictionary in the apparatus shown in FIG. 5. In what is shown in FIG. 7, positive/negative example stop word dictionary 62 is such that a list of diseases not to be thought as being included in processing target combinations is further stored as a list of stop words in positive/negative example dictionary 61 in Modification 1. In Modification 2, by using positive/negative example stop word dictionary 62, use of a combination which includes a disease corresponding to a stop word is prevented.

Figure 8:
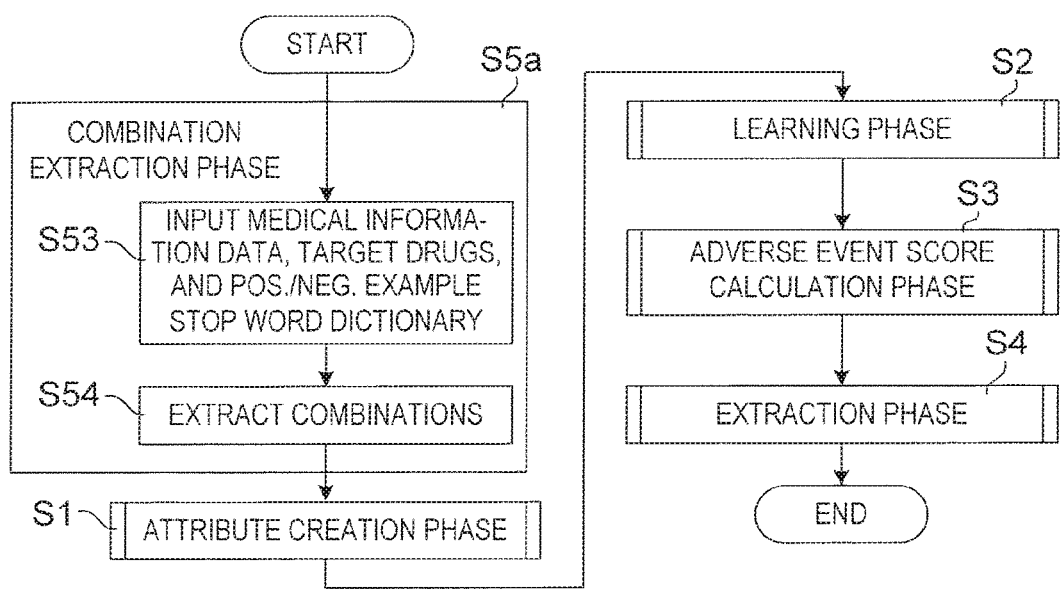
FIG. 8 is a flowchart showing the operation of the drug adverse event extraction apparatus shown in FIG. 7.

FIG. 8 shows the operation of the drug adverse event extraction apparatus of Modification 2 shown in FIG. 7. In the operation in Modification 2, combination extraction phase S5a is provided at which, by referring to positive/negative example stop word dictionary 62, unnecessary combinations are removed from among combinations of "drug and disease" extracted from medical information data, and the remaining combinations are extracted as positive examples or negative examples, instead of combination extraction phase S5 in the operation of Modification 1 shown in FIG. 5. At combination extraction phase S5a, input unit 21 first receives medical information data, target drugs, a period length condition and the positive/negative example stop word dictionary and stores them into storage device 12 at step S53. Next, at step S54, combination extraction unit 26 extracts a combination from medical information data 51. At that time, combination extraction unit 26 refers to the period length condition included in control parameters 69, and, if, for example, a certain patient has a disease which occurred during the first period (see FIG. 3) after prescription of a certain drug, extracts the combination of the drug and the disease as a target. Then, combination extraction unit 26 judges whether the extracted combination is a stop word or not with reference to positive/negative example stop word dictionary 62 first. If the combination is a stop word, combination extraction unit 26 excludes the combination, and, for each of the remaining combinations, judges whether the combination is a positive example or a negative example with reference to positive/negative example stop word dictionary 62. In the case of a positive example, the combination is stored into storage device 12 as a positive example combination. In the case of a negative example, the combination is stored into storage device 12 as a negative example combination. In other cases, the combination is stored into storage device 12 as a combination other than positive and negative examples.

After step S54 ends, attribute data creation phase S1, learning phase S2, adverse event score calculation phase S3 and extraction phase S4 are sequentially executed similarly to the case shown in FIG. 2.

[Modification 3]

Figure 9:
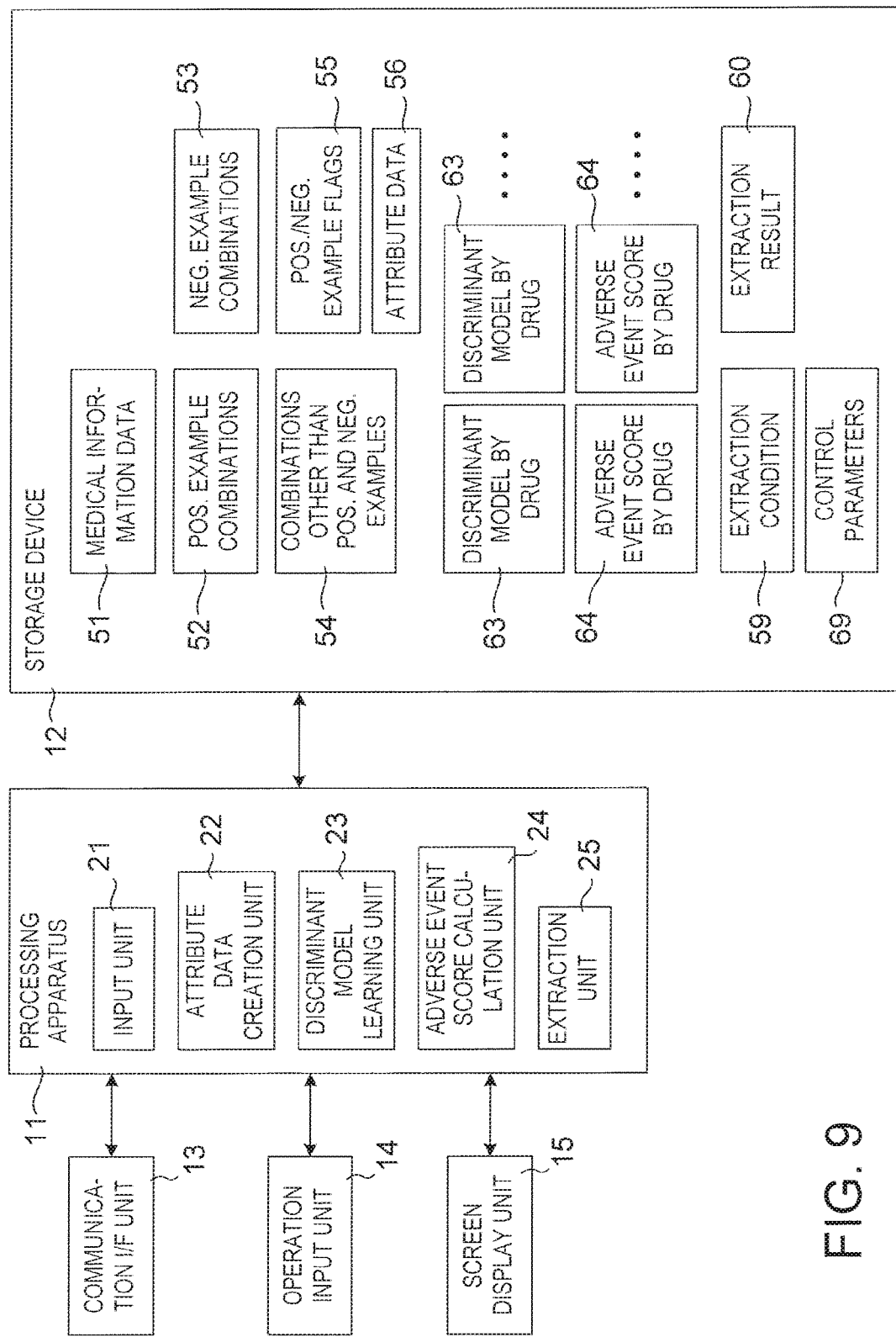
FIG. 9 is a block diagram showing a configuration of a drug adverse event extraction apparatus according to Modification 3.

FIG. 9 shows a configuration of a drug adverse event extraction apparatus according to Modification 3. In the examples described so far, a single discriminant model is used for a plurality of kinds of drugs. In Modification 3, however, a different discriminant model is used for each kind of drug. Therefore, a plurality of discriminant models by drug 63 and a plurality of adverse event scores by drug 64 are stored in storage device 12 instead of discriminant model 57 and adverse event scores 58 in the apparatus shown in FIG. 1.

Figure 10:
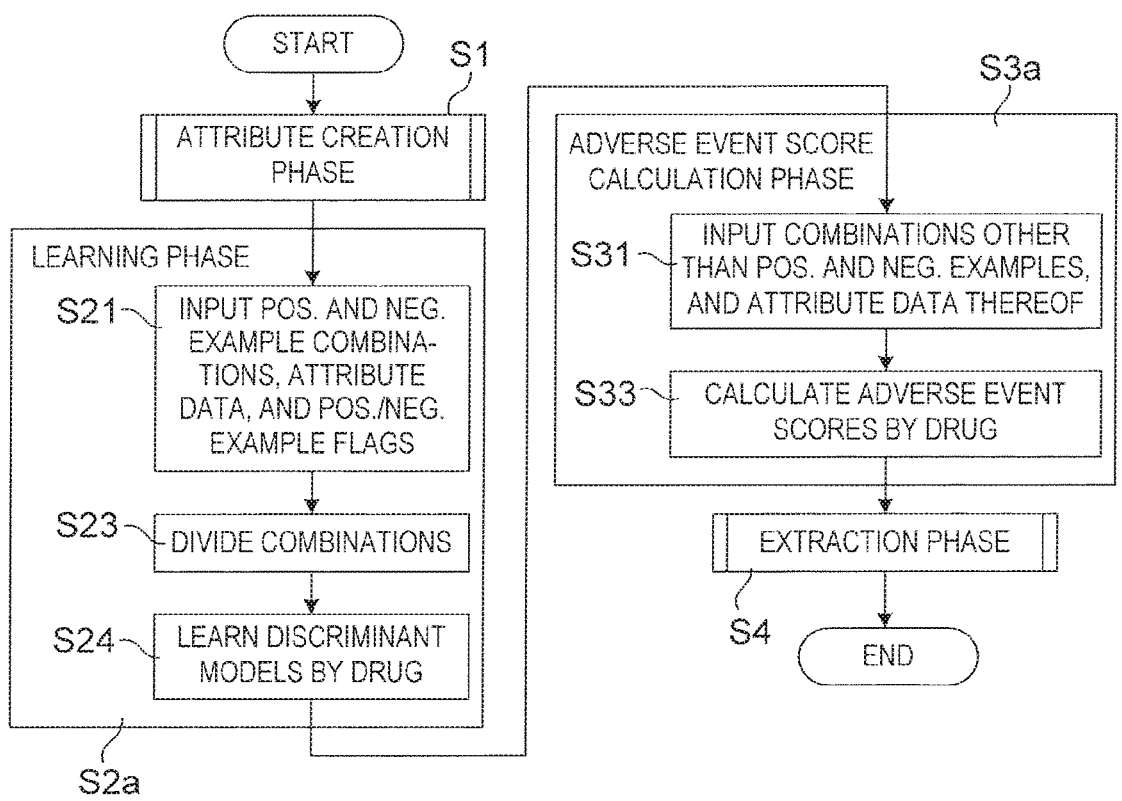
FIG. 10 is a flowchart showing the operation of the drug adverse event extraction apparatus shown in FIG. 9.

FIG. 10 shows the operation of the drug adverse event extraction apparatus of Modification 3 shown in FIG. 9. In the operation in Modification 3, instead of learning phase S2 and adverse event score calculation phase S3 in the operation shown in FIG. 2, learning phase S2a and adverse event score calculation phase S3a are provided, respectively. At learning phase S2a, after step S21 of learning phase S2 in FIG. 2 (however, discriminant models by drug 63 are called instead of discriminant model 57) is performed, discriminant model learning unit 23 divides positive example combinations and negative example combinations according to the kinds of drugs at step S23. Then, at step 24, according to the kinds of drugs, discriminant model learning unit 23 learns corresponding discriminant models by drug 63 and stores results into storage device 12. Further, at adverse event score calculation phase S3a, after step S31 of adverse event score calculation phase S3 in FIG. 2 is executed, adverse event score calculation unit 24 applies attribute data to corresponding discriminant models by drug 63 according to the kinds of drugs and calculates adverse event scores by drug. The calculated adverse event scores by drug are stored into storage device 12.

Further, in Modification 3, a multi-task learning technique of learning discriminant models by drug not separately but simultaneously may be adopted at learning phase S2a. The multi-task learning technique is a learning technique for simultaneously learning a plurality of related models (in the present exemplary embodiment, discriminant models), and it is known that it may be possible to learn models so that the performance of each model becomes higher (with regard to the present exemplary embodiment, the performance of each discriminant model discriminating between positive and negative examples becomes higher) than learning the models separately. A representative example of the multi-task learning technique is described in [NPL3]. There are various kinds of multi-task learning techniques. Trace-norm regularized multi-task learning, which is one of the most common methods among them, may be used. This method is a method for learning model parameters of each of a plurality of models so that the model parameters exist in a low-dimensional space common to the plurality of models.

Furthermore, it is known that, in the multi-task learning technique, if there is somewhat strong relation among models (in this exemplary embodiment, discriminant models) to be simultaneously learned, the models can be learned so that the performance of each of the models (in the example of the present exemplary embodiment, the performance of each discriminant model discriminating between positive and negative examples) becomes higher. Therefore, in the present exemplary embodiment, it is recommended not to adopt the multi-task learning technique for learning of all the discriminant models by drug but to adopt the multi-task learning technique for each group of discriminant models by drug related to drugs with the same efficacy. It can be thought that, by doing so, a more advantageous effect of adopting the multi-task technique is obtained. This is because it can be thought that, if drugs have the same efficacy, the kinds of adverse events caused by prescription of the drugs resemble one another.

Furthermore, in Modification 3, a positive/negative example dictionary may be provided so that positive example combinations and negative example combinations are automatically extracted, similarly to Modification 1. A positive/negative example stop word dictionary similar to that of Modification 2 may be provided so that unnecessary combinations are not used while positive example combinations and negative example combinations are automatically extracted.

[Modification 3-1]

In Modification 3, a different discriminant model is used for each kind of drug. As a variation thereof, a different discriminant model is used for each efficacy in Modification 3-1. That is, a single discriminant model is used for a plurality of drugs having the same efficacy. This Modification 3-1 corresponds to such that uses not brands of drugs but "efficacies of drugs" as "the kinds of drugs". Therefore, a plurality of discriminant models by efficacy and a plurality of adverse event scores by efficacy are stored in storage device 12 instead of the plurality of discriminant models by drug 63 and the plurality of adverse event scores by drug 64 in the apparatus shown in FIG. 9.

The operation of the drug adverse event extraction apparatus of Modification 3-1 is similar to the operation in Modification 3 shown in FIG. 10. However, learning of discriminant models by efficacy is performed instead of learning of discriminant models by drug at step S24, and calculation of adverse event scores by efficacy is performed instead of calculation of adverse event scores by drug at step S33.

[Modification 3-2]

In the examples described so far, positive and negative example combinations are learned with discriminant models irrespective of the frequency of the positive and negative example combinations on medical information data. In Modification 3-2, however, positive and negative example combinations that appear with a high frequency and positive and negative example combinations that appear with a low frequency are learned with separate discriminant models. Therefore, discriminant models by high/low frequency and adverse event scores by high/low frequency are stored in storage device 12 instead of the plurality of discriminant models by drugs 63 and the plurality of adverse event scores by drug 64 in the apparatus shown in FIG. 9.

In the case of learning discriminant models for discriminating positive examples and negative examples having a common characteristic in terms of co-occurrence frequency, the performance of discriminating between a positive example and a negative example is thought to become higher by separately treating combinations of such a drug and a disease that co-occur frequently and combinations of such a drug and a disease that co-occur only rarely as shown in Modification 3-2 in comparison with extracting adverse events from a mixture of combinations of such a drug and a disease that co-occur frequently and combinations of such a drug and a disease that co-occur only rarely. For example, since there are various kinds of adverse events from a slight adverse event that frequently occurs to a serious adverse event that rarely occurs, it can be thought that, by learning a discriminant model using positive and negative example combinations of such a drug and a disease that frequently co-occur, such an adverse event that frequently occurs similarly can be detected. On the other hand, it can be thought that, by learning a discriminant model using positive and negative example combinations of such a drug and a disease that rarely co-occur, such an adverse event that rarely occurs can be detected. Thus, by learning discriminant models by high/low frequency, it is expected that the accuracy of detecting adverse events is increased.

The operation of the drug adverse event extraction apparatus in Modification 3-2 is similar to the operation in Modification 3 shown in FIG. 10. However, at the time of dividing combinations at step S23, a certain threshold is set, and the combinations are divided as combinations the frequency of which is equal to or above the threshold and combinations the frequency of which is below the threshold. At step S24, instead of learning discriminant models by drug, corresponding discriminant models by frequency are learned based on whether high frequency or low frequency.

In calculation of adverse event scores by drug at step S33, attribute data is applied to corresponding discriminant models by frequency based on high/low frequency of combinations to calculate adverse event scores by frequency.

As for the frequency threshold used at the learning phase, a plurality of candidates are prepared in advance, and an optimum threshold determined by the cross-validation method can be used.

[Modification 4]

Figure 11:
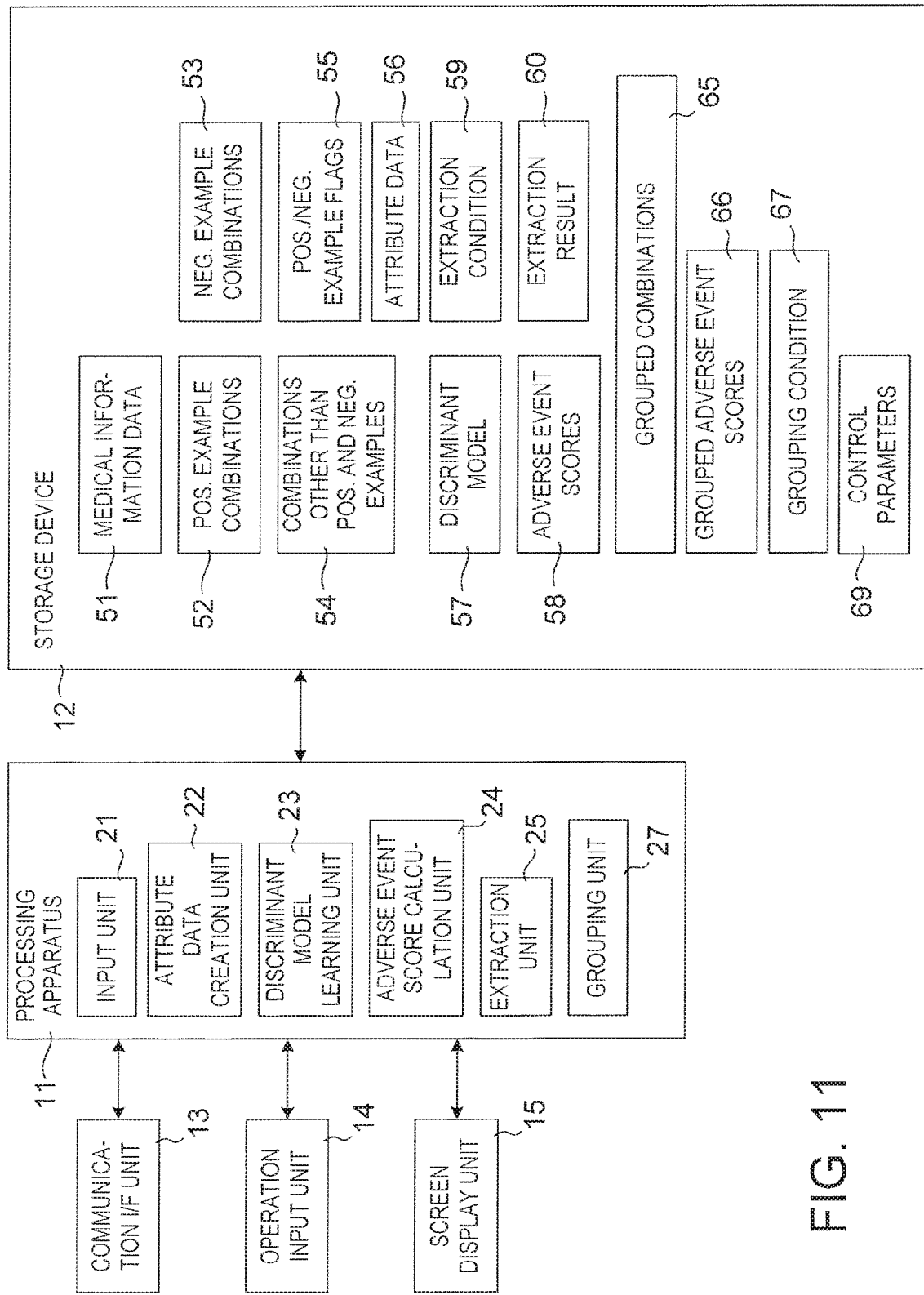
FIG. 11 is a block diagram showing a configuration of a drug adverse event extraction apparatus according to Modification 4.

FIG. 11 shows a configuration of a drug adverse event extraction apparatus according to Modification 4. The apparatus shown in FIG. 11 is such that, in the apparatus shown in FIG. 1, when combinations other than positive and negative examples are extracted and sorted in order of adverse event scores, grouping is performed for the extracted combinations other than positive and negative examples. In comparison with the apparatus shown in FIG. 1, the apparatus shown in FIG. 11 has a configuration in which grouping unit 27 is provided in processing apparatus 11, and grouped combinations 65, grouped adverse event scores 66 and grouping condition 67 are stored in storage device 12. Grouping unit 27 corresponds to grouping means.

For example, even if the score of each combination indicating an adverse event that indicates suspicion as an adverse event is low, the score of a disease group which includes a combination indicating an adverse event becomes relatively high in comparison with other disease groups, by grouping combinations other than positive and negative examples and summing up scores for each disease group; and it can be thought that there is a possibility that the score of the disease group becomes higher. Therefore, in Modification 4, after outputting an adverse event score for each of combinations other than positive and negative examples, the disease names of the combinations are grouped with the use of some reference. Then, the scores of a plurality of combination belonging to the same disease group are summed up to calculate a grouped adverse event score. Then, the grouped combination and the grouped adverse event score are outputted as a set.

Figure 12:
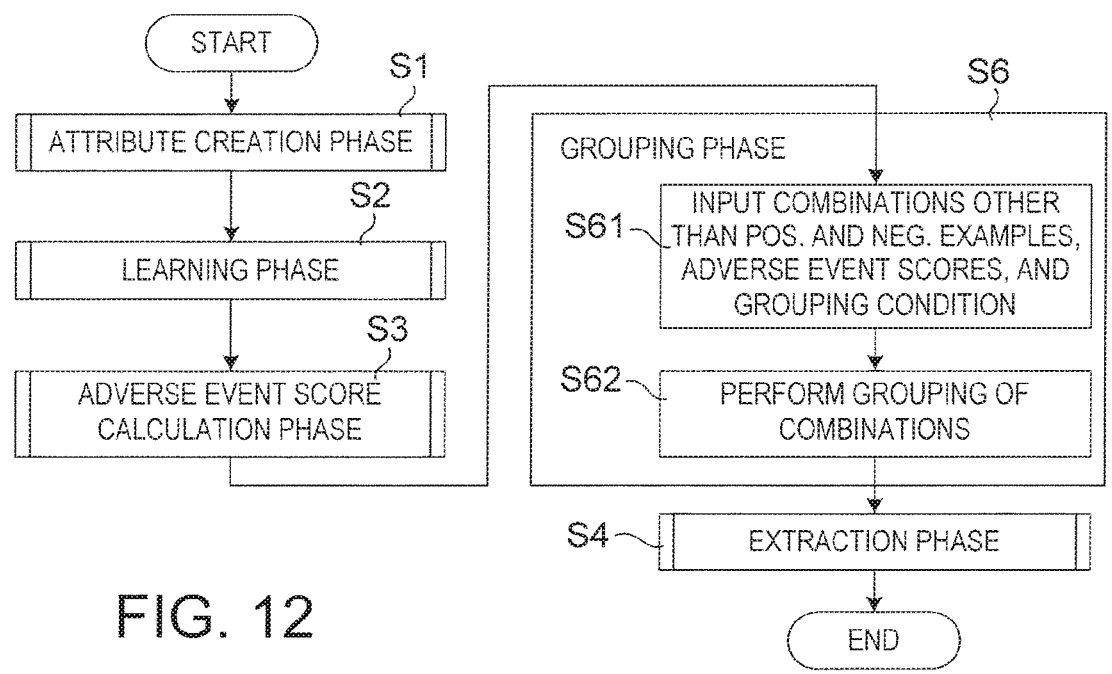
FIG. 12 is a flowchart showing the operation of the drug adverse event extraction apparatus shown in FIG. 11.

FIG. 12 shows the operation of the drug adverse event extraction apparatus of Modification 4 shown in FIG. 11. The operation in Modification 4 is such that grouping phase S6 is provided between adverse event score calculation phase S3 and extraction phase S4 in the operation shown in FIG. 2. At grouping phase S6, grouping unit 27 first reads out combinations other than positive and negative examples 54, adverse event scores 58 and grouping condition 71 from storage device 12 at step S61. At step S62, grouping unit 27 executes grouping of combinations other than positive and negative examples 54, and stores grouped combinations and grouped adverse event scores corresponding to the grouped combinations into storage device 12. At extraction phase S4 following grouping phase S6, combinations suspected to be adverse events are extracted based on grouped combinations 65 and grouped adverse event scores 66.

Further, a positive/negative example dictionary may be provided so that positive example combinations and negative example combinations are automatically extracted, similarly to Modification 1. A positive/negative example stop word dictionary similar to that of Modification 2 may be provided so that unnecessary combinations are not used while positive example combinations and negative example combinations are automatically extracted.

In Modification 4, various conditions are conceivable as a condition for grouping disease names of combinations. For example, disease names of combinations having the same top four digits (detailed classification) of an ICD10 code (a code of ICD (International Statistical Classification of Diseases and Related Health Problems), 10th Edition) may be included in the same disease group.

Further, as a method for summing up the scores of a plurality of combinations included in grouped combinations to calculate a grouped adverse event score, various methods are conceivable. When the method for calculating the grouped adverse event score differs, the tendency of grouped combinations that are easily extracted as those having a high score also differs. Therefore, it is necessary to determine the calculation method according to the purpose of which grouped combination having which nature is to have a high score. Various grouped adverse event score calculation methods and the characteristics thereof will be simply described below.

For example, a method may be adopted in which a mean value of the scores of a plurality of combinations which include diseases belonging to the same ICD10 code (top four digits) is caused to be the grouped adverse event score. By causing the mean value to be the grouped adverse event score, such a group that the scores of combinations belonging to the group are averagely high is extracted as having a high score. Otherwise, in the case where the scores of only a part of combinations are extremely high, the group is extracted as having a high score.

Otherwise, a method may be adopted in which the maximum value among the scores of a plurality of combinations which include diseases belonging to the same ICD10 code (top four digits) is caused to be the grouped adverse event score. By causing the maximum value to be the grouped adverse event score, such a group that includes at least one combination strongly suspected to be an adverse event (having a score with a large value) among combinations belonging to the same group is easily extracted as having a high score.

Otherwise, a method may be adopted in which the median among the scores of a plurality of combinations which include diseases belonging to the same ICD10 code (top four digits) is caused to be the grouped adverse event score. By causing the median to be the grouped adverse event score, such a group that the scores of a plurality of combinations belonging to the same group are high as a whole is extracted as having a high score. In the case where the adverse event scores of only a part of combinations are extremely high, the group is hardly extracted as having a high score.

Otherwise, a method may be adopted in which a value obtained by summing up only positive scores among the scores of a plurality of combinations which include diseases belonging to the same ICD10 code (top four digits) is caused to be the grouped adverse event score. By performing calculation in this way, such a group that a lot of combinations having a positive high score are included in the same group is easily extracted as having a high score.

Furthermore, a method may be adopted in which, after normalizing adverse event scores given to all combinations other than positive examples and negative examples so that the adverse event scores become values within a range of 0 to 1, the total value of the adverse event scores of combinations belonging to the same ICD10 code (top four digits) is caused to be the grouped adverse event score. By taking the total value after normalization, such a disease group that a lot of combinations having a high score are included in the same group, and a large number of combinations is included in the same group is easily extracted as having a high score. Since the grouping process is performed after all the values of ranking scores are normalized to be between 0 and 1, the total value is not reduced even if such a combination that the value of the score before normalization is small (negatively large) exists in the same group. There is a tendency that the grouped adverse event score of such a group that there are a lot of combinations belonging to the same group becomes higher.

Further, a method may be adopted in which, after normalizing adverse event scores given to all combinations other than positive examples and negative examples so that the adverse event scores become values within the range of 0 to 1, the mean value of the adverse event scores of combinations belonging to the same ICD10 code (top four digits) is caused to be the grouped adverse event score. By taking the mean value after normalization, such a combination that the scores of a plurality of combinations belonging to the same group are high as a whole is extracted as having a high score. Since the grouping process is performed after all the values of scores are normalized to be between 0 and 1, the total value is not reduced even if such a combination that the value of the score before normalization is small (negatively large) exists in the same group. By taking the mean value, the tendency that the grouped adverse event score of such a combination that there are a lot of combinations belonging to the same group becomes higher is suppressed.

Though grouping is performed based on ICD10 codes, especially based on the top four digits thereof in the above description, grouping may be performed with the use of a disease classification system other than ICD10 codes, such as ICD9 codes (codes of ICD, 9th Edition).

[Modification 5]

Figure 13:
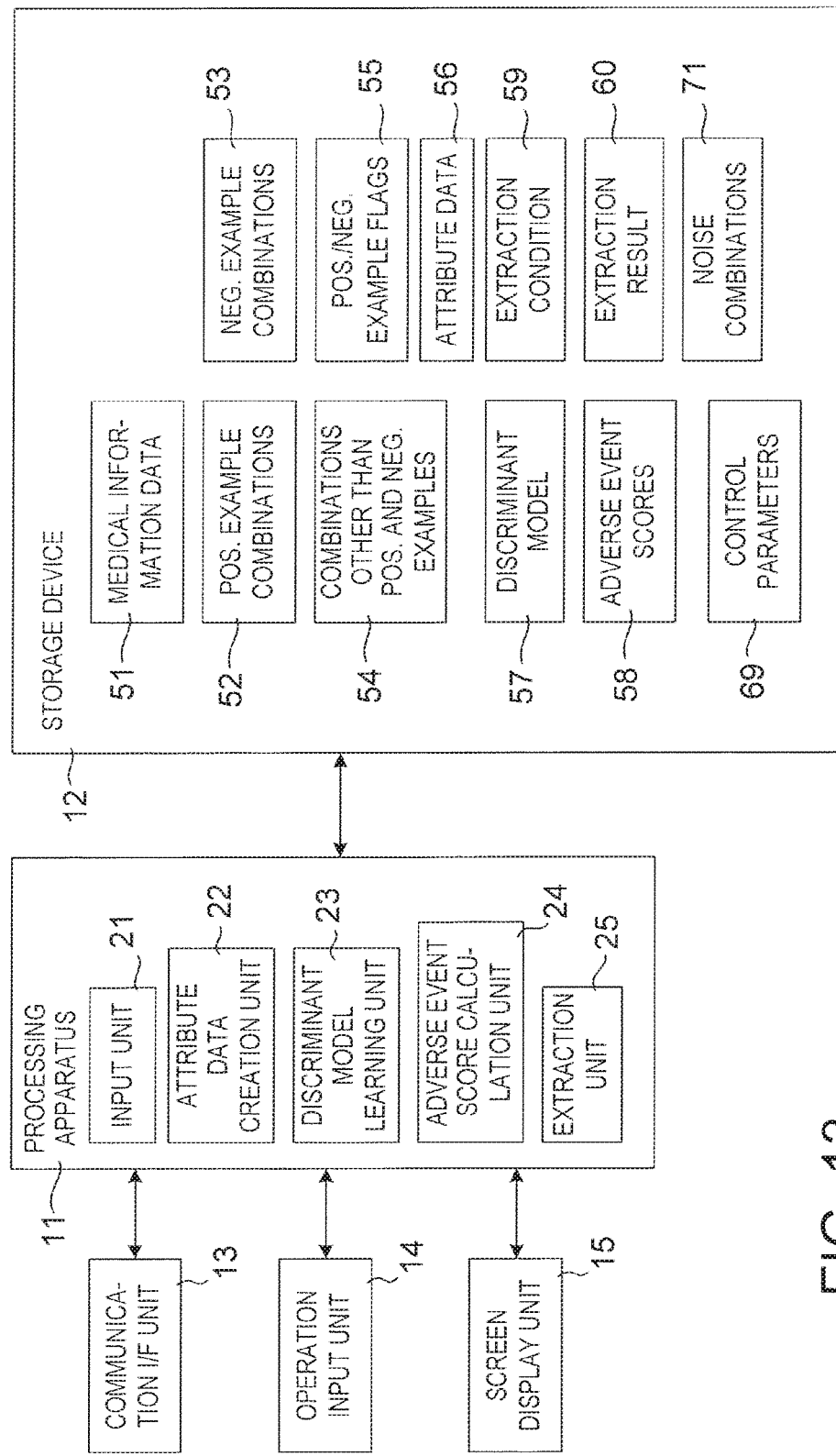
FIG. 13 is a block diagram showing a configuration of a drug adverse event extraction apparatus according to Modification 5.

FIG. 13 shows a configuration of a drug adverse event extraction apparatus according to Modification 5. Combinations of "drug and disease" obtained from medical information data may include those that are thought to be noise. Therefore, the apparatus of Modification 5 is such that, in the apparatus shown in FIG. 1, noise combinations 71 are stored in storage device 12 so that, at the time of extracting a combination suspected to be an adverse events, those corresponding to the noise combinations are excluded.

Here, the noise combination is such a combination that is hardly considered to be an adverse event. For example, such a combination that, for the drug and disease included in the combination, the number of patients in whom the disease appears within three months after the first prescription of the drug is zero can be regarded as noise. This is because a disease which has not occurred at all within three months after the first prescription is thought to be hardly suspected to be an adverse event caused by the drug. Further, for example, such a combination that, for the drug and disease included in the combination, the disease has not occurred in any patients within three months after prescription of the drug may be regarded as noise. This is because a disease which occurred in a patient before prescription of a drug is thought to be hardly suspected to be an adverse event.

Figure 14:
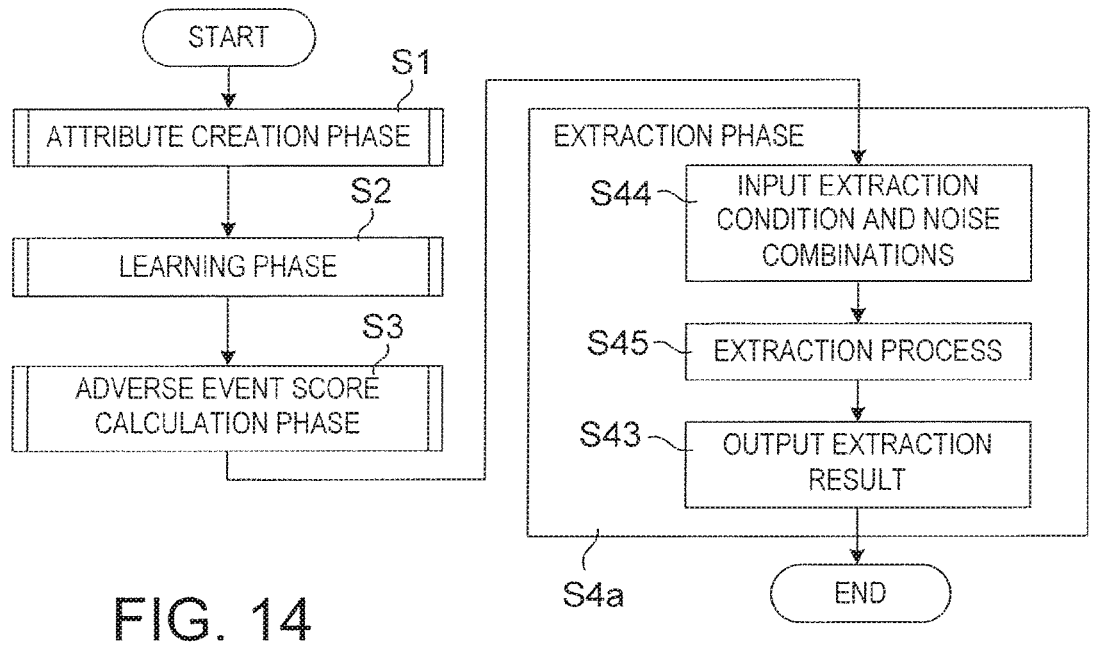
FIG. 14 is a flowchart showing the operation of the drug adverse event extraction apparatus shown in FIG. 13.

FIG. 14 shows the operation of the drug adverse event extraction apparatus of Modification 5 shown in FIG. 13. The operation in Modification 5 is such that extraction phase S4 in the operation shown in FIG. 2 is partially changed and caused to be extraction phase S4a. At extraction phase S4a, input unit 21 first receives an extraction condition and noise combinations from communication interface unit 13 or operation input unit 14 and stores them into storage device 12 at step S44. Next, at step S45, extraction unit 25 reads out adverse event scores 58, extraction condition 59 and noise combinations 71 from storage device 12, extracts combinations indicating adverse events from combinations other than positive and negative examples so that the combinations do not corresponding to the noise combinations and the extraction condition is satisfied, and stores a result of the extraction into storage device 12. After that, extraction unit 25 performs step S43 shown in FIG. 2, that is, output of the extraction result.

[Modification 6]

Figure 15:
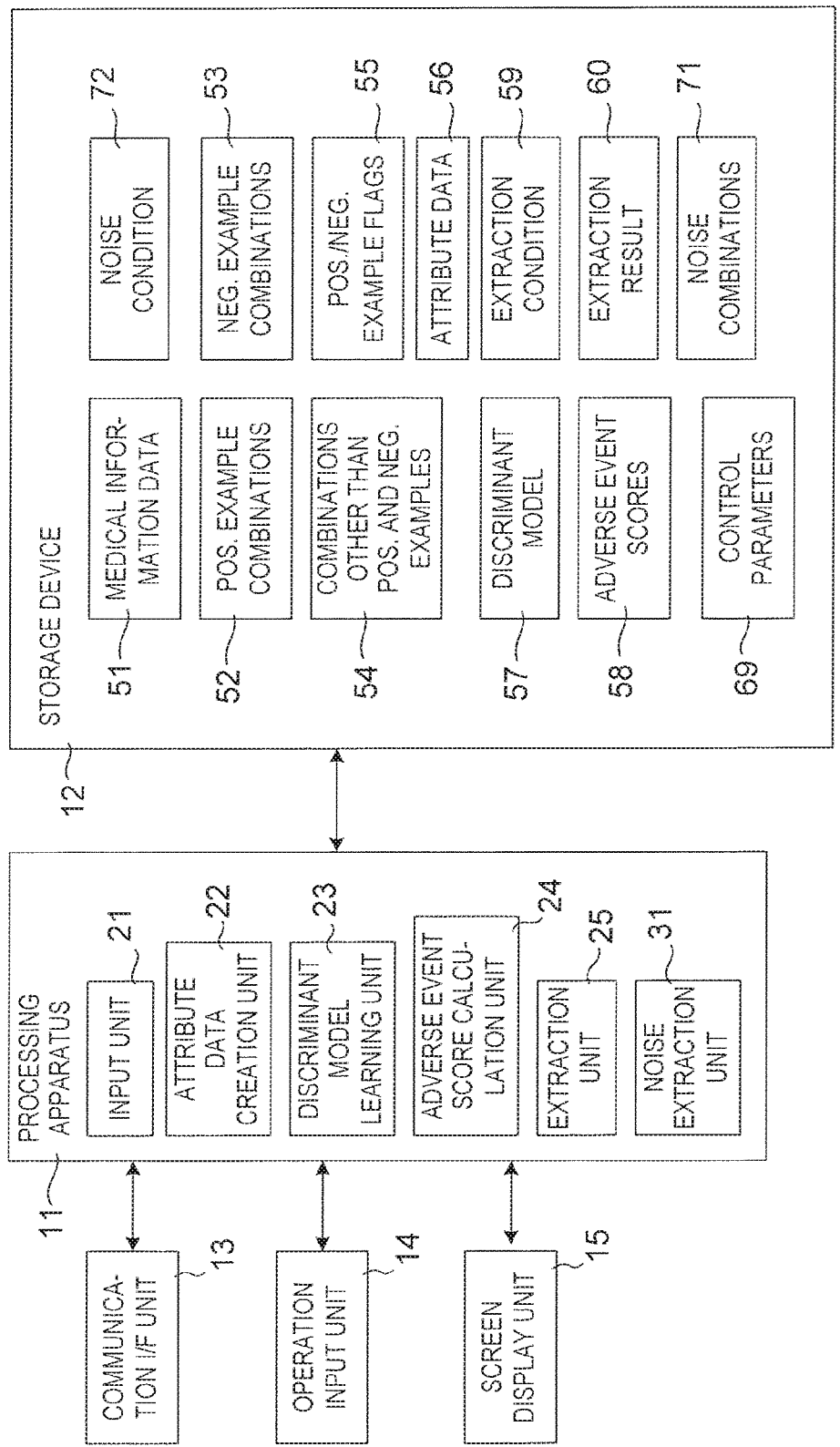
FIG. 15 is a block diagram showing a configuration of a drug adverse event extraction apparatus according to Modification 6.

FIG. 15 shows a configuration of a drug adverse event extraction apparatus according to Modification 6. In Modification 5 described above, noise combinations are given in advance. In Modification 6, however, only a condition for judging that a combination is noise, that is, a noise condition is given so that noise combinations can be automatically extracted from among combinations. The apparatus of Modification 6 as above is such that, in the apparatus of Modification 5, noise extraction unit 31 that performs combination of noises is provided in processing apparatus 11, and noise condition 72 is also stored in storage device 12. Noise extraction unit 31 corresponds to noise extracting means.

As the noise condition, for example, such a condition can be used that a combination of "drug and disease" is caused to be noise if the number of patients in whom the disease has occurred within three months after the first prescription of the drug is zero on medical information data. This is because a disease which has not occurred at all within three months after the first prescription is thought to be hardly suspected to be an adverse event caused by the drug. Further, for example, a condition that such a combination that the disease has not occurred in any patients within three months after prescription of the drug is caused to be noise may be adopted. This is because a disease which occurred in a patient before prescription of a drug is thought to be hardly suspected to be an adverse event.

Figure 16:
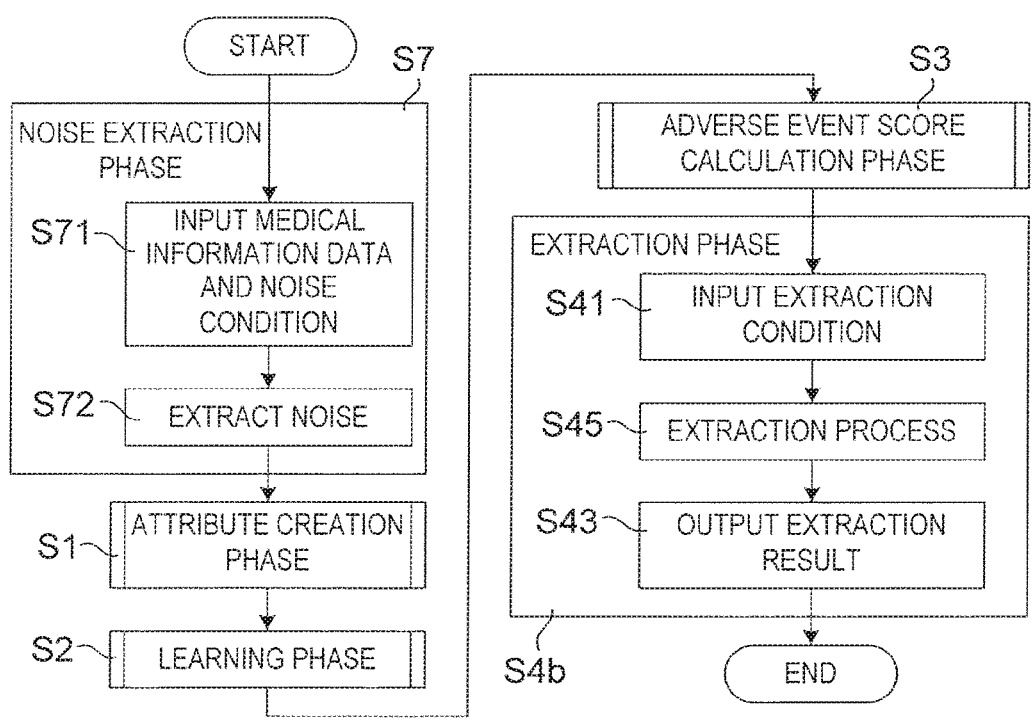
FIG. 16 is a flowchart showing the operation of the drug adverse event extraction apparatus shown in FIG. 15.

FIG. 16 shows the operation of the drug adverse event extraction apparatus of Modification 6 shown in FIG. 15. The operation in Modification 6 is such that, in the operation in Modification 5 shown in FIG. 14, noise extraction phase S7 is executed before attribute data creation phase S1, and extraction phase S4*a* is partially changed and caused to be extraction phase S4*b*. At noise extraction phase S7, input unit 21 first receives medical information data and a noise condition from communication interface unit 13 or operation input unit 14 and stores them into storage device 12 at step S71. Next, at step S72, noise extraction unit 31 reads the medical information data and the noise condition from storage device 12, searches the medical information data for what satisfies the noise condition, finds out a combination to be noise based on a result of the search, and stores them into storage device 12. On the other hand, at extraction phase S4*b*, step 41 of extraction phase S4 shown in FIG. 2 is executed, and input unit 21 receives an extraction condition from communication interface unit 13 or operation input unit 14 and stores it into storage device 12. Next, at step S45, extraction unit 25 reads out adverse event scores 58, extraction conditions 59 and noise combinations 71 from storage device 12, extracts combinations indicating adverse events from combinations other than positive and negative examples so that the combinations do not corresponding to the noise combinations and the extraction condition is satisfied, and stores a result of the extraction into storage device 12. After that, extraction unit 25 performs step S43 shown in FIG. 2, that is, output of the extraction result.

[Modification 7]

Figure 17:
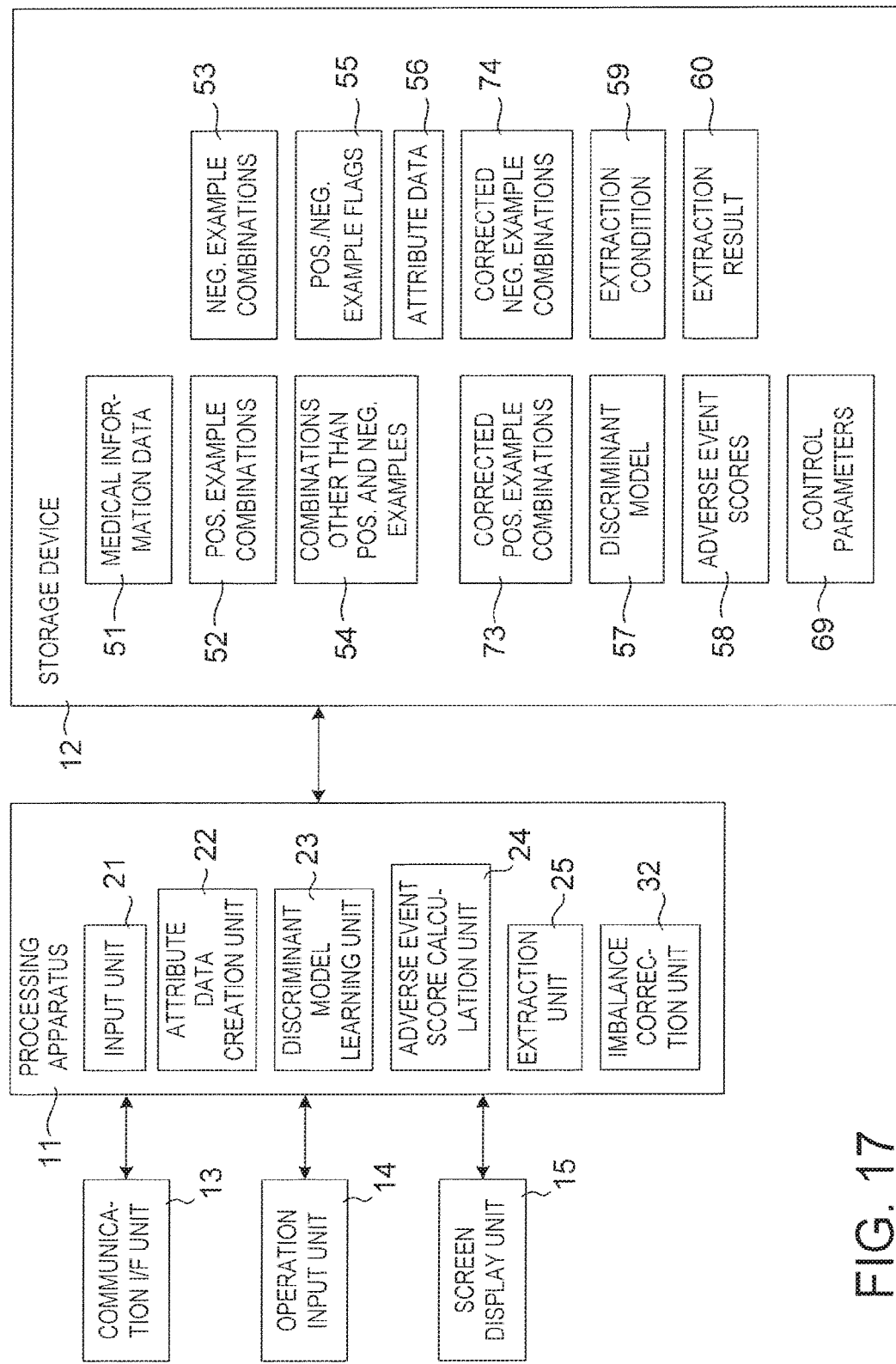
FIG. 17 is a block diagram showing a configuration of a drug adverse event extraction apparatus according to Modification 7.

FIG. 17 shows a configuration of a drug adverse event extraction apparatus according to Modification 7. In the case of using positive example combinations and negative example combinations to extract drug adverse events, there may be a case where any one of the number of positive examples and the number of negative examples is larger than the other. When there is imbalance between the number of positive examples and the number of negative examples, there is a possibility that the accuracy of learning of a discriminant model is degraded, and the accuracy of extraction of drug adverse events is degraded. Therefore, Modification 7 is such that, in the drug adverse event extraction apparatus shown in FIG. 1, imbalance correction unit 32 that corrects imbalance in the number between positive examples and negative examples is provided in processing apparatus 11, and corrected positive example combinations 73 and corrected negative example combinations 74 are stored in storage device 12, in order to correct the imbalance between the number of positive example combinations and the number of negative example combinations. Imbalance correction unit 32 corresponds to correction means, and it corrects imbalance in the number between positive examples and negative examples by generating pseudo examples (pseudo positive examples or pseudo negative examples) for positive examples or negative examples the number of which is smaller than the other, or deleting some combinations from positive examples or negative examples the number of which is larger than the other. The imbalance in the number between positive examples and negative examples may be corrected by generating both of pseudo positive examples and pseudo negative examples in a manner the number of generated examples differs, or the imbalance in the number between positive examples and negative examples may be corrected by deleting both of positive examples and negative examples in a manner the number of deleted examples differs. Positive example combinations and negative example combinations after such correction is performed are referred to as corrected positive example combinations and corrected negative example combinations, respectively. At the time of learning discriminant model 57, learning of discriminant model 57 is to be performed so that the number is not imbalanced between positive examples and negative examples by using corrected positive example combinations 73 and corrected negative example combinations 74.

Figure 18:
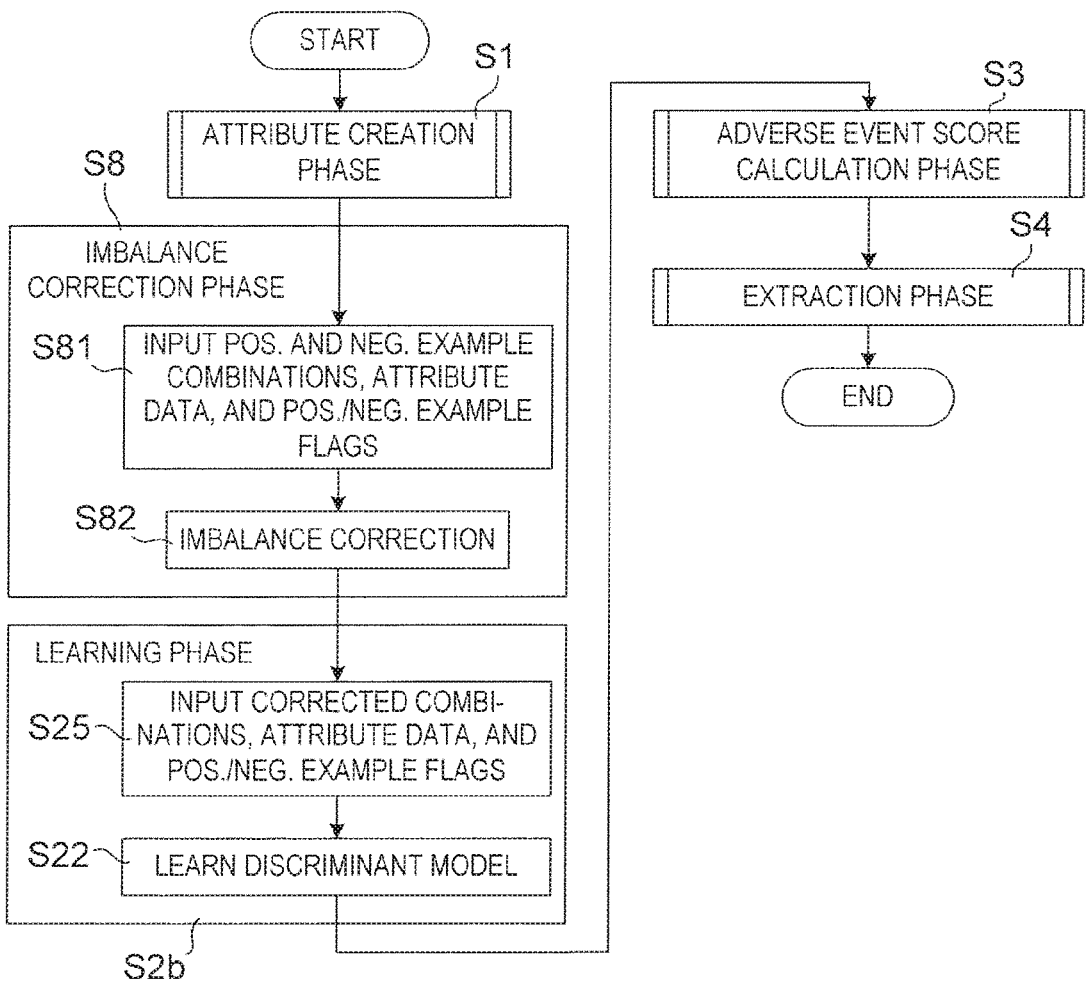
FIG. 18 is a flowchart showing the operation of the drug adverse event extraction apparatus shown in FIG. 17.

FIG. 18 shows the operation of the drug adverse event extraction apparatus of Modification 7 shown in FIG. 17. The operation in Modification 7 is such that, in the operation shown in FIG. 2, imbalance correction phase S8 is executed immediately after attribute data creation phase S1, and learning phase S2*b* at which learning of a discriminant model is performed with the use of corrected positive examples and corrected negative examples is provided instead of learning phase S2.

At imbalance correction phase S8, imbalance correction unit 32 first receives positive example combinations 52, negative example combinations 53, attribute data 56 thereof and positive/negative example flags 55 from storage device 12 at step S81. Next, at step S82, imbalance correction unit 32 executes an imbalance correction process for generating at least either pseudo positive examples or pseudo negative examples and storing the pseudo examples into storage device 12. The pseudo positive example combinations and pseudo negative example combinations are not derived from actual medical information data but are data generated as pseudo combinations of "drug and disease" so that they can be used for learning of a discriminant model as positive example combinations and negative example combinations. As a method for generating pseudo positive examples and negative examples, for example, the method described in [NPL4] can be used.

Otherwise, at step S82, imbalance correction unit 32 executes an imbalance correction process for performing correction of deleting combinations from the positive examples or negative examples the number of which is larger than the other and storing combinations into storage device 12. As a method about how to select combinations to be deleted from the positive examples or negative examples the number of which is larger than the other, for example, the method described in [NPL5] can be used.

When generation of pseudo examples or deletion of combinations is performed for either positive examples or negative examples at step S82, the positive examples or the negative examples for which such generation of pseudo examples or deletion of combinations are not performed are caused to be corrected combinations as they are in the original state.

At learning phase S2b, discriminant model learning unit 23 calls corrected positive example combinations 73, corrected negative example combinations 74, attribute data 56 corresponding to these combinations, positive/negative example flags 55 and discriminant model 57 from storage device 12 at step S25, and, with the use of these, learns the discriminant model at step S22 similarly to the case shown in FIG. 2. The learned discriminant model is returned to storage device 12. Following learning step S2b, adverse event score calculation phase S3 and extraction phase S4 shown in FIG. 2 are executed as they are.

[Modification 8]

Figure 19:
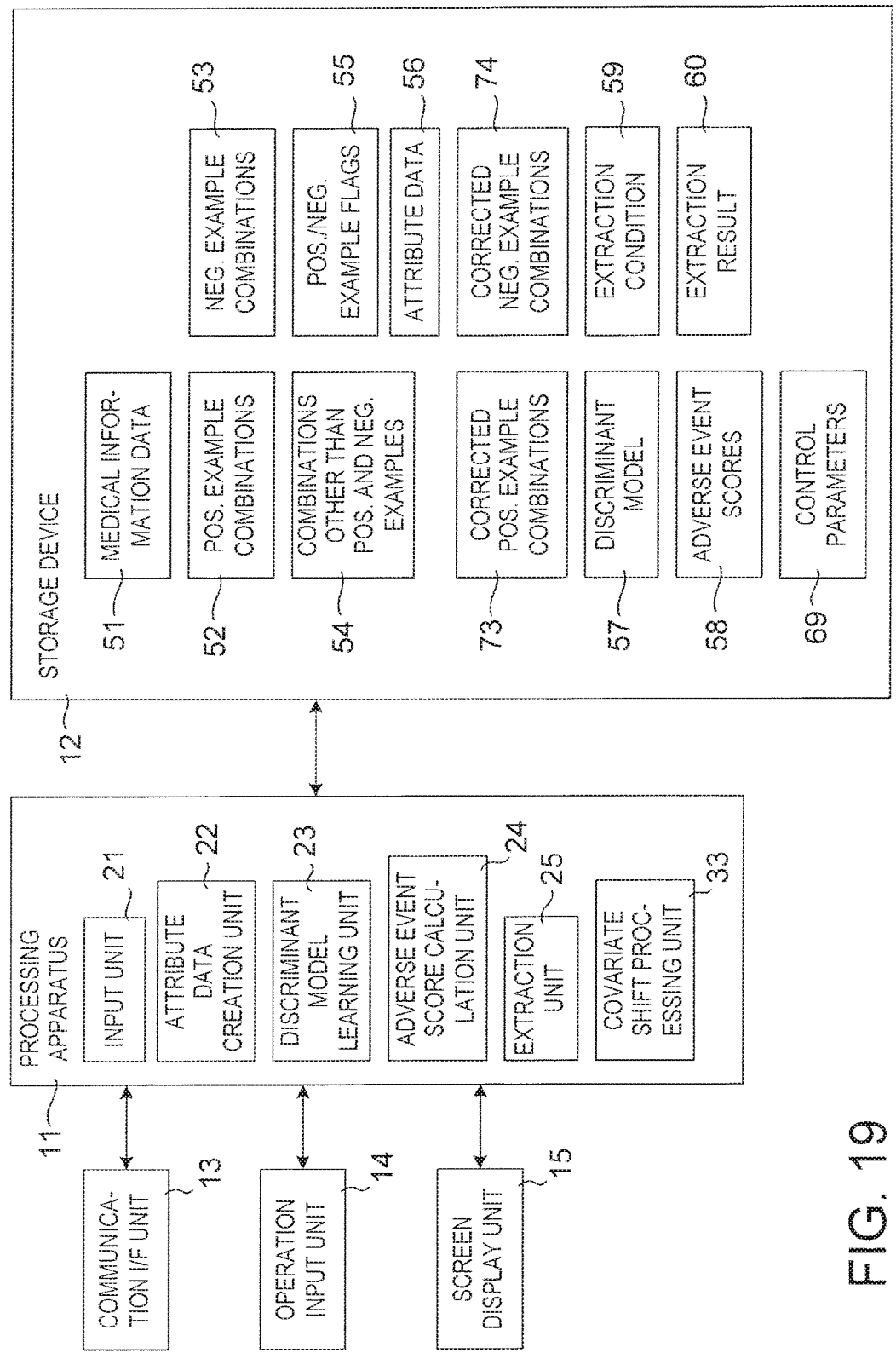
FIG. 19 is a block diagram showing a configuration of a drug adverse event extraction apparatus according to Modification 8.

FIG. 19 shows a configuration of a drug adverse event extraction apparatus according to Modification 8. The examples described so far are such that make it possible to extract a drug adverse event with a high accuracy by learning a discriminant model using positive example combinations and negative example combinations, and giving a high adverse event score to a combination the attribute data of which resembles that of a positive example, among combinations other than positive and negative examples, on the assumption that distribution of learning data (positive example combinations and negative example combinations) on an attribute data space and distribution of evaluation data (combinations other than positive and negative examples) resemble each other. However, if there is a difference between the distribution of learning data on the attribute data space and the distribution of evaluation data, there is a possibility that, even if the discriminant model is learned with the use of the positive and negative example combinations as they are, it becomes difficult to extract a drug adverse event from among the combinations other than positive and negative examples with a high accuracy using the discriminant model.

On the other hand, though positive example combinations already known as adverse events and negative example combinations already known as not being adverse events are used as learning data, and, for each combination, attribute data is created from medical information data in the present invention, it can be thought that this medical information data is influenced by history of medical events performed by a doctor to suppress appearance of an already-known adverse event, history of a medical event performed in a situation that a doctor knows that a combination is not an adverse event, and the like. Therefore, it can be thought that there is some difference in the distribution on the attribute data space between positive example combinations or negative example combinations and such combinations that whether they are adverse events or not is not clearly known yet.

The situation that there is a difference between the distribution of learning data on the attribute data space and the distribution of evaluation data can be interpreted as a situation that a covariate shift has occurred in which, though the regularity of an output (corresponding to an adverse event score in the present exemplary embodiment) to a given input (corresponding to a combination of "drug and disease" in the present exemplary embodiment) does not differ between learning data (positive and negative example combinations used to learn a discriminant model) and evaluation data (combinations other than positive and negative examples), distribution of given learning data and distribution of evaluation data on attribute data space differ.

Therefore, in Modification 8, a covariate shift learning method is applied which is known as a learning technique capable of discriminating between a positive example and a negative example using a discriminant model with a high accuracy even when a covariate shift has occurred.

In order to apply the covariate shift learning technique, it is necessary to know distribution of evaluation data in advance at the time of learning a discriminant model using learning data. In the technique of the present exemplary embodiment, however, evaluation data (combinations other than positive and negative examples) is known in advance, and, therefore, the covariate shift learning technique can be applied. In general machine learning problems, the situation that evaluation data is known in advance is rare, and it is one of the features of the present exemplary embodiment that evaluation data is known in advance.

A typical example of the covariate shift learning technique is described in [NPL6]. This technique is a technique in which learning data located in a high density area of evaluation data on the attribute data space is weighted much, and a discriminant model is learned in consideration of the weight. That is, the technique is a method in which highly weighted learning data for which evaluation data and attribute data resemble each other is learned being focused on, and slightly weighted learning data for which attribute data does not resemble evaluation data is prevented from being reflected much on learning of a discriminant model.

If the density of combination x in evaluation data is indicated by $p_{test}(x)$, and the density of combination x in learning data is indicated by $p_{train}(x)$, then weight W(x) of combination x is derived from the expression below.

$$W(x) = \frac{p_{test}(x)}{p_{train}(x)}$$

The above expression shows that higher weight is given to combination x when the density of the evaluation data on the attribute data space is high. In other words, the higher the density of the evaluation data on the attribute data space is, the higher weight combination x generally costs much, a method for suppressing the calculation cost is needed. A technique of suppressing the calculation cost by directly estimating density W(x) without directly estimating $p_{test}(x)$ and $p_{train}(x)$ is described in [NPL6]. In Modification 8, a technique like that of [NPL6] may be used as a learning technique under covariate shift.

Further, in Modification 8, a method may be used in which positive and negative example combinations that are homogeneous to combinations other than positive and negative examples are searched for, and these positive and negative example combinations are learned being focused on, without estimating densities or a density ratio. In this method, the homogeneous positive and negative example combinations are searched for, based on a Euclidean distance in an attribute data space. Hereinafter, the apparatus and its operation in Modification 8 will be described, with the case of using this method as an example.

The apparatus of Modification 8 is such that corrected positive example combinations and corrected negative example combinations are generated by a covariate shift process and such that covariate shift processing unit 33 that executes the covariate shift process is provided instead of imbalance correction unit 32 in the apparatus shown in FIG. 17. The corrected positive example combinations and the corrected negative example combinations in Modification 8 are obtained by generating and adding pseudo positive or pseudo negative example combinations or by deleting a part of original positive and negative example combinations similarly to the case of Modification 7. Covariate shift unit 33 corresponds to covariate shift means. Since attribute data is indicated by a multidimensional vector as described above, a vector space which includes this multidimensional vector is called an attribute data space. Then, in the case of creating pseudo positive and pseudo negative example combinations by the covariate shift process, it is favorable to create each combination so that attribute data of the pseudo positive examples and pseudo negative examples is located in the vicinity of the existence of attribute data of combinations other than positive and negative examples in an attribute data space. In the case of deleting a part of original positive and negative example combinations by the covariate shift process, it is preferable to delete positive and negative example combinations corresponding to attribute data far away from the attribute data of the combinations other than positive and negative examples in the attribute data space.

Figure 20:
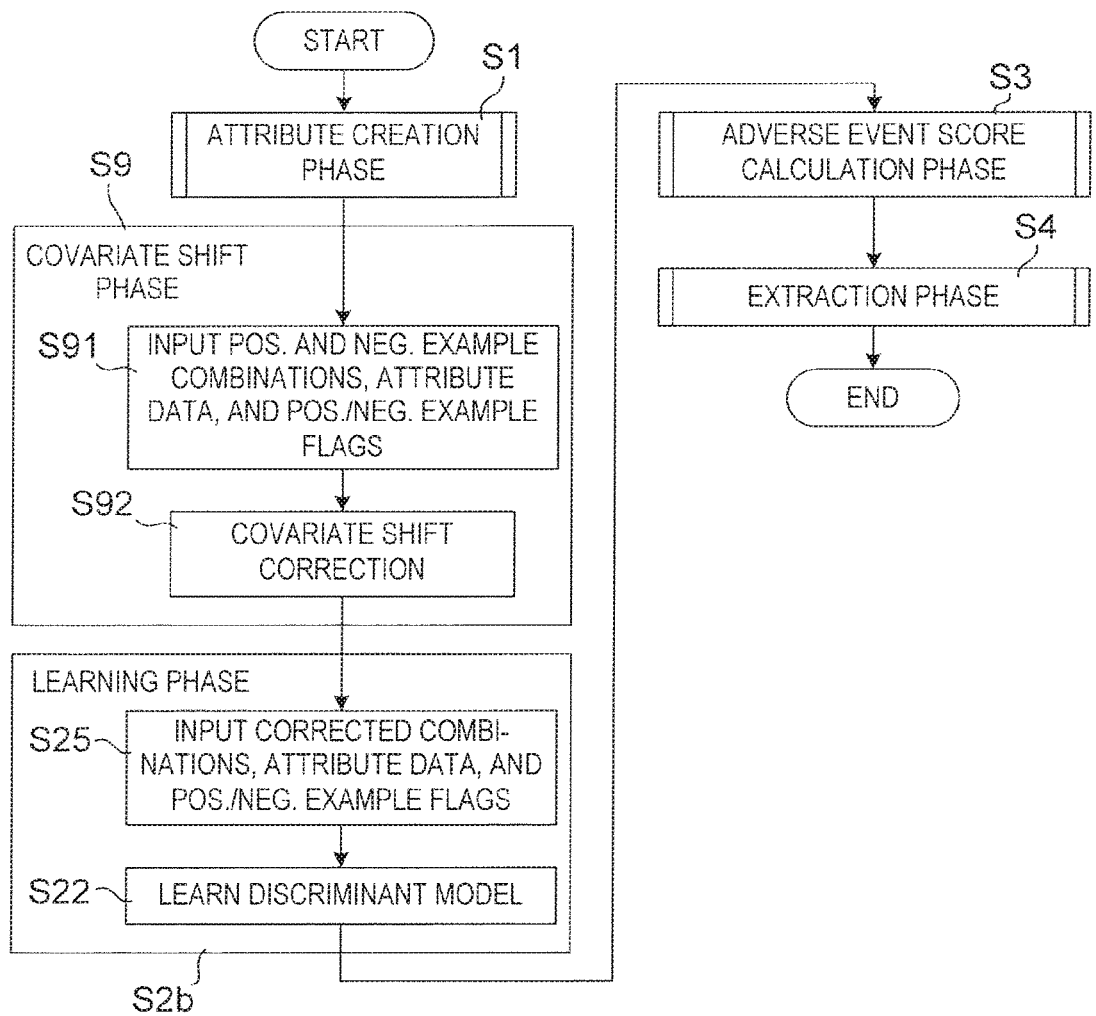
FIG. 20 is a flowchart showing the operation of the drug adverse event extraction apparatus shown in FIG. 19.

FIG. 20 shows the operation of the drug adverse event extraction apparatus of Modification 8 shown in FIG. 19. The operation of Modification 8 is such that imbalance correction phase S8 in the operation of Modification 7 shown in FIG. 18 is replaced with covariate shift phase S9. At covariate shift phase S9, covariate shift processing unit 33 first receives positive example combinations 52, negative example combinations 53, attribute data 56 thereof, and positive/negative example flags 55 from storage device 12 at step S91. Next, at step S92, covariate shift processing unit 33 generates at least either pseudo positive example combinations or pseudo negative example combinations by the covariate shift process, and stores them into storage device 12 together with original positive and negative example combinations as corrected positive example combinations 73 and corrected negative example combinations 74. Otherwise, at step S92, covariate shift unit 33 performs correction of deleting a part of the positive and negative example combinations, and stores positive and negative example combinations after the partial deletion is performed, into storage device 12 as corrected positive example combinations 73 and corrected negative example combinations 74. It is also possible to perform generation/addition of the pseudo positive and pseudo negative example combinations and deletion of a part of the original positive and negative example combinations at the same time, and causes the result to be corrected positive example combinations 73 and corrected negative example combinations 74.

Here, the flow of the covariate shift process will be simply described.

Attribute data of combination x is assumed to be a d-dimensional vector, and the k-th vector element of x is indicated by $x_k$. Evaluation data showing combinations other than positive and negative examples is indicated by $D_{test}$, and learning data indicating positive and negative example combinations is indicated by $D_{train}$.

Centroid $x^c$ of evaluation data $D_{test}$ is a vector for which each vector element is calculated by:

$$x_k^c = \frac{1}{n}\sum_{i=1}^{n} x_k^i$$

Here, it is assumed that n indicates the number of pieces of evaluation data (that is, the number of combinations other than positive and negative examples). Mean Centroid distance "mean" of evaluation data $D_{test}$ is the average of the distance from the evaluation data to the centroid calculated by the following expression:

$$\text{mean} = \frac{1}{n}\sum_{i=1}^{n} dist(x^i, x^c)$$

Here, the Euclidean distance of sample $x^i$ and sample $x^j$ is indicated by $dist(x^i,x^j)$, and, specifically, calculated by the following expression:

$$dist(x^i,x^j) = \sqrt{\sum_{k=1}^{d}(x_k^i - x_k^j)}$$

Centroid distance deviation "stdev" of test data $D_{test}$ is the standard deviation of the distance from the evaluation data to the centroid calculated by the following expression:

$$stdev = \sqrt{\frac{1}{n}\sum_{i=1}^{n}(dist(x^i, x^c) - \text{mean})^2}$$

Similarly, it is assumed that median centroid distance "median" of evaluation data $D_{test}$ is the median of distance from the evaluation data to the centroid. In calculation of centroid distance deviation "stdev", "mean" may be used, or "median" may be used instead of "mean".

In this method, the Euclidean distance space is used, and, by regarding such learning data that the Euclidean distance to the centroid of evaluation data is short as learning data which is also close to distribution of the evaluation data, this learning data is learned being focused on. Moreover, for further simplification, it is assumed that the number of the values of weight is only three, that is, the values of weight are 2, 1 and 0. Weight 2 is given to the learning data to be learned being focused on, and weight 0 is given to learning data which is, on the contrary, not desired to be reflected on a discriminant model. Weight 1 is given to other learning data. As for the learning data with the weight 2, duplicates (that is, pseudo positive or pseudo negative example combinations) are created and added to the learning data, and the learning data with the weight 0 is removed (that is, corresponding positive or negative example combinations are deleted). The calculation procedure is as follows.

1: Centroid $x^c$, mean centroid distance "mean" and centroid distance deviation "stdev" of evaluation data are calculated, and weight w(x) of learning data x is calculated. Specifically, for each learning data x, distance $dist(x, x^c)$ to centroid $x^c$ is calculated, and weight w(x) is obtained by the following expression.

$$w(x) = \begin{cases} 2 & dist(x, x^c) \le \text{mean} - a \cdot stdev \\ 1 & \text{mean} - a \cdot stdev < dist(x, x^c) \le \text{mean} + b \cdot stdev \\ 0 & \text{mean} + b \cdot stdev < dist(x, x^c) \end{cases}$$

Here, a and b are positive number parameters. In the above expression, median centroid distance "median" may be used instead of "mean". Whether to use "mean" or "median" can be also selected as a parameter. These parameters are stored in storage device 12 as control parameters 69.

2: When w(x) is 2, one more x is added to the learning data. When w(x) is 0, x is deleted from the learning data.

As described above, as the covariate shift process, pseudo positive example combinations and pseudo negative example combinations are added, or positive example combinations and negative example combinations corresponding to attribute data far away from attribute data of combinations other than positive and negative examples in an attribute data space are deleted.

[Modification 9]

Figure 21:
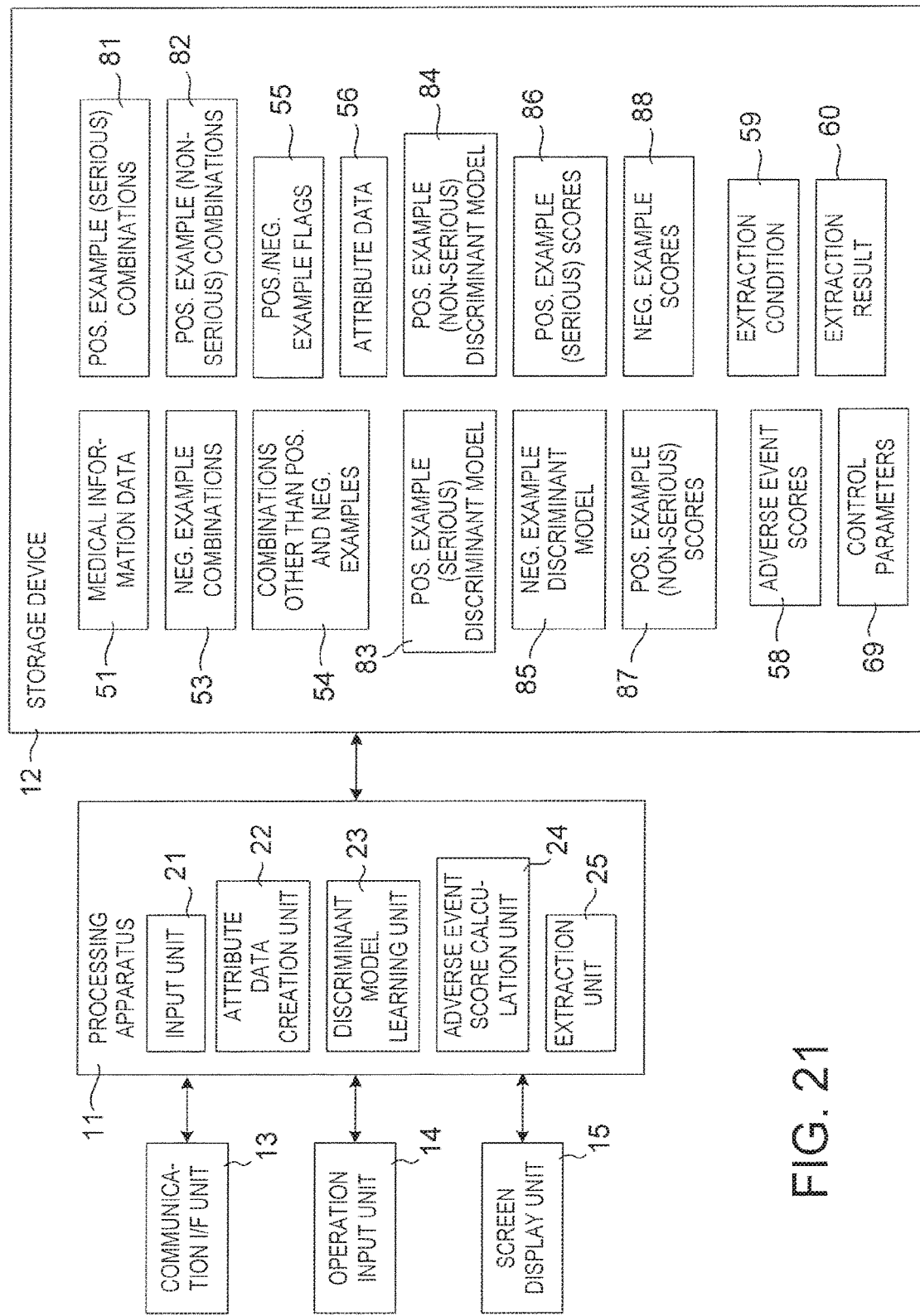
FIG. 21 is a block diagram showing a configuration of a drug adverse event extraction apparatus according to Modification 9.

FIG. 21 shows a configuration of a drug adverse event extraction apparatus according to Modification 9. In extraction of a drug adverse event, it is important to consider whether the adverse event is such that brings about serious health damage or not. It is preferable to detect an adverse event which brings about serious health damage earlier. Therefore, in the apparatus of Modification 9 shown in FIG. 21, positive example combinations are classified into combinations corresponding to serious adverse events (referred to as "positive example (serious) combinations) and combinations corresponding to non-serious adverse events (referred to as "positive example (non-serious) combinations). Whether "serious" or "non-serious" reflects difference in the degree of seriousness. Because there are negative example combinations also, Modification 3 relates to a ternary discrimination problem. Therefore, in the apparatus of Modification 9 shown in FIG. 21, positive example (serious) combinations 81, positive example (non-serious) combinations 82, positive example (serious) discriminant model 83, positive example (non-serious) discriminant model 84 and negative example discriminant model 85 are stored in storage device 12 instead of storing positive example combinations 52 and discriminant model 57, and, furthermore, positive example (serious) scores 86, positive example (non-serious) scores 87 and negative example scores 88 are also stored, in comparison with the apparatus shown in FIG. 1.

Figure 22:
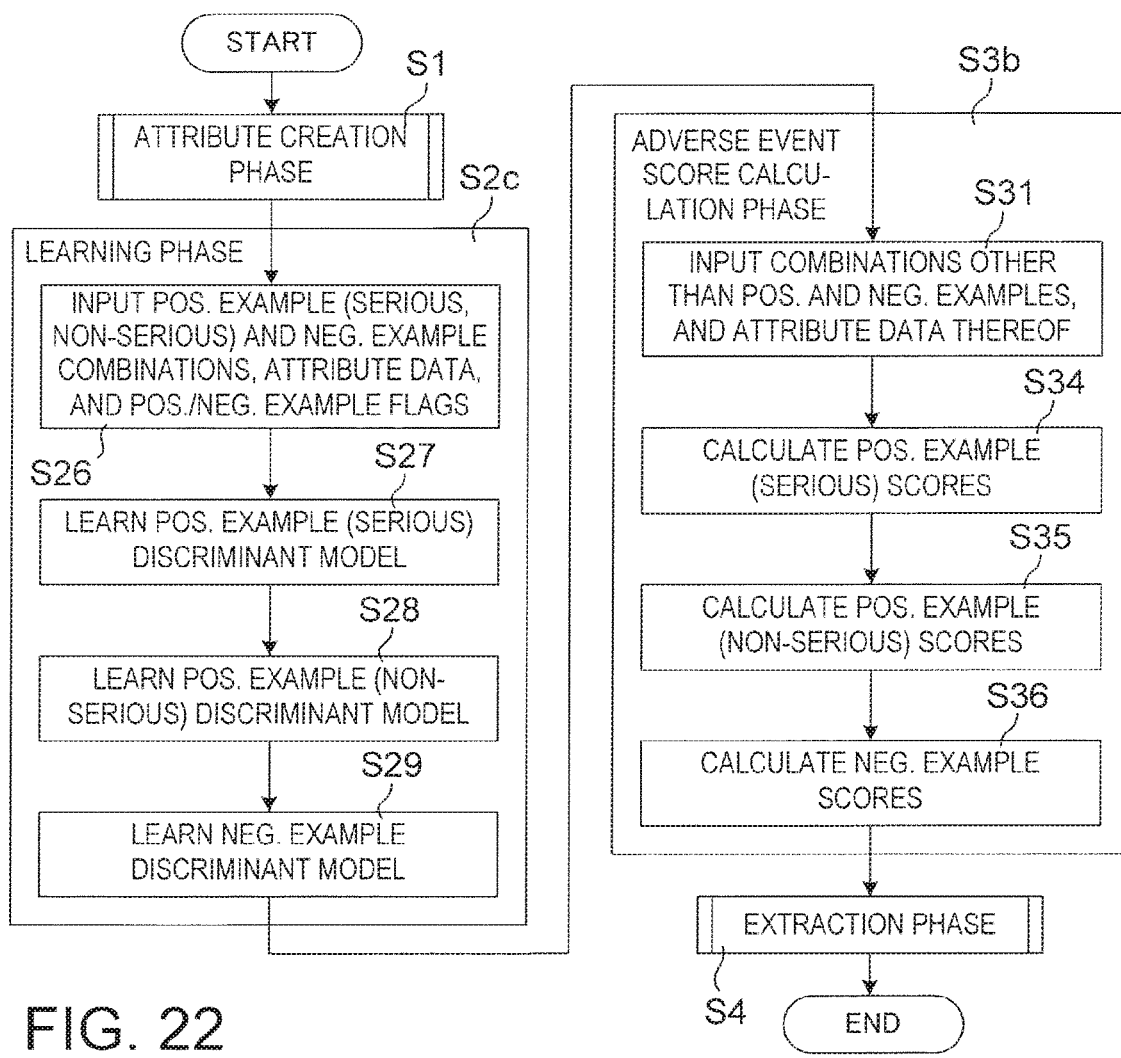
FIG. 22 is a flowchart showing the operation of the drug adverse event extraction apparatus shown in FIG. 21.

FIG. 22 shows the operation of the drug adverse event extraction apparatus of Modification 9 shown in FIG. 21. In the operation of Modification 9, instead of learning phase S2 and adverse event score calculation phase S3 in the operation shown in FIG. 2, learning phase S2c and adverse event score calculation phase S3b are provided, respectively.

At learning phase S2c, discriminant model learning unit 23 calls positive example (serious) combinations 81, positive example (non-serious) combinations 82, negative example combinations 53, attribute data 56 corresponding to the positive examples (serious), the positive examples (non-serious) and the negative examples, positive/negative example flags 55, positive example (serious) discriminant model 83, positive example (non-serious) discriminant model 84 and negative example discriminant model 85 from storage device 12 at step S26. At step S27, discriminant model learning unit 23 learns positive example (serious) discriminant model 85, with the positive example (serious) combinations as positive examples, and other combinations (the positive examples (non-serious) and the negative examples) as negative examples; learns positive example (non-serious) discriminant model 86, with the positive example (non-serious) combinations as positive examples, and other combinations (the positive examples (serious) and the negative examples) as negative examples; and learns negative example discriminant model 85 with the negative example combinations as positive examples, and other combinations (the positive examples (serious) and the positive example (non-serious)) as negative examples. Learned discriminant models 84 to 86 are returned to storage device 12.

At adverse event score calculation phase S3b, adverse event score calculation unit 24 reads out positive example (serious) discriminant model 83, positive example (non-serious) discriminant model 84, negative example discriminant model 85, combinations other than positive and negative examples 54, and attribute data corresponding to the combinations from storage device 12 at step S31.

Next, adverse event score calculation unit 24 applies the read-out attribute data to positive example (serious) discriminant model 83 to calculate positive example (serious) scores and stores the scores into storage device 12 at step S34; applies the read-out attribute data to positive example (non-serious) discriminant model 84 to calculate positive example (non-serious) scores and stores the scores into storage device 12 at step S35; and applies the read-out attribute data to negative example discriminant model 85 to calculate negative example scores and stores the scores into storage device 12 at step S36.

Lastly, at step S4, extraction unit 25 reads out the combinations other than positive and negative examples and the positive example (serious) scores, positive example (non-serious) scores and negative example scores of the combinations from storage device 12 and sequentially extracts the combinations in rule order as shown in the example below.

1: extract such combinations that the positive example (serious) score and the positive example (non-serious) score are positive and the negative example score is negative, in descending order of the positive example (serious) scores;

2: extract such combinations that the positive example (serious) score is positive and the positive example (non-serious) score and the negative example score are negative, in descending order of the positive example (serious) scores;

3: extract such combinations that the positive example (non-serious) score is positive and the positive example (serious) score and the negative example score are negative, in descending order of the positive example (non-serious) scores;

4: extract such combinations that all of the positive example (serious) score, the positive example (non-serious) score and the negative example score are negative, in descending order of the absolute values of the negative example scores;

5: extract such combinations that the negative example score is positive, the positive example (serious) score is positive, and the positive example (non-serious) score is negative, in descending order of the positive example (serious) scores;

6: extract such combinations that the negative example score is positive, the positive example (serious) score is negative, and the positive example (non-serious) score is positive, in descending order of the positive example (non-serious) scores; and 7: extract such combinations that the negative example score is positive, and the positive example (serious) score and the positive example (non-serious) score are negative, in ascending order of the negative example scores.

The combinations may be sequentially extracted in rule order other than the rule order of the method in the above example.

In Modification 9, some seriousness degree is introduced, and positive examples are classified in two of "serious" and "non-serious". Positive examples, however, can be classified in three or more levels depending on the degree of seriousness.

[Modification 10]

Figure 23:
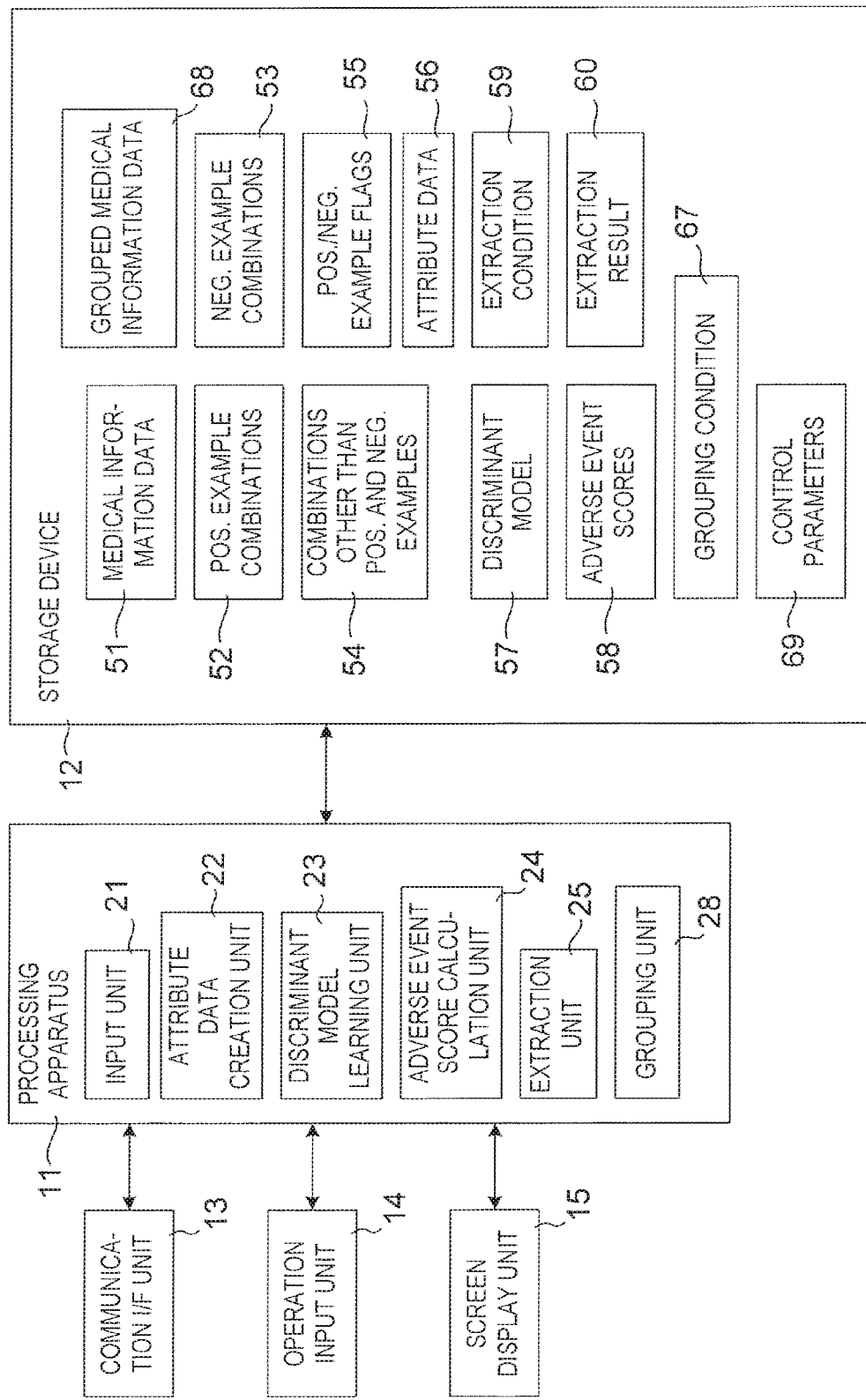
FIG. 23 is a block diagram showing a configuration of a drug adverse event extraction apparatus of according to Modification 10.

FIG. 23 shows a configuration of a drug adverse event extraction apparatus according to Modification 10. In Modification 4, grouping of extracted combinations is performed. In the apparatus of Modification 10, however, grouping is performed at a stage of medical information data to be inputted (the grouping is also referred to as prior grouping). For example, when there are a plurality of drugs showing the same efficacy, there may be a case where it is preferable to treat the plurality of drugs as one kind of drug. Therefore, the apparatus of Modification 10 is such that, in the apparatus shown in FIG. 1, grouping unit 28 which performs grouping is provided in processing apparatus 11, and grouping condition 67 and grouped medical information data 68 are stored in storage device 12. Grouping unit 28 corresponds to prior grouping means.

Figure 24:
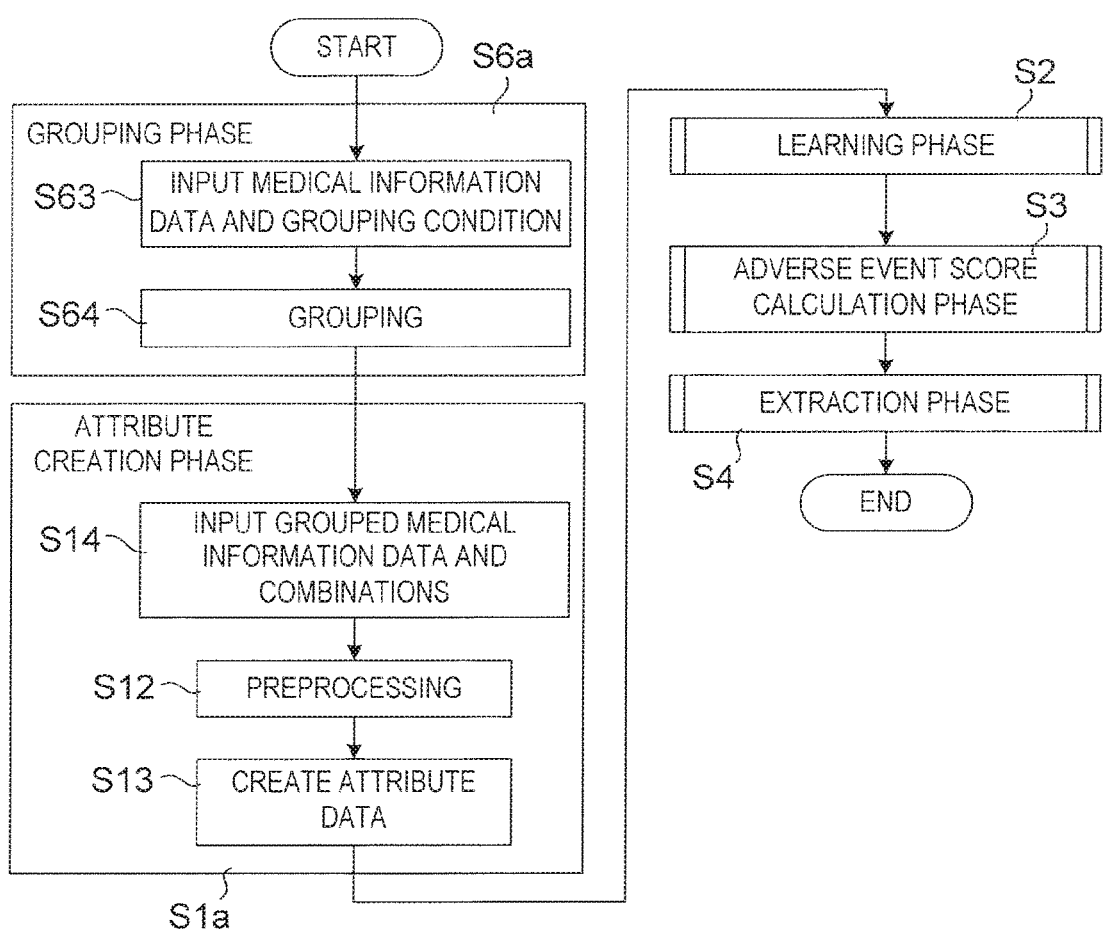
FIG. 24 is a flowchart showing the operation of the drug adverse event extraction apparatus shown in FIG. 23.

FIG. 24 shows the operation of the drug adverse event extraction apparatus of Modification 10 shown in FIG. 23. The operation of Modification 10 is such that attribute data creation phase S1a corresponding to grouped medical information data is performed instead of attribute data creation phase 51 in the operation shown in FIG. 2, and, furthermore, grouping phase S6a is provided at the preceding stage of attribute data creation phase S1a for creation of the grouped medical information data. At grouping phase S6a, input unit 21 receives medical information data, positive examples, negative examples, combinations other than positive and negative examples, and a grouping condition from communication interface unit 13 or operation input unit 14 and stores them into storage device 12 at step S63. At this time, as the positive examples, the negative examples and the combinations other than positive and negative examples, combinations for which grouping can be performed are used. Next, at step S64, grouping unit 28 reads out medical information data 51 and grouping condition 67 from storage device 12, performs grouping of the medical information data based on the grouping condition, and stores a result into storage device 12 as grouped medical information data. At attribution creation phase S1a, attribute data creation unit 22 first reads out grouped medical information data 68, positive example combinations 42, negative example combinations 53, combinations other than positive and negative examples 54 and control parameters 69 from storage device 12 at step S14. Next, at step S12, attribute data creation unit 22 performs preprocessing, and, at step S13, creates attribute data corresponding to each of the read-out combinations and stores the created attribute data into storage device 12. After that, learning phase S2, adverse event score calculation phase S3 and extraction phase in the operation shown in FIG. 2 are executed.

In Modification 10, in the case of grouping drugs having the same efficacy, a list of same efficacy groups (a list of drugs showing the same efficacy) is used as the grouping condition. Grouping unit 28 performs a process for replacing drug names which are included in the medical information data and written in the list of same efficacy groups with same efficacy group names. At the learning phase, a discriminant model is learned, with the positive examples, negative examples and combinations other than positive and negative examples for which drug names are indicated by same efficacy group names, in addition to the grouped medical information data replaced with efficacy group names, used as input. After that, at adverse event score calculation phase S3, adverse event scores are calculated with the use of the learned discriminant model.

Further, in Modification 10, grouping of disease names can be performed. In the case of performing grouping of disease names, it is preferable to use ICD10 codes. ICD9 codes and the like can also be used in addition to ICD 10 codes. In the case of performing grouping using ICD10 codes, a table of correspondence between ICD10 codes and disease names is used as the grouping condition, and a process for converting disease names included in the medical information data to ICD 10 codes is executed by grouping unit 28. At the learning phase, a discriminant model is learned, with the positive examples, negative examples and combinations other than positive and negative examples for which diseases are indicated by ICD10 codes, in addition to the grouped medical information data for which disease names are replaced with ICD10 codes, used as input. After that, at adverse event score calculation phase S3, adverse event scores are calculated with the use of the learned discriminant model.

Various Modifications of the present exemplary embodiment have been described above. These Modifications can be arbitrarily combined except for those that cannot be combined from a viewpoint of the principle like Modifications 2 and 3.

In the exemplary embodiment and modifications described above, at the time of determining attribute data for each combination of "drug and disease" from time-series information about medical events, such medical events are used that include not only prescription of a drug for a patient and a disease observed in the patient but also at least one of a medical act performed for the patient and an event indicating that the medical act has been performed, accompanying the medical act. If an adverse event occurs on the patient, the patient sees a doctor at any hospital department to treat it, a medical act is performed to examine/treat it, and the patient is charged for medical expenses for the medical act. Therefore, it is expected that some difference appears in time-series information about the medical events of medical act, hospitalization, medical expenses, hospital department and the like between the case an adverse event has occurred and the case where an adverse event has not occurred. In the exemplary embodiment and each Modification that have been described above, attribute data focusing only on occurrence of a disease during a prescription period of a drug is not used but attribute data on which such difference depending on occurrence/non-occurrence of an adverse event is to be reflected is used. Therefore, it becomes possible to extract adverse events more widely and with fewer mistakes.

The present invention has been described above with reference to exemplary embodiments and modifications thereof. The present invention, however, is not limited to the exemplary embodiments and modifications described above. Various changes that those skilled in the art can understand within the scope of the present invention can be made in the configuration and details of the present invention.

The present application claims priority based on JP 2014-57635 filed to Japan on Mar. 20, 2014, all the disclosure of which is incorporated herein.

A part or all of the exemplary embodiment described above can be written as in supplements below but are not limited to the supplementary notes below.

[Supplementary Note 1]

A drug adverse event extraction method of extracting a combination of a drug and a disease corresponding to a drug adverse event, the method comprising, on assumption that combinations already known as combinations indicating drug adverse events are regarded as positive example combinations, combinations already known as combinations not being drug adverse events are regarded as negative example combinations, and given combinations being neither positive example combinations nor negative example combinations are regarded as combinations other than positive and negative examples:

generating, using medical information data that includes time-series information about medical events for each patient, attribute data for each of the positive example combinations, for each of the negative example combinations and for each of the combinations other than positive and negative examples, based on the time-series information about the medical events;

learning a discriminant model by the attribute data corresponding to the positive example combinations and the attribute data corresponding to the negative example combinations;

inputting the attribute data corresponding to the combinations other than positive and negative examples to the discriminant model to calculate scores; and applying an extraction condition to the score calculated for each of the combinations other than positive and negative examples to extract combinations other than positive and negative examples being suspected to be drug adverse events, wherein the medical events for each patient include prescription of a drug for the patient and a disease observed in the patient, and wherein the medical events for each patient further include at least one of a medical act performed for the patient and an event showing that the medical act has been performed accompanying the medical act performed for the patient.

[Supplementary Note 2]

The method according to Supplementary Note 1, wherein the medical events include, for the patient, at least one of a drug newly prescribed, a disease other than diseases specified by corresponding combinations, hospitalization/non-hospitalization, request for medical expenses, and a hospital department the patient has seen a doctor.

[Supplementary Note 3]

The method according to Supplementary Note 1 or 2, wherein the attribute data is data showing, for each of the combinations, characteristics of occurrence and non-occurrence of a medical event that is at least one of a medical act performed for the patient and an event showing that the medical act has been performed, accompanying the medical act performed for the patient, at a time close to a time point when a drug and disease of the combination co-occur on the same patient on the medical information data.

[Supplementary Note 4]

The method according to Supplementary Note 3, wherein, as the attribute data, at least one of the following is used:

a pattern indicating, with a combination of a drug and a disease regarded as a combination targeted by attribute data generation in a case where the disease occurs within a predetermined first period after prescription of the drug, occurrence/non-occurrence of a predetermined kind of medical event during a second period with a predetermined length that includes a time point of the occurrence of the disease, in a time series;

an occurrence rate of a predetermined kind of medical event within a period from prescription of the drug until occurrence of a disease, with a combination of the drug and the disease regarded as a combination targeted by attribute data generation in the case where the disease occurs within the first period;

a transition probability about, with a combination of the drug and a disease regarded as a combination targeted by attribute data generation in the case where the disease occurs within the first period, whether a predetermined kind of medical event occurs during a second period with a predetermined length that includes a time point of the occurrence of the disease;

probability of, with a combination of the drug and a disease regarded as a combination targeted by attribute data generation in the case where the disease occurs within the first period, one of hypotheses being rejected when the hypothesis is correct, as a result of examination of the hypotheses, the hypotheses being a null hypothesis that there is not a difference in the rate of occurrence of a predetermined kind of medical event before and after a time point of the occurrence of the disease and an alternative hypothesis that there is a difference;

a numerical value indicating, for a drug and disease of each inputted combination, how abnormal each pattern included in a second medical event pattern set is as a pattern generated from a learned probability model, the numerical value being obtained by learning with the probability model with the use of: a first medical event pattern set in which results of extracting patterns indicating order of occurrence and non-occurrence of a predetermined kind of medical event within a predetermined third period before and after a time point of prescription of the drug for the same patient as a reference point are collected, and the second medical event pattern set in which results of extracting patterns indicating order of occurrence and non-occurrence of the predetermined kind of medical event within the third period before and after a time point of occurrence of the disease as a reference point in the case where the disease occurs within the first period after the prescription of the drug for the same patient are collected; and a degree of, for the pattern attribute data about the drug and disease of each inputted combination, how much the pattern attribute data is deviated in comparison with pattern attribute data of other inputted combinations, based on magnitude tendency of the value of each attribute item in the pattern attribute data of each combination.

[Supplementary Note 5]

The method according to Supplementary Note 3 or 4, wherein the attribute data includes, for the drug and disease of each inputted combination, data indicating which ICD10 code the disease belongs to.

[Supplementary Note 6]

The method according to any one of Supplementary Notes 1 to 5, further comprising executing preprocessing for generating time-series information about a new medical event that is not directly included in the medical information data but is used for generation of the attribute data, from time-series information about the plurality of medical events included in the medical information data.

[Supplementary Note 7]

The method according to any one of Supplementary Notes 1 to 6, further comprising extracting the combinations from the medical information data and classifying the extracted combinations into the positive example combinations and the negative example combinations based on a dictionary, before generating the attribute data.

[Supplementary Note 8]

The method according to Supplementary Note 7, wherein the dictionary in which diseases to be ignored are further described is used; and the extracted combinations that include a disease other than the diseases to be ignored are classified into the positive example combinations and the negative example combinations.

[Supplementary Note 9]

The method according to any one of Supplementary Notes 1 to 8, wherein the discriminant model for each kind of drug is used to calculate the adverse event score for the kind of drug.

[Supplementary Note 10]

The method according to any one of Supplementary Notes 1 to 8, wherein a different discriminant model is used according to whether frequency of each combination in the medical information data is high or low to calculate the adverse event score according to whether the frequency is high or low.

[Supplementary Note 11]

The method according to any one of Supplementary Notes 1 to 10, wherein an extraction result is outputted from combinations strongly suspected to be drug adverse events, based on the scores.

[Supplementary Note 12]

The method according to Supplementary Note 11, wherein the extraction result is outputted according to kinds of drugs.

[Supplementary Note 13]

The method according to any one of Supplementary Notes 1 to 10, comprising grouping the extracted combinations other than positive and negative examples.

[Supplementary Note 14]

The method according to any one of Supplementary Notes 1 to 13, comprising excluding a combination other than positive and negative examples corresponding to a combination regarded as noise from the extracted combinations other than positive and negative examples, from extraction.

[Supplementary Note 15]

The method according to any one of Supplementary Notes 1 to 13, comprising:

judging whether an inputted combination is a combination regarded as noise based on a noise condition; and the combinations other than positive and negative examples corresponding to the combination regarded as the noise are excluded from the extraction result.

[Supplementary Note 16]

The method according to any one of Supplementary Notes 1 to 15, wherein at least one of generating and adding a combination to be a pseudo positive example combination, generating and adding a combination to be a pseudo negative example combination, and deleting a part of the positive example combinations and the negative example combinations is executed to generate corrected positive example combinations and corrected negative example combinations, and wherein attribute data based on the corrected positive example combinations and the corrected negative example combinations is generated to learn the discriminant model.

[Supplementary Note 17]

The method according to Supplementary Note 16, wherein the corrected positive example combinations and the corrected negative example combinations are generated so that imbalance between the positive example combinations and the negative example combinations is corrected.

[Supplementary Note 18]

The method according to Supplementary Note 16, wherein covariate shift learning is applied to generate the corrected positive example combinations and the corrected negative example combinations.

[Supplementary Note 19]

The method according to any one of Supplementary Notes 1 to 18, wherein the positive example combinations are divided according to difference in the degree of seriousness of disease as an adverse event, and a discriminant model for each seriousness degree for discriminating a positive example combination and a discriminant model for discriminating a negative example combination are used.

[Supplementary Note 20]

The method according to any one of Supplementary Notes 1 to 19, wherein the medical information data is grouped by grouping drugs or diseases based on a grouping condition to obtain grouped medical information data, and wherein the grouped medical information data is used to create the attribute data according to the grouped drugs or diseases.

[Supplementary Note 21]

A drug adverse event extraction apparatus for extracting a combination of a drug and a disease corresponding to a drug adverse event, the apparatus comprising, on the assumption that combinations already known as combinations indicating drug adverse events are regarded as positive example combinations, combinations already known as combinations not being drug adverse events are regarded as negative example combinations, and given combinations being neither positive example combinations nor negative example combinations are regarded as combinations other than positive and negative examples:

attribute creation means that generates, using medical information data that includes time-series information about medical events for each patient stored in a storage device, attribute data for each of the positive example combinations stored in the storage device, for each of the negative example combinations stored in the storage device and for each of the combinations other than positive and negative examples stored in the storage device, based on the time-series information about the medical events, and stores the attribute data into the storage device;

learning means that learns a discriminant model by the attribute data corresponding to the positive example combinations and the attribute data corresponding to the negative example combinations;

calculation means that inputs the attribute data corresponding to the combinations other than positive and negative examples stored in the storage device to the discriminant model to calculate scores; and extraction means that applies an extraction condition to the score calculated for each of the combinations other than positive and negative examples to extract combinations other than positive and negative examples being suspected to be drug adverse events, wherein the medical events for each patient include prescription of a drug for the patient and a disease observed in the patient, and wherein the medical events for each patient further include at least one of a medical act performed for the patient and an event showing that the medical act has been performed accompanying the medical act performed for the patient.

[Supplementary Note 22]

The apparatus according to Supplementary Note 21, wherein the medical events include, for the patient, at least one of a drug newly prescribed, a disease other than diseases specified by corresponding combinations, hospitalization/ non-hospitalization, request for medical expenses, and a hospital department the patient has seen a doctor.

[Supplementary Note 23]

The apparatus according to Supplementary Note 21 or 22, wherein the attribute data is data showing, for each of the combinations, characteristics of occurrence and non-occurrence of a medical event that is at least one of a medical act performed for the patient and an event showing that the medical act has been performed, accompanying the medical act performed for the patient, at a time close to a time point when a drug and disease of the combination co-occur on the same patient on the medical information data.

[Supplementary Note 24]

The apparatus according to Supplementary Note 21 or 22, wherein, as the attribute data, at least one of the following is used:

a pattern indicating, with a combination of a drug and a disease regarded as a combination targeted by attribute data generation in a case where the disease occurs within a predetermined first period after prescription of the drug, occurrence/non-occurrence of a predetermined kind of medical event during a second period with a predetermined length that includes a time point of the occurrence of the disease, in a time series;

an occurrence rate of a predetermined kind of medical event within a period from prescription of the drug until occurrence of a disease, with a combination of the drug and the disease regarded as a combination targeted by attribute data generation in the case where the disease occurs within the first period;

a transition probability about, with a combination of the drug and a disease regarded as a combination targeted by attribute data generation in a case where the disease occurs within the first period, whether a predetermined kind of medical event occurs during a second period with a predetermined length that includes a time point of the occurrence of the disease;

probability of, with a combination of the drug and a disease regarded as a combination targeted by attribute data generation in a case where the disease occurs within the first period, one of hypotheses being rejected when the hypothesis is correct, as a result of examination of the hypotheses, the hypotheses being a null hypothesis that there is not a difference in the rate of occurrence of a predetermined kind of medical event before and after a time point of the occurrence of the disease and an alternative hypothesis that there is a difference;

a numerical value indicating, for a drug and disease of each inputted combination, how abnormal each pattern included in a second medical event pattern set is as a pattern generated from a learned probability model, the numerical value being obtained by learning with the probability model with the use of: a first medical event pattern set in which results of extracting patterns indicating order of occurrence and non-occurrence of a predetermined kind of medical event within a predetermined third period before and after a time point of prescription of the drug for the same patient as a reference point are collected, and the second medical event pattern set in which results of extracting patterns indicating order of occurrence and non-occurrence of the predetermined kind of medical event within the third period before and after a time point of occurrence of the disease as a reference point in a case where the disease occurs within the first period after the prescription of the drug for the same patient are collected; and a degree of, for the pattern attribute data about the drug and disease of each inputted combination, how much the pattern attribute data is deviated in comparison with pattern attribute data of other inputted combinations, based on magnitude tendency of the value of each attribute item in the pattern attribute data of each combination.

[Supplementary Note 25]

The apparatus according to Supplementary Note 23 or 24, wherein the attribute data includes, for the drug and disease of each inputted combination, data indicating which ICD10 code the disease belongs to.

[Supplementary Note 26]

The apparatus according to any one of Supplementary Notes 21 to 25, wherein said attribute creation means executes preprocessing for generating time-series information about a new medical event that is not directly included in the medical information data but is used for generation of the attribute data, from time-series information about the plurality of medical events included in the medical information data.

[Supplementary Note 27]

The apparatus according to any one of Supplementary Notes 21 to 16, further comprising extraction means that extracts the combinations from the medical information data, classifies the extracted combinations into the positive example combinations and the negative example combinations based on a dictionary, and stores the positive example combinations and the negative example combinations into the storage device.

[Supplementary Note 28]

The apparatus according to Supplementary Note 27, wherein diseases to be ignored are further described in the dictionary; and said combination extraction means classifies the extracted combinations that include a disease other than the diseases to be ignored into the positive example combinations and the negative example combinations.

[Supplementary Note 29]

The apparatus according to any one of Supplementary Notes 21 to 28, wherein the discriminant model is provided for each kind of drug, and said calculation means calculates the adverse event score for the kind of drug.

[Supplementary Note 30]

The apparatus according to any one of Supplementary Notes 21 to 28, wherein a different discriminant model according to whether frequency of each combination in the medical information data is high or low is provided, and said calculation means calculates the adverse event score according to whether the frequency is high or low.

[Supplementary Note 31]

The apparatus according to any one of Supplementary Notes 21 to 30, wherein said extraction means outputs an extraction result from combinations strongly suspected to be drug adverse events based on the scores.

[Supplementary Note 32]

The apparatus according to Supplementary Note 31, wherein said extraction means outputs the extraction result according to kinds of drugs.

[Supplementary Note 33]

The apparatus according to any one of Supplementary Notes 21 to 30, comprising grouping means that performs grouping for the result obtained by said extraction means.

[Supplementary Note 34]

The apparatus according to any one of Supplementary Notes 21 to 33, wherein said extraction means excludes the combinations other than positive and negative examples corresponding to the combination regarded as noise from extraction.

[Supplementary Note 35]

The apparatus according to any one of Supplementary Notes 21 to 33, further comprising noise extraction means that judges whether an inputted combination is a combination regarded as noise based on a noise condition, wherein said extraction means excludes the combinations other than positive and negative examples corresponding to the combination regarded as noise from extraction.

[Supplementary Note 36]

The apparatus according to any one of Supplementary Notes 21 to 35, further comprising correction means that executes at least one of generating and adding a combination to be a pseudo positive example combination, generating and adding a combination to be a pseudo negative example combination, and deleting a part of the positive example combinations and the negative example combinations to generate corrected positive example combinations and corrected negative example combinations, wherein said attribute creation means creates attribute data corresponding to the corrected positive example combinations and attribute data based on the corrected negative example combinations, and wherein said learning means learns a discriminant model by the attribute data corresponding to the corrected positive example combinations and the attribute data corresponding to the corrected negative example combinations.

[Supplementary Note 37]

The apparatus according to Supplementary Note 36, wherein said correction means generates the corrected positive example combinations and the corrected negative example combinations so that imbalance between the positive example combinations and the negative example combinations is corrected.

[Supplementary Note 38]

The apparatus according to Supplementary Note 36, wherein said correction means comprises covariate shift means that applies covariate shift learning to generate the corrected positive example combinations and the corrected negative example combinations.

[Supplementary Note 39]

The apparatus according to any one of Supplementary Notes 31 to 38, wherein the positive example combinations are divided according to difference in the degree of seriousness of disease as an adverse event, and a discriminant model for each seriousness degree for discriminating a positive example combination and a discriminant model for discriminating a negative example combination are used.

[Supplementary Note 40]

The apparatus according to any one of Supplementary Notes 31 to 39, comprising prior grouping means that groups the medical information data by grouping drugs or diseases based on a grouping condition to obtain grouped medical information data, and stores the grouped medical information data into the storage device, wherein said attribute creation means uses the grouped medical information data to create the attribute data according to the grouped drugs or diseases.

[Supplementary Note 41]

A program for causing a computer to which a combination of a drug and a disease is inputted to, on the assumption that combinations already known as combinations indicating drug adverse events are regarded as positive example combinations, combinations already known as combinations not being drug adverse events are regarded as negative example combinations, and given combinations being neither positive example combinations nor negative example combinations are regarded as combinations other than positive and negative examples, function as:

attribute creation means that generates, using medical information data that includes time-series information about medical events for each patient, attribute data for each of the positive example combinations, for each of the negative example combinations and for each of the combinations other than positive and negative examples, based on the time-series information about the medical events;

learning means that learns a discriminant model by the attribute data corresponding to the positive example combinations and the attribute data corresponding to the negative example combinations;

calculation means that inputs the attribute data corresponding to the combinations other than positive and negative examples to the discriminant model to calculate scores; and extraction means that applies an extraction condition to the score calculated for each of the combinations other than positive and negative examples to extract combinations other than positive and negative examples being suspected to be drug adverse events, wherein the medical events for each patient include prescription of a drug for the patient and a disease observed in the patient, and the medical events for each patient further include at least one of a medical act performed for the patient and an event showing that the medical act has been performed accompanying the medical act performed for the patient.

REFERENCE SIGNS LIST 11 processor;
12 storage device;
13 communication interface (I/F) unit;
14 operation input unit;
15 screen display unit;
21 input unit;
22 attribute data creation unit;
23 discriminant model learning unit;
24 adverse event score calculation unit;
25 extraction unit;
26 combination extraction unit;
27,28 grouping unit;
31 noise extraction unit;
32 imbalance correction unit;
33 covariate shift processing unit.

The invention claimed is:

1. A drug adverse event extraction method of extracting a combination of a drug and a disease corresponding to a drug adverse event, assuming that combinations already known as combinations indicating drug adverse events are regarded as positive example combinations, combinations already known as combinations not being drug adverse events are regarded as negative example combinations, and given combinations being neither positive example combinations nor negative example combinations are regarded as combinations other than positive and negative examples, the method comprising:

retrieving a plurality of the positive example combinations indicating the drug adverse events for a plurality of diseases and a plurality of drugs stored in a storage device, each positive example combination being one of the plurality of diseases and one of the plurality of drugs associated together;

retrieving a plurality of the negative example combinations not indicating the drug adverse events stored in the storage device, each negative example combination being one of the plurality of diseases and one of the plurality of drugs associated together;

retrieving a plurality of the combinations other than positive and negative examples, each combination other than the positive and negative examples being one of the plurality of diseases and one of the plurality of drugs associated together;

generating, using medical information data that includes time-series information about medical events for each patient, attribute data for each of the retrieved positive example combinations, for each of the retrieved negative example combinations, and for each of the retrieved combinations other than positive and negative examples, based on the time-series information about the medical events;

reading the attribute data for each of the positive example combinations and the attribute data for each of the negative example combinations, and machine-learning a discriminant model installed in a computer based on the attribute data corresponding to the read positive example combinations and the attribute data corresponding to the read negative example combinations;

inputting the attribute data corresponding to the combinations other than positive and negative examples to the discriminant model and calculating scores;

applying an extraction condition to the score calculated for each of the combinations other than positive and negative examples to extract combinations other than positive and negative examples being suspected to be drug adverse events; and outputting the extracted combinations suspected to be drug adverse events to one of a display or outside via a communication interface, wherein the medical events for each patient include prescription of one of the drugs for the patient and one of the diseases observed in the patient, and wherein the medical events for each patient further include at least one of a medical act performed for the patient and an event showing that the medical act has been performed accompanying the medical act performed for the patient.

2. The method according to claim 1, wherein the medical events include, for the patient, at least one of a newly-prescribed drug, a disease other than diseases specified by corresponding combinations, hospitalization/non-hospitalization, a request for medical expenses, and a hospital department at which the patient has seen a doctor.

3. The method according to claim 1, wherein the attribute data is data showing, for each of the combinations, characteristics of occurrence and non-occurrence of a medical event that is at least one of a medical act performed for the patient and an event showing that the medical act has been performed, accompanying the medical act performed for the patient, at a time close to a time point when a drug and disease of the combination co-occur on the same patient on the medical information data.

4. The method according to claim 3, wherein, as the attribute data, at least one of the following is used:
a pattern indicating, with a combination of a drug and a disease regarded as a combination targeted by attribute data generation in a case where the disease occurs within a predetermined first period after prescription of the drug, occurrence/non-occurrence of a predetermined kind of medical event during a second period with a predetermined length that includes a time point of the occurrence of the disease, in a time series, an occurrence rate of a predetermined kind of medical event within a period from prescription of the drug until occurrence of a disease, with a combination of the drug and the disease regarded as a combination targeted by attribute data generation in the case where the disease occurs within the first period, a transition probability about, with a combination of the drug and a disease regarded as a combination targeted by attribute data generation in the case where the disease occurs within the first period, whether a predetermined kind of medical event occurs during a second period with a predetermined length that includes a time point of the occurrence of the disease, a probability of, with a combination of the drug and a disease regarded as a combination targeted by attribute data generation in the case where the disease occurs within the first period, one of hypotheses being rejected when the hypothesis is correct, as a result of examination of the hypotheses, the hypotheses being a null hypothesis that there is not a difference in the rate of occurrence of a predetermined kind of medical event before and after a time point of the occurrence of the disease and an alternative hypothesis that there is a difference, a numerical value indicating, for a drug and a disease of each inputted combination, how abnormal each pattern included in a second medical event pattern set is as a pattern generated from a learned probability model, the numerical value being obtained by learning the probability model with the use of: a first medical event pattern set in which results of extracting patterns indicating order of occurrence and non-occurrence of a predetermined kind of medical event within a predetermined third period before and after a time point of prescription of the drug for the same patient as a reference point are collected, and the second medical event pattern set in which results of extracting patterns indicating order of occurrence and non-occurrence of the predetermined kind of medical event within the third period before and after a time point of occurrence of the disease as a reference point in the case where the disease occurs within the first period after the prescription of the drug for the same patient are collected, and a degree of, for the pattern attribute data about the drug and disease of each inputted combination, how much the pattern attribute data is deviated in comparison with pattern attribute data of other inputted combinations, based on magnitude tendency of a value of each attribute item in the pattern attribute data of each combination.

5. The method according to claim 3, wherein the attribute data includes, for the drug and disease of each inputted combination, data indicating which ICD10 code the disease belongs to.

6. The method according to claim 1, further comprising executing preprocessing for generating time-series information about a new medical event that is not directly included in the medical information data but is used for generation of the attribute data, from time-series information about the plurality of medical events included in the medical information data.

7. The method according to claim 1, further comprising extracting the combinations from the medical information data and classifying the extracted combinations into the positive example combinations and the negative example combinations based on a dictionary, before generating the attribute data.

8. The method according to claim 1, wherein the discriminant model for each kind of drug is used to calculate the adverse event score for the kind of drug.

9. The method according to claim 1, wherein a different discriminant model is used according to whether frequency of each combination in the medical information data is high or low to calculate the adverse event score according to whether the frequency is high or low.

10. The method according to claim 1, further comprising grouping the extracted combinations other than positive and negative examples.

11. The method according to claim 1, wherein at least one of generating and adding a combination to be a pseudo positive example combination, generating and adding a combination to be a pseudo negative example combination, and deleting a part of the positive example combinations and the negative example combinations is executed to generate corrected positive example combinations and corrected negative example combinations, and
wherein attribute data based on the corrected positive example combinations and the corrected negative example combinations is generated to learn the discriminant model.

12. The method according to claim 1, wherein the positive example combinations are divided according to difference in the degree of seriousness of disease as an adverse event, and a discriminant model for each seriousness degree for discriminating a positive example combination and a discriminant model for discriminating a negative example combination are used.

13. The method according to claim 1,
wherein the medical information data is grouped by grouping drugs or diseases based on a grouping condition to obtain grouped medical information data, and
wherein the grouped medical information data is used to create the attribute data according to the grouped drugs or diseases.

14. A drug adverse event extraction apparatus for extracting a combination of a drug and a disease corresponding to a drug adverse event, assuming that combinations already known as combinations indicating drug adverse events are regarded as positive example combinations, combinations already known as combinations not being drug adverse events are regarded as negative example combinations, and given combinations being neither positive example combinations nor negative example combinations are regarded as combinations other than positive and negative examples, the apparatus comprising:
an input unit configured to
retrieve a plurality of the positive example combinations indicating the drug adverse events for a plurality of diseases and a plurality of drugs stored in a storage device, each positive example combination being one of the plurality of diseases and one of the plurality of drugs associated together,
retrieve a plurality of the negative example combinations not indicating the drug adverse events stored in the storage device, each negative example combination being one of the plurality of diseases and one of the plurality of drugs associated together, and
retrieve a plurality of the combinations other than positive and negative examples, each combination other than the positive and negative examples being one of the plurality of diseases and one of the plurality of drugs associated together;
an attribute data creation unit that generates, using medical information data that includes time-series information about medical events for each patient stored in the storage device, attribute data for each of the retrieved positive example combinations stored in the storage device, for each of the retrieved negative example combinations stored in the storage device and for each of the retrieved combinations other than positive and negative examples stored in the storage device, based on the time-series information about the medical events, and stores the attribute data into the storage device;
a machine-learning unit that reads the attribute data for each of the positive example combinations and the attribute data for each of the negative example combinations, and learns a discriminant model installed in a computer based on the attribute data corresponding to the positive example combinations and the attribute data corresponding to the negative example combinations;
a calculation unit that inputs the attribute data corresponding to the combinations other than positive and negative examples stored in the storage device to the discriminant model and calculates scores;
an extraction unit that applies an extraction condition to the score calculated for each of the combinations other than positive and negative examples to extract combinations other than positive and negative examples being suspected to be drug adverse events; and
one of a display configured to display the extracted combinations suspected to be drug adverse events, and a communication interface configured to output the extracted combinations suspected to be drug adverse events to outside,
wherein the medical events for each patient include prescription of a drug for the patient and a disease observed in the patient, and
wherein the medical events for each patient further include at least one of a medical act performed for the patient and an event showing that the medical act has been performed accompanying the medical act performed for the patient.

15. The apparatus according to claim 14, wherein the medical events include, for the patient, at least one of a newly-prescribed drug, a disease other than diseases specified by corresponding combinations, hospitalization/non-hospitalization, a request for medical expenses, and a hospital department at which the patient has seen a doctor.

16. The apparatus according to claim 14, wherein the attribute data is data showing, for each of the combinations, characteristics of occurrence and non-occurrence of a medical event that is at least one of a medical act performed for the patient and an event showing that the medical act has been performed, accompanying the medical act performed for the patient, at a time close to a time point when a drug and disease of the combination co-occur on the same patient on the medical information data.

17. The apparatus according to claim 14, further comprising a combination extraction unit that extracts the combinations from the medical information data, classifies the extracted combinations into the positive example combinations and the negative example combinations based on a dictionary, and stores the positive example combinations and the negative example combinations into the storage device.

18. The apparatus according to claim 14, further comprising a grouping unit that performs grouping for a result obtained by said extraction unit.

19. The apparatus according to claim 14, further comprising a correction unit that executes at least one of generating and adding a combination to be a pseudo positive example combination, generating and adding a combination to be a pseudo negative example combination, and deleting a part of the positive example combinations and the negative example combinations to generate corrected positive example combinations and corrected negative example combinations,
- wherein said attribute creation unit creates attribute data corresponding to the corrected positive example combinations and attribute data based on the corrected negative example combinations, and
- wherein said learning unit learns a discriminant model by the attribute data corresponding to the corrected positive example combinations and the attribute data corresponding to the corrected negative example combinations.

20. The apparatus according to claim 14, further comprising a prior grouping unit that groups the medical information data by grouping drugs or diseases based on a grouping condition to obtain grouped medical information data, and stores the grouped medical information data into the storage device,
- wherein said attribute creation unit uses the grouped medical information data to create the attribute data according to the grouped drugs or diseases.

* * * * *